United States Patent
Nagaishi et al.

(10) Patent No.: US 12,019,061 B2
(45) Date of Patent: Jun. 25, 2024

(54) TOILET SEAT APPARATUS AND EXCREMENT DETECTION APPARATUS

(71) Applicant: TOTO LTD., Kitakyushu (JP)

(72) Inventors: Masayuki Nagaishi, Fukuoka (JP); Yuta Sakai, Fukuoka (JP); Satoko Kizuka, Fukuoka (JP); Ryo Oi, Fukuoka (JP); Takeshi Takaki, Fukuoka (JP); Naoya Takeuchi, Fukuoka (JP); Hitoaki Higuchi, Fukuoka (JP); Masamichi Tosaki, Fukuoka (JP)

(73) Assignee: TOTO LTD., Fukuoka (JP)

( * ) Notice: Subject to any disclaimer, the term of this patent is extended or adjusted under 35 U.S.C. 154(b) by 117 days.

(21) Appl. No.: 17/277,865

(22) PCT Filed: Aug. 28, 2020

(86) PCT No.: PCT/JP2020/032753
§ 371 (c)(1),
(2) Date: Mar. 19, 2021

(87) PCT Pub. No.: WO2021/040019
PCT Pub. Date: Mar. 4, 2021

(65) Prior Publication Data
US 2022/0178907 A1    Jun. 9, 2022

(30) Foreign Application Priority Data

Aug. 30, 2019 (JP) .................. 2019-159040
Jul. 14, 2020 (JP) .................. 2020-120710

(51) Int. Cl.
*G01N 33/483* (2006.01)
*E03D 11/13* (2006.01)
*E03D 9/08* (2006.01)

(52) U.S. Cl.
CPC ......... *G01N 33/4833* (2013.01); *E03D 11/13* (2013.01); *E03D 9/08* (2013.01)

(58) Field of Classification Search
CPC .. G01N 33/4833; G01N 21/27; G01N 33/483; G01N 21/84; E03D 11/13;
(Continued)

(56) References Cited

U.S. PATENT DOCUMENTS 4,636,474 A * 1/1987 Ogura .................. E03D 9/00
                                                      4/314
4,962,550 A * 10/1990 Ikenaga ................ E03D 9/00
                                                      600/573
(Continued)

FOREIGN PATENT DOCUMENTS

CN  106574920    4/2017
JP  2005106514   4/2005
(Continued)

OTHER PUBLICATIONS

English translation Ueda 2018.*
(Continued)

*Primary Examiner* — Mohamed K Amara
(74) *Attorney, Agent, or Firm* — Amin, Turocy & Watson, LLP

(57) ABSTRACT

A toilet seat apparatus according to an embodiment includes: a toilet seat on which a user sits; a light emitting unit including a light emitting element that emits light; a light receiving unit including a light receiving element that receives light; and a control unit that controls energization of the light emitting element and application of voltage to the light receiving element, in which the control unit performs light reception control including transmitting a control instruction to open an electronic shutter to the light receiving element and energizing the light emitting element so as to (Continued)

permit reception of the reflected light from feces, and performs control of setting an interval from a start of execution of one light reception control to execution of light reception control subsequent to the one light reception control, to 0.2 milliseconds or more.

9 Claims, 29 Drawing Sheets

(58) Field of Classification Search
CPC .. E03D 9/08; E03D 9/00; E03D 11/06; A47K 13/30; A47K 13/24; A61B 10/0038; G01J 3/46
See application file for complete search history.

(56) References Cited

U.S. PATENT DOCUMENTS

| | | | | |
|---|---|---|---|---|
| 9,380,918 | B2* | 7/2016 | Murphy | E03D 11/00 |
| 11,478,114 | B2* | 10/2022 | Sakai | G01V 8/12 |
| 2017/0303901 | A1 | 10/2017 | Sekine | |
| 2019/0368181 | A1* | 12/2019 | Yaoka | A61L 2/10 |
| 2020/0008786 | A1 | 1/2020 | Sekine | |
| 2021/0345843 | A1* | 11/2021 | Sakai | F21V 33/004 |
| 2022/0178126 | A1* | 6/2022 | Azuma | A61B 10/0038 |
| 2022/0357269 | A1* | 11/2022 | Oi | E03D 9/00 |
| 2023/0009654 | A1* | 1/2023 | Takaki | G16H 40/63 |
| 2024/0057982 | A1 | 2/2024 | Sekine | |

FOREIGN PATENT DOCUMENTS

| | | |
|---|---|---|
| JP | 2008248669 | 10/2008 |
| JP | 2016-004005 | 1/2016 |
| JP | 5861977 | 2/2016 |
| JP | 2018146244 | 9/2018 |
| JP | 2018143269 | 9/2019 |
| WO | 2018/159369 | 9/2018 |

OTHER PUBLICATIONS

English translation Sekine 2016.*
International Search Report and Written Opinion for International Application No. PCT/JP2020/032753 dated Oct. 6, 2020, 11 pages.

* cited by examiner

TOILET SEAT APPARATUS AND EXCREMENT DETECTION APPARATUS

FIELD

The disclosed embodiment relates to a toilet seat apparatus and an excrement detection apparatus.

BACKGROUND

Conventionally, there is a known toilet seat apparatus including a sensor capable of detecting feces (hereinafter also referred to as excrement) discharged in a toilet bowl. (refer to, Patent Literature 1, for example)

The sensor used in the toilet seat apparatus in the above-described conventional technique includes a light emitting unit capable of emitting light to the feces and a light receiving unit capable of receiving the reflected light from the feces, and is capable of acquiring biological information regarding the health condition of a user based on the feces.

CITATION LIST

Patent Literature

Patent Literature 1: JP 5861977 B2

SUMMARY

Technical Problem

However, as in the above-described conventional technique, in order to detect the falling feces, there is a need to emit light to the falling feces. However, it is difficult to predict a timing at which the feces will fall. At this time, in order not to overlook the fall of feces, there is a need to reduce the time (shutter speed) during which the light receiving element provided in the light receiving unit is exposed to light. At this time, by setting the shutter speed too high, the amount of light received by the light receiving element would be insufficient, which would cause a problem of difficulty in accurately acquiring feces information.

The disclosed embodiment aims to provide a toilet seat apparatus and an excrement detection apparatus that suppress occurrence of insufficient amount of light in detection.

Solution to Problem

A toilet seat apparatus to be placed on an upper part of a toilet bowl having a bowl unit that receives excrement, the toilet seat apparatus according to an aspect of the embodiment, comprising: a toilet seat on which a user sits; a light emitting unit including a light emitting element that emits light; a light receiving unit including a light receiving element that receives light; and a control unit that controls energization of the light emitting element and application of voltage to the light receiving element, wherein the control unit performs light reception control including transmitting a control instruction to open an electronic shutter to the light receiving element and energizing the light emitting element so as to permit reception of the reflected light from feces, and performs control of setting an interval from a start of execution of one light reception control to execution of light reception control subsequent to the one light reception control, to 0.2 milliseconds or more.

According to a toilet seat apparatus in one aspect of the embodiment, which is a toilet seat apparatus including a control unit capable of controlling an electronic shutter function of adjusting the time during which the light receiving element is exposed to light by voltage application to the light receiving element, by energizing the light emitting element while the shutter is open, an interval between a first execution of a light reception control that enables reception of the reflected light from the feces and a next execution of light reception control is set to 0.2 milliseconds or more, that is, by executing the light reception control at a rate of 5000 times/second or less, it is possible to prevent overlooking of falling of the feces and to suppress the occurrence of shortage of the amount of light received by the light receiving element.

In the toilet seat apparatus according to an aspect of the embodiment, wherein the light emitting unit emits light toward falling feces discharged by the user, and the light receiving unit receives the reflected light from the feces corresponding to the light emitted by the light emitting unit.

According to the toilet seat apparatus in one aspect of the embodiment, when the toilet seat apparatus is placed on an upper part of the toilet bowl, by emitting light to the feces discharged by the user, and receiving the reflected light from the feces corresponding to the emitted light, it is possible to acquire information regarding the feces discharged in the toilet bowl.

In the toilet seat apparatus according to an aspect of the embodiment, wherein the control unit performs control of setting an interval from a start of execution of the one light reception control to execution of the subsequent light reception control, to 600 milliseconds or less.

According to the toilet seat apparatus in one aspect of the embodiment, in a case where the interval (hereinafter, also referred to as "light reception control interval") from the start of execution of one light reception control to the execution of the subsequent light reception control is 600 milliseconds, one type of beam of light is scanned (emitted) twice to a region having a length of 100 mm, making it possible to detect the presence or absence of feces.

In the toilet seat apparatus according to an aspect of the embodiment, wherein the control unit performs control of setting an interval from a start of execution of the one light reception control to execution of the subsequent light reception control, to 300 milliseconds or less.

According to the toilet seat apparatus in one aspect of the embodiment, in a case where the light reception control interval is 300 milliseconds, one type of beam of light is scanned (emitted) four times to a region having a length of 100 mm, making it possible to detect the presence or absence of feces with higher accuracy compared to the case where the light reception control interval is 600 milliseconds. In addition, in a case where the light reception control interval is 300 milliseconds, two types of light are scanned (emitted) twice to a region of having a length of 100 mm, making it possible to estimate the representative color of the feces.

In the toilet seat apparatus according to an aspect of the embodiment, wherein the control unit performs control of setting an interval from a start of execution of the one light reception control to execution of the subsequent light reception control, to 100 milliseconds or less.

According to the toilet seat apparatus in one aspect of the embodiment, in a case where the light reception control interval is 100 milliseconds, one type of beam of light is scanned (emitted) 12 times in a region having a length of 100 mm, making it possible to detect the contour of the feces. In this manner, the contour of the feces can be detected in a case where the light reception control interval is 100 milliseconds, making it possible to detect whether the feces is disfigured with a large amount of water, or keeps its shape with a small amount of water.

In the toilet seat apparatus according to an aspect of the embodiment, wherein the control unit performs control of setting an interval from a start of execution of the one light reception control to execution of the subsequent light reception control, to 50 milliseconds or less.

According to the toilet seat apparatus in one aspect of the embodiment, in a case where the light reception control interval is 50 milliseconds, one type of beam of light is scanned (emitted) 25 times to a region having a length of 100 mm, making it possible to detect the pattern of cracks appearing on the surface of the feces due to the reduced amount of moisture contained in the feces, leading to estimation of the properties of the feces corresponding to the amount of moisture in the feces. In addition, in a case where the light reception control interval is 50 milliseconds, two types of light are scanned (emitted) 12 times to a region of having a length of 100 mm, making it possible to detect the color distribution of the feces.

In the toilet seat apparatus according to an aspect of the embodiment, wherein the control unit performs control of setting an interval from a start of execution of the one light reception control to execution of the subsequent light reception control, to 10 milliseconds or less.

The prolonged exposure to the light of the light receiving element would increase the amount of light reception, due to the light reflected in the toilet bowl and the light originated from lighting equipment installed in the toilet space incident from between the feet of the seated user in addition to the light reflected by the feces. This increase of light reception might cause burial of data based on the light reflected by the feces. According to the toilet seat apparatus in one aspect of the embodiment, the interval of execution of the first light reception control and the next execution is set to 10 milliseconds or less, that is, the light reception control is executed at a speed of 100 times/second or more. With this control, it is possible to suppress the difficulty in performing detecting properly due to the slow control speed, and to suppress the burial of data based on the reflected light from the feces due to the increase of the amount of light received due to the light reflected in the toilet bowl and the light from the lighting equipment installed in the toilet space.

In the toilet seat apparatus according to an aspect of the embodiment, wherein the light emitting unit includes a plurality of light emitting elements each of which emits light, the plurality of light emitting elements is capable of emitting beams of light of different wavelengths, the control unit energizes only one light emitting element among the plurality of light emitting elements in the one light reception control, changes the light emitting element to be energized in the subsequent light reception control every time the one light reception control is completed, and performs control of setting the interval from the start of execution of one light reception control to the execution of the subsequent light reception control to 1.6 milliseconds or less.

In order to detect the color of feces, there are conceivable methods including: a method (first method) of emitting white light including all wavelengths in a visible light region to the feces and dispersing the reflected light from the feces on the light receiving unit; and a method (second method) of sequentially emitting to the feces beams of light of a plurality of different wavelengths. At this time, in order to detect the color of the feces by the second method executable at a lower cost, it is necessary to emit beams of light of a plurality of different wavelengths to the same part of the feces. At this time, there occurs a problem that exposing the light receiving element of one wavelength to light for a long time would disable emission of beams of light of a plurality of different wavelengths to the same part of the feces. According to the toilet seat apparatus in one aspect of the embodiment, the power generation element to be energized next is changed every time the light reception control is completed, thereby sequentially emitting beams of light of a plurality of different wavelengths. In addition, by setting the interval between the first execution of the light reception control and the next execution to 1.6 milliseconds or less, that is, by executing the light reception control at a speed of 625 times/second or more, it is possible to emit the beams of light of a plurality of different wavelengths to the same part of the feces.

In the toilet seat apparatus according to an aspect of the embodiment, wherein the control unit sets energization time of the light emitting element to be different for each of wavelengths emitted by the light emitting element in the light reception control.

In order to accurately detect the color of feces, it is preferable to equalize the amount of light received by the light receiving element for the beams of light of a plurality of wavelengths. At this time, there is an issue that the light emitting elements capable of emitting individual wavelengths have the amount of light different from each other. For example, a light emitting element that emits a wavelength close to blue tends to have a large amount of light, while a light emitting element that emits a wavelength close to green tends to have a small amount of light. Therefore, in order to accurately detect the color of feces, it is not preferable to make the energization time of all the light emitting elements uniform. According to the toilet seat apparatus in one aspect of the embodiment, the energization time of the light emitting element is set to be different for each of wavelengths emitted by the light emitting element, making it possible to detect the color of feces with higher accuracy.

An excrement detection apparatus to be disposed on a toilet bowl having a bowl unit that receives excrement, the excrement detection apparatus comprising: a light emitting unit including a light emitting element that emits light; a light receiving unit including a light receiving element that receives light; and a control unit that controls energization of the light emitting element and application of voltage to the light receiving element, wherein the control unit performs light reception control including transmitting a control instruction to open an electronic shutter to the light receiving element and energizing the light emitting element so as to permit reception of the reflected light from feces, and performs control of setting an interval from a start of execution of one light reception control to execution of light reception control subsequent to the one light reception control, to 0.2 milliseconds or more.

According to an excrement detection apparatus in one aspect of the embodiment, which is a toilet seat apparatus including a control unit capable of controlling an electronic shutter function for adjusting the time during which the light receiving element is exposed to light by voltage application to the light receiving element, by energizing the light emitting element while the shutter is open, an interval between a first execution of a light reception control that enables reception of the reflected light from the feces and a next execution of light reception control is set to 0.2 milliseconds or more, that is, by executing the light reception control at a rate of 5000 times/second or less, it is possible to prevent overlooking of fall of the feces and to suppress the occurrence of shortage of the amount of light received by the light receiving element.

Advantageous Effects of Invention

In one aspect of the embodiment, it is possible to suppress the shortage of the amount of light in detection.

DESCRIPTION OF EMBODIMENTS

Hereinafter, embodiments of a toilet seat apparatus and an excrement detection apparatus disclosed in the present application will be described in detail with reference to the accompanying drawings. The present invention is not limited to the embodiments described below. The following will describe processes related to information collection of excrement of a user of a toilet room (hereinafter also referred to as "excretion information collection") and configurations for performing the processes. Before this, various configurations such as toilet systems will be first described as prerequisites.

<1. Configuration of Toilet System>

Figure 1:
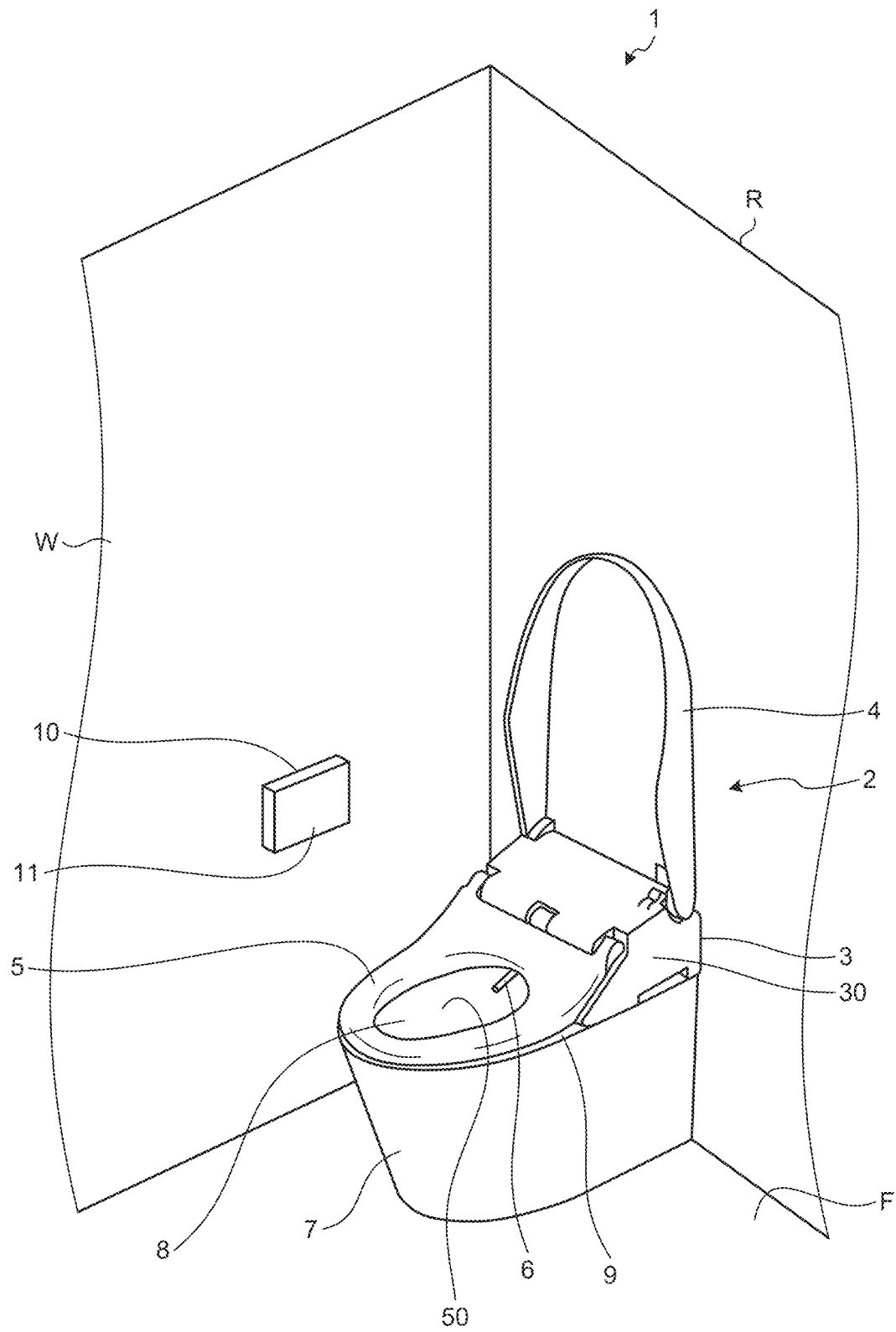
FIG. 1 is a perspective view illustrating an example of a configuration of a toilet system according to a first embodiment.

First, a configuration of a toilet system according to a first embodiment will be described with reference to FIG. 1. FIG. 1 is a perspective view illustrating an example of a configuration of the toilet system according to the first embodiment.

As illustrated in FIG. 1, a toilet system 1 includes a toilet seat apparatus 2 and an operation device 10. As illustrated in FIG. 1, in a toilet room R, a Western-style toilet bowl (hereinafter referred to as a "toilet bowl") 7 is installed on a floor surface F. In the following, the direction from the floor surface F toward the space of the toilet room R is described as upward or upper. The toilet seat apparatus 2 is provided on the upper part of the toilet bowl 7.

The toilet bowl 7 is formed of ceramics, for example. A bowl unit 8 is provided on the toilet bowl 7. The bowl unit 8 is a part having a downwardly recessed shape, configured to receive excrement of the user. The toilet bowl 7 is not limited to the floor mounted type as illustrated in the figure, and may be of any type including the type such as a wall-mounted type, as long as the toilet system 1 is applicable. The toilet bowl 7 includes a rim 9 over the entire circumference of the end of the opening provided in the bowl unit 8. The toilet room R may include a cleansing water tank for storing cleansing water near the toilet bowl 7, or may be a tankless type unit in which a cleansing water tank is not installed.

For example, when a cleansing operation unit (not illustrated) for cleansing provided in the toilet room R is operated by the user, cleansing water is supplied to the bowl unit 8 of the toilet bowl 7 so as to perform the toilet bowl cleansing. The cleansing operation unit may be a touch operation on the operation lever or the toilet bowl cleansing object displayed on the operation device 10. The cleansing operation unit is not limited to the one that manually cleans the toilet bowl by the user, such as an operation lever, but also the one that cleans the toilet bowl by human detection of a sensor that detects the user, such as a seating sensor may be provided.

The toilet seat apparatus 2 is attached to the upper part of the toilet bowl 7, and includes a main body 3, a toilet lid 4, a toilet seat 5, and a cleansing nozzle 6. The toilet seat apparatus 2 is placed on the upper part of the toilet bowl 7 including the bowl unit 8 that receives excrement. The toilet seat apparatus 2 is placed on the upper part of the toilet bowl 7 so that the cleansing nozzle 6 advances to the bowl unit 8 before injecting the cleansing water. The toilet seat apparatus 2 may be detachably attached to the toilet bowl 7 or may be attached to be integrated with the toilet bowl 7.

As illustrated in FIG. 1, the toilet seat 5 is formed in an annular shape having an opening 50 in the center, and is arranged along the rim 9 at a position overlapping the opening of the toilet bowl 7. The toilet seat 5 is a seat on which the user sits. The toilet seat 5 functions as a seating portion that supports the buttocks of the user seated. Furthermore, as illustrated in FIG. 1, the toilet lid 4 and the toilet seat 5 are each pivotally supported, at one end, by the main body 3, and are pivotally (openable and closable) attached around the shaft support of the main body 3. The toilet lid 4 is attached to the toilet seat apparatus 2 as needed, and the toilet seat apparatus 2 does not have to include the toilet lid 4.

The cleansing nozzle 6 is a nozzle for discharging water for cleansing. The cleansing nozzle 6 can inject cleansing water. The cleansing nozzle 6 can inject cleansing water toward the user. The cleansing nozzle 6 is a nozzle for genital/anal cleansing. Driven by a drive source such as an electric motor (nozzle motor 61 or the like in FIG. 4), the cleansing nozzle 6 can perform advance/retract movement with respect to a main body cover 30 which is the housing of the main body 3. Furthermore, the cleansing nozzle 6 is connected to a water source such as a water pipe (not illustrated). As illustrated in FIG. 1, when the cleansing nozzle 6 is in a position advanced (hereinafter, also referred to as "advanced position") with respect to the main body cover 30 which is the housing of the main body 3, the cleansing nozzle 6 sprays water from the water source toward the body of the user to perform genital and anal cleansing.

FIG. 1 illustrates a state in which the cleansing nozzle 6 is in the advanced position. The cleansing nozzle 6 may also be shared for cleansing the inside of the toilet bowl 7 (bowl unit 8 or the like). The cleansing nozzle 6 may be used so as to be switchable between a genital/anal cleansing mode for performing genital and anal cleansing of the user and a toilet bowl cleansing mode for spraying water in the toilet bowl 7. For example, the cleansing nozzle 6 may be used so as to be switchable between the genital/anal cleansing mode and the toilet bowl cleansing mode under the control of a control device 34 (refer to FIG. 4) of the toilet seat apparatus 2.

The operation device 10 is installed in the toilet room R. The operation device 10 is installed at a position where the user can operate the device. The operation device 10 is installed at a position where the user can operate the device when the user is seated on the toilet seat 5. In the example illustrated in FIG. 1, the operation device 10 is disposed on a wall surface W on the right side when viewed from the user seated on the toilet seat 5. The operation device 10 is not limited to the wall surface and may be disposed in various modes as long as the device can be used by the user seated on the toilet seat 5. For example, the operation device 10 may be provided integrally with the toilet seat apparatus 2.

The operation device 10 is communicably connected to the toilet seat apparatus 2 via a predetermined network (for example, a network N in FIG. 11) by wired or wireless connection. For example, the toilet seat apparatus 2 and the operation device 10 may be connected in any manner as long as transmission and reception of information is possible, and thus, may be communicably connected by wired or wireless connection.

The operation device 10 receives various operations from the user via a display surface (for example, a display screen 11) by the touch panel function, for example. Furthermore, the operation device 10 may include switches and buttons, and may receive various operations by the switches and buttons. The display screen 11 is a display screen of a tablet terminal or the like actualized by a liquid crystal display or an organic Electro-Luminescence (EL) display, for example, and is a display device for displaying various types of information. That is, the operation device 10 performs reception of input from the user as well as outputting information to the user by using the display screen 11. The display screen 11 is a display device that displays various types of information.

The operation device 10 receives a user's operation for stopping the control being executed by the toilet seat apparatus 2. The operation device 10 receives a user's operation for starting the execution of genital/anal cleansing by the toilet seat apparatus 2. The operation device 10 receives an instruction from the user to the cleansing nozzle 6. The operation device 10 receives a user's operation for allowing the toilet seat apparatus 2 to output a predetermined sound. The operation device 10 receives a user's operation for performing a sterilization process for sterilizing the cleansing nozzle 6 (refer to FIG. 1) of the toilet seat apparatus 2 with sterilizing water. The operation device 10 receives a user's operation for adjusting the momentum of water discharge during genital/anal cleansing performed by the toilet seat apparatus 2. The operation device 10 receives a user's operation for adjusting the volume of the sound output by the toilet seat apparatus 2. The operation device 10 receives a user's operation for selecting a language for displaying information regarding the use of the toilet on the operation device 10 and outputting voice.

For example, the operation device 10 may display an object that receives the above-described user's operation on the display screen 11 and may execute various processes in response to the user's contact with the displayed object. For example, the operation device 10 may include switches, buttons, or the like that receive the above-described user operations, and may execute various processes in response to the user's contact with the switches, buttons, or the like. The above is an example, and the operation device 10 may receive operations by a user who executes various processes.

The toilet system 1 detects various properties such as the shape, size, quality, and color of the user's excrement (feces) by various configurations and treatments described below. The toilet system 1 detects the user's defecation by an optical method. That is, the toilet system 1 is a toilet system capable of detecting excrement (feces) information by an optical means. For example, the toilet system 1 enters the standby mode, which will be described below by personal authentication after the user sits on the toilet seat 5 or operation of the operation device 10, and automatically enters the measurement mode by excretion of the user. The toilet system 1 may provide information to a terminal device such as a user's smartphone based on the measurement result.

<2. Configuration of Toilet Seat Apparatus>

Figure 2:
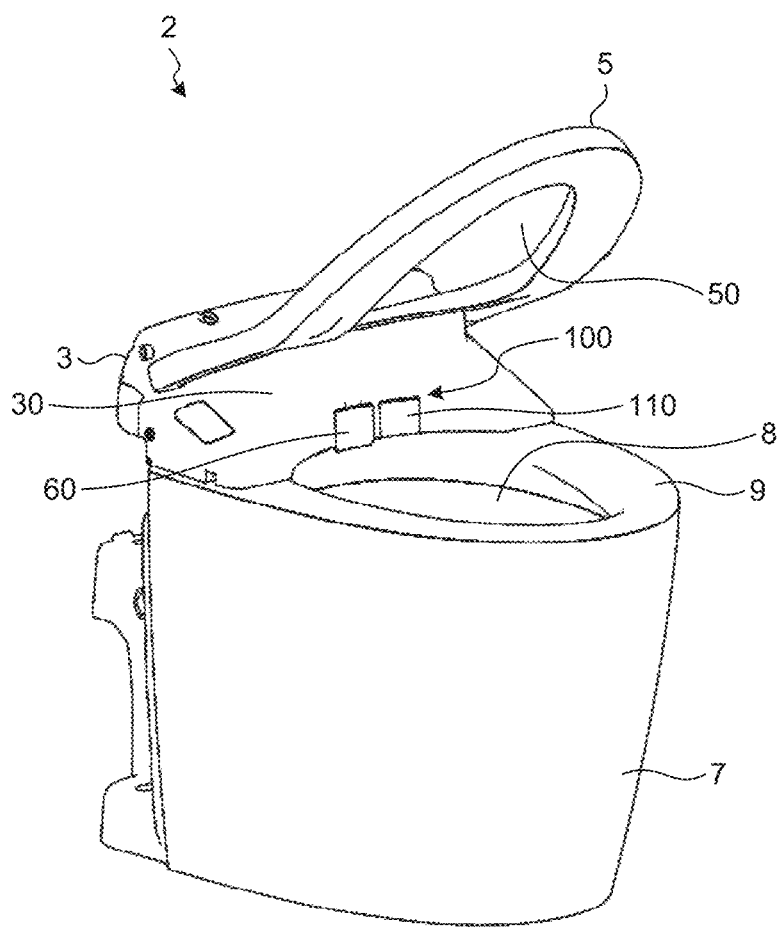
FIG. 2 is a perspective view illustrating an example of the configuration of the toilet seat apparatus according to the first embodiment.
Figure 3:
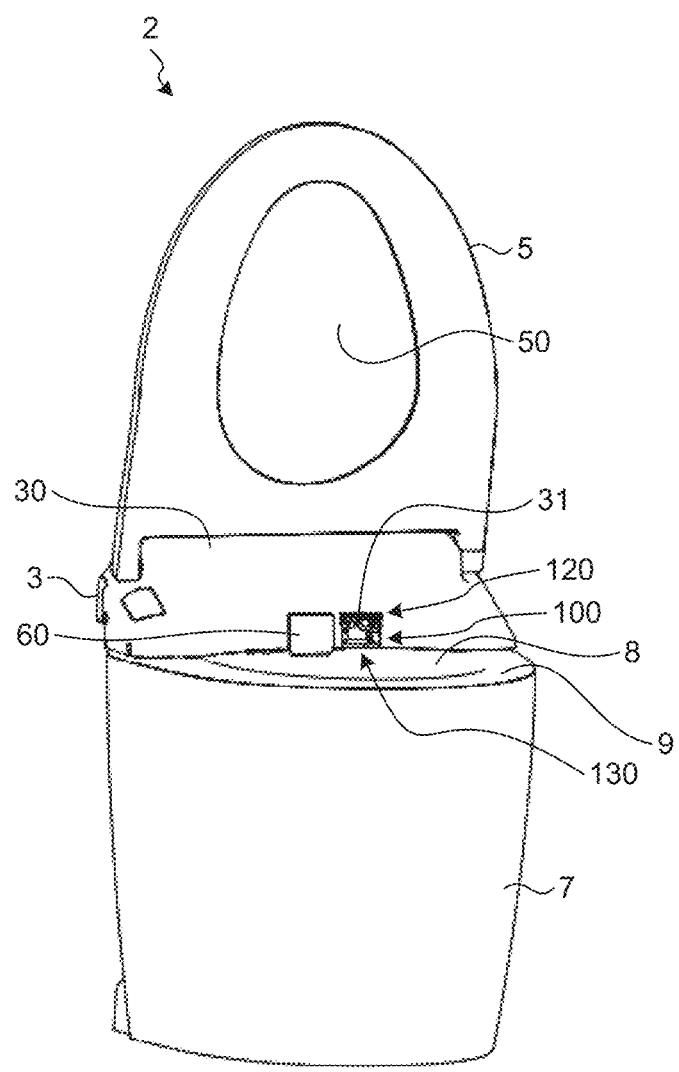
FIG. 3 is a perspective view illustrating an example of the configuration of the toilet seat apparatus according to the first embodiment.

Next, a configuration of the toilet seat apparatus 2 will be described with reference to FIGS. 2 and 3. FIGS. 2 and 3 are perspective views illustrating an example of the configuration of the toilet seat apparatus according to the first embodiment. Specifically, FIG. 2 is a view illustrating a case where a lid 110 of the optical unit 100 is in a state of being closed (hereinafter, also referred to as a "closed state"). Furthermore, FIG. 3 is a view illustrating a state in which the lid 110 of the optical unit 100 is removed.

Figure 5:
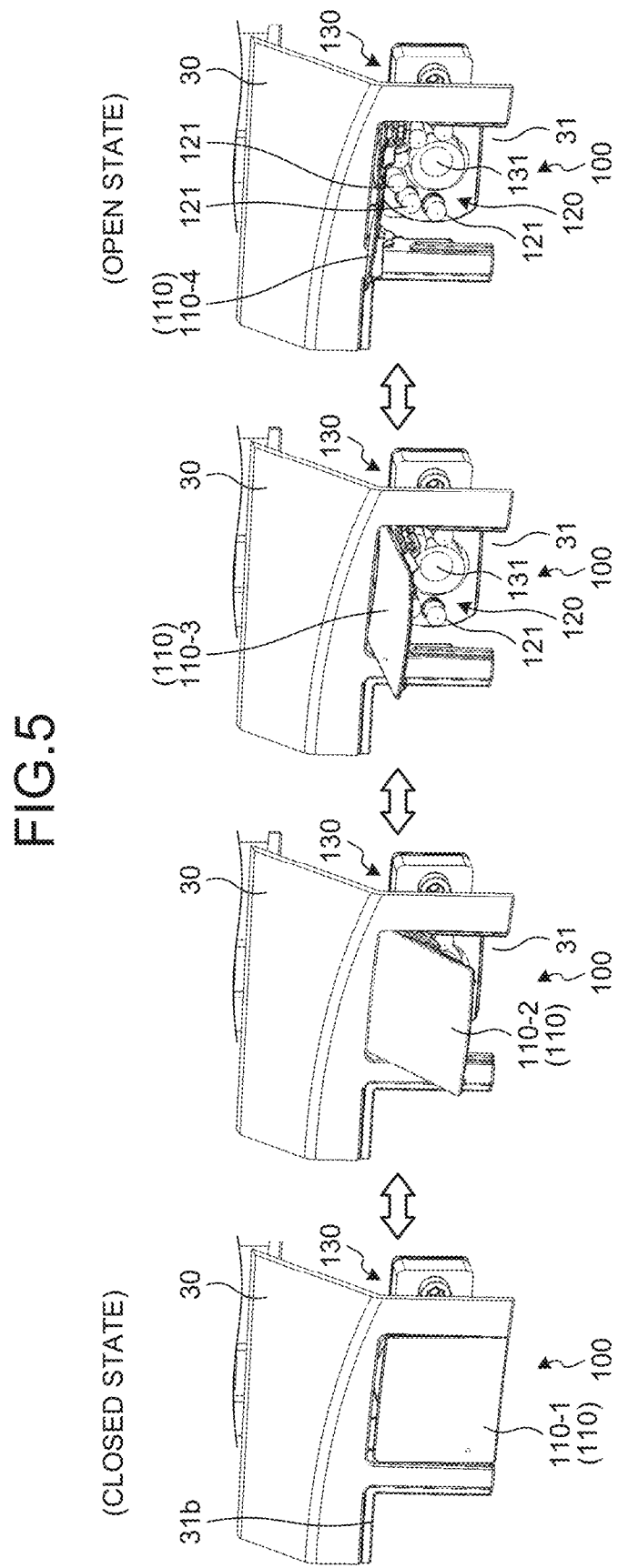
FIG. 5 is a diagram illustrating an example of an opening/closing operation of a lid.

As illustrated in FIG. 2, when the lid 110 is in the closed state, the components other than the lid 110 of the optical unit 100 (light emitting unit 120, light receiving unit 130, or the like in FIGS. 3 and 5) are hidden behind the lid 110. The closed state here is a term indicating a state in which the light receiving unit 130 is not exposed to water by the lid 110, and includes a configuration in which a portion where the light receiving unit 130 is not exposed to water is opened. In the closed state of the lid 110, the lid 110 is located in front of the light emitting unit 120 and the light receiving unit 130. In this manner, the lid 110 is located in front of the light receiving unit 130 in the closed state. That is, in the closed state of the lid 110, the lid 110 is located in a direction toward the inside of the toilet bowl 7 from the light emitting unit 120 and the light receiving unit 130. With this configuration, in the closed state of the lid 110, the light emitting unit 120 and the light receiving unit 130 are covered by the main body cover 30 and the lid 110. The light emitting unit 120 and the light receiving unit 130 are disposed with respect to the main body cover 30 which is a housing. Although the example of FIG. 2 is a case where the lid 110 is formed of material having no or low transparency similarly to the main body cover 30, the lid 110 may be formed of a material different from the main body cover 30. For example, the lid 110 (or a part thereof) may be formed of a transparent material, which will be described below in details.

Furthermore, FIG. 2 illustrates a state in which the cleansing nozzle 6 (refer to FIG. 1) is housed in the main body cover 30 (hereinafter, also referred to as "storage position"). As illustrated in FIG. 2, when the cleansing nozzle 6 is in the storage position, a nozzle lid 60 is closed and the cleansing nozzle 6 is hidden behind the nozzle lid 60. When cleansing is performed by the cleansing nozzle 6, the nozzle lid 60 is opened, and the cleansing nozzle 6 protrudes from an opening 31b (refer to FIG. 5) of the main body cover 30, allowing the cleansing nozzle 6 to shift to an advancing state.

As illustrated in FIG. 3, when the lid 110 is removed, the light emitting unit 120 and the light receiving unit 130 of the optical unit 100 are exposed from an opening 31 of the main body cover 30. For example, when the lid 110 is open (hereinafter, also referred to as "open state"), the lid 110 is not located in front of the light emitting unit 120 and the light receiving unit 130 as illustrated in FIG. 3. With this configuration, the light emitting unit 120 and the light receiving unit 130 are exposed when the lid 110 is in the open state. When the lid 110 is in the open state, the light emitting unit 120 can emit light toward the excrement in the toilet bowl 7, and the light receiving unit 130 can receive the reflected light from the excrement in the toilet bowl 7. As described above, the lid 110 in the closed state covers the front of the light receiving unit 130 by being located in front of the light receiving unit 130, while the lid 110 in the open state uncovers the front of the light receiving unit 130 by being not located in front of the light receiving unit 130. The lid 110 is openable and closable with respect to the light receiving unit 130 between a position that covers the front of the light receiving unit 130 and a position that uncovers the front of the light receiving unit 130. The details of the open state of the lid 110 will be described below.

As illustrated in FIGS. 2 and 3, the toilet seat apparatus 2 has a configuration in which the optical unit 100 is disposed at a position adjacent to the cleansing nozzle 6. Not limited to the position adjacent to the cleansing nozzle 6, the optical unit 100 may be disposed at various positions, which will be described below.

<3. Functional Configuration of Toilet Seat Apparatus>

Figure 4:
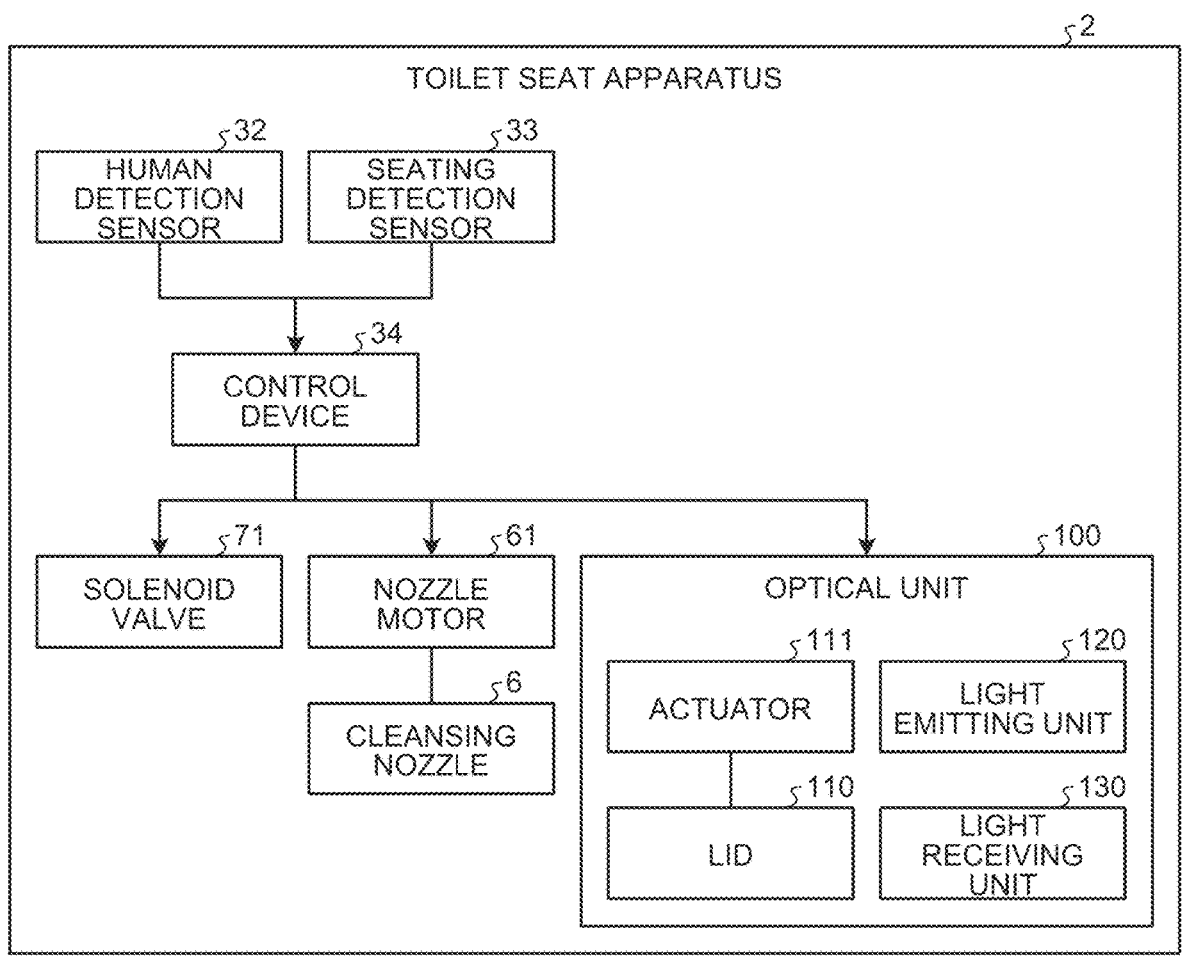
FIG. 4 is a block diagram illustrating an example of a functional configuration of the toilet seat apparatus according to the first embodiment.

Next, a functional configuration of the toilet seat apparatus 2 will be described with reference to FIG. 4. FIG. 4 is a block diagram illustrating an example of a functional configuration of the toilet seat apparatus according to the first embodiment. As illustrated in FIG. 4, the toilet seat apparatus 2 includes a human detection sensor 32, a seating detection sensor 33, a control device 34, a solenoid valve 71, a nozzle motor 61, a cleansing nozzle 6, and an optical unit 100. Note that FIG. 4 omits illustrations of a part (main body 3, toilet seat 5, toilet bowl 7, etc.) of the configuration of the toilet seat apparatus 2 described in FIG. 1.

For example, the human detection sensor 32, the seating detection sensor 33, and the control device 34 are provided in the main body 3 of the toilet seat apparatus 2. Although not illustrated, the toilet seat apparatus 2 includes a communication device (for example, a communication device 35 in FIG. 11) that communicates with the operation device 10. For example, a communication device is actualized by a communication circuit or the like. Then, the communication device is connected to a predetermined network (for example, the network N in FIG. 11) by wired or wireless connection, and transmits/receives information to/from an information processing device such as the operation device 10. Furthermore, the main body 3 may have a storage unit (second memory 20 or the like in FIG. 18) outside the control device 34. In this case, the toilet seat apparatus 2 may transmit data from the control device 34 to the second memory 20 and store the data in the second memory 20, the details of which will be described below.

The human detection sensor 32 has a function of detecting human. For example, the human detection sensor 32 is actualized by a pyroelectric sensor or the like using an infrared signal. For example, the human detection sensor 32 may be actualized by a microwave (μ-wave) sensor or the like. The above is an example, and the human detection sensor 32 is not limited to the above, and may detect the human by various means. For example, the human detection sensor 32 detects a person (user, etc.) who has entered the toilet room R (refer to FIG. 1). The human detection sensor 32 outputs a detection signal to the control device 34.

The seating detection sensor 33 has a function of detecting the seating of a person on the toilet seat apparatus 2. The seating detection sensor 33 detects that the user is seated on the toilet seat 5. The seating detection sensor 33 can detect the seating of the user on the toilet seat 5. The seating detection sensor 33 also functions as a seat leave detection sensor that detects the user's leave from the toilet seat 5. The seating detection sensor 33 detects the user's seated state with respect to the toilet seat 5.

For example, the seating detection sensor 33 detects that the user is seated on the toilet seat 5 by a load sensor. For example, the seating detection sensor 33 may be an infrared light emission-reception type ranging sensor that detects a human existing near the toilet seat 5 immediately before a person (user) sits on the toilet seat 5 or a user seated on the toilet seat 5. The above is an example, and the seating detection sensor 33 is not limited to the above, and may detect the seating of a person on the toilet seat apparatus 2 by various means. The seating detection sensor 33 outputs a seating detection signal to the control device 34.

The control device 34 functions as a control unit that controls various configurations and processes. The control device 34 controls the nozzle motor 61, the solenoid valve 71, and the optical unit 100. The control device 34 controls the nozzle motor 61, the solenoid valve 71, and the optical unit 100 based on a signal transmitted from the operation device 10. The control device 34 controls the nozzle motor 61 based on the signal of the control instruction regarding the genital/anal cleansing transmitted from the operation device 10. The control device 34 controls the nozzle motor 61 in order to allow the cleansing nozzle 6 to perform advance/retract movement. The control device 34 controls the opening/closing of the solenoid valve 71. The control device 34 controls the optical unit 100 to opening/closing operation of the lid 110. The control device 34 transmits control information for setting the lid 110 in an open state, to the optical unit 100. The control device 34 transmits control information for setting the lid 110 in a closed state, to the optical unit 100. The control device 34 transmits control information for controlling the turning of/off of the light emitting unit 120 to the optical unit 100. The control device 34 controls the lid 110 to the closed state at a timing when light reception by the light receiving unit 130 is not needed, such as before seating of the user or after acquisition of sufficient data.

The control device 34 transmits control information for controlling the function of an electronic shutter of the light receiving unit 130 to the optical unit 100. Unlike a mechanical shutter such as a lens shutter, the electronic shutter of the light receiving unit 130 uses a shutter method in which a light receiving element 132 (imaging element) is electronically controlled to read out the exposure. That is, the electronic shutter of the light receiving unit 130 is an electronically driven shutter or an electronically controlled shutter. The control device 34 transmits control information to the nozzle motor 61, the solenoid valve 71, and the optical unit 100 by wired communication. The control device 34 may transmit control information to the nozzle motor 61, the solenoid valve 71, and the optical unit 100 using wireless communication.

The control device 34 controls the opening/closing operation of the lid 110. The control device 34 opens the lid 110 after the seating of the user detected by the seating detection sensor 33, and closes the lid 110 before detection of the user's seat leave by the seating detection sensor 33. The control device 34 closes the lid 110 based on the reception of the reflected light from the excrement by the light receiving unit 130.

The control device 34 closes the lid 110 in conjunction with an instruction from the user to operate the cleansing nozzle 6 to the operation device 10. The control device 34 closes the lid 110 based on the reception of the reflected light from the cleansing nozzle 6 that has advanced to the bowl unit 8, by the light receiving unit 130.

The control device 34 opens the lid 110 so that the central axis of the light emitted by the light emitting unit 120 and the lid 110 do not overlap each other during the control of opening the lid 110. The control device 34 controls the lid 110 at a position not intersecting the central axis of the light emitted by the light emitting unit 120 in the open state of the lid 110. The control device 34 controls the lid 110 outside the half-power angle region of the light emitted by the light emitting unit 120 in the open state of the lid 110. The control device 34 controls the light emitting unit 120 so as to simultaneously emit light of the same wavelength. For example, the control device 34 opens the lid 110 by assuming that the position closer to the closed position than the state in which the lid 110 is completely open (fully open state) is an open state. For example, the control device 34 opens the lid 110 by assuming that the state in which the lid 110 is located outside the region of the half-power angle of each of the light emitting elements 121 and the lid 110 is at a position in front of the fully open state, is the open state.

The control device 34 closes the lid 110 in conjunction with the operation of the cleansing nozzle 6. The control device 34 controls the lid 110 starting from the user's operation on the operation device 10 that controls the cleansing nozzle 6. The control device 34 detects the operation of the cleansing nozzle 6 (advancing operation of the nozzle to the bowl unit) and controls the lid 110.

The control device 34 controls the lid 110 so as to open upward when placed on the toilet bowl 7. The control device 34 controls the lid 110 to the closed state at the time of operation of the cleansing nozzle 6. The control device 34 controls the lid 110 to the closed state at the time of operation of the cleansing nozzle 6 provided on the toilet bowl 7.

During the period in which user's seating on the toilet seat 5 is detected by the seating detection sensor 33, the control device 34 has modes including: a measurement mode of emitting light having a wavelength in the visible light region: and a measurement standby mode (standby mode) of emitting light having a wavelength in the invisible light region or light having a wavelength closer to the invisible light region compared to the wavelength of the light emitted in the measurement mode. In this case, the control device 34 switches the operation mode by switching between the measurement mode and the standby mode. The control device 34 executes the standby mode until the light receiving unit 130 receives the reflected light from the feces, and executes the measurement mode based on the reception of the reflected light from the feces by the light receiving unit 130.

The control device 34 controls the emission of light performed by the light emitting unit 120. The control device 34 controls energization of the light emitting element 121 and application of a voltage to the light receiving element 132. The control device 34 performs light reception control including transmitting a control instruction to open the electronic shutter to the light receiving element 132 and energizing the light emitting element 121 so as to permit reception of the reflected light from the feces.

The control device 34 performs control to set an interval from a start of execution of one light reception control to execution of light reception control subsequent to the one light reception control, to 0.2 milliseconds or more. The control device 34 performs control to set the interval from a start of execution of one light reception control to the execution of the subsequent light reception control to 10 milliseconds or less. In one light reception control, the control device 34 energizes only one light emitting element 121 among the plurality of light emitting elements 121. Every time the one light reception control is completed, the control device 34 changes the light emitting element 121 to be energized in the subsequent light reception control. The control device 34 performs control to set the interval from the start of execution of the one light reception control to the execution of the subsequent light reception control to 1.6 milliseconds or less. In the light reception control, the control device 34 sets the energization time length for each of the light emitting elements 121 to different time lengths depending on the wavelength emitted by each of the light emitting elements 121.

Furthermore, the control device 34 controls the toilet lid 4 and the toilet seat 5 as illustrated in FIG. 1. The control device 34 controls the toilet lid 4 and the toilet seat 5 based on the signal transmitted from the operation device 10. The control device 34 controls the toilet lid 4 based on the signal of the control instruction regarding the opening/closing of the toilet lid transmitted from the operation device 10. The control device 34 controls the toilet seat 5 based on a control instruction signal related to opening/closing of the seating portion transmitted from the operation device 10. The control device 34 transmits control information to the toilet lid 4 and the toilet seat 5 by wired communication. The control device 34 may transmit control information to the toilet lid 4 and the toilet seat 5 by wireless communication.

The control device 34 determines whether the entry of the user into the room is detected by the human detection sensor 32. The control device 34 determines whether the user's entry into the toilet room R is detected by the human detection sensor 32. The control device 34 determines whether the seating of the user is detected by the seating detection sensor 33. The control device 34 determines whether the seating of the user on the toilet seat 5 is detected by the seating detection sensor 33. The control device 34 has various configurations such as an arithmetic processing device 342 (refer to FIG. 18) that executes arithmetic operations related to the above-described control, a storage unit, or the like. For example, the arithmetic processing device 342 is actualized by various means including a processor such as a Central Processing Unit (CPU), Micro Processing Unit (MPU), and an Application Specific Integrated Circuit (ASIC), or an integrated circuit such as a Field Programmable Gate Array (FPGA). Details of the configuration of the control device 34 will be described below.

The solenoid valve 71 has a function of a valve that controls the flow of fluid by an electromagnetic method. The solenoid valve 71 switches between supplying and stopping tap water from a water supply pipe, for example. The solenoid valve 71 executes opening/closing control in response to an instruction from the control device 34.

The nozzle motor 61 is a drive source (motor) that drives the cleansing nozzle 6 to perform advance/retract movement. The nozzle motor 61 executes control to allow the cleansing nozzle 6 to perform advance/retract movement with respect to the main body cover 30 of the main body 3. The nozzle motor 61 executes control to allow the cleansing nozzle 6 to perform advance/retract movement in response to an instruction from the control device 34.

The optical unit 100 includes the lid 110, an actuator 111, the light emitting unit 120, and the light receiving unit 130. The optical unit 100 functions as an excrement detection apparatus (excrement measurement device). The optical unit that functions as the excrement detection apparatus may be separate from the toilet seat apparatus, which will be described below.

The lid 110 can be located in front of the light emitting unit 120 and the light receiving unit 130, and functions as a lid. The lid 110 can be located on the side (front) facing the light emitting surface of the light emitting unit 120. The lid 110 can be located on the side (front) facing the light receiving surface of the light receiving unit 130. The lid 110 is preferably formed of a non-transparent material in order to achieve a configuration that reduces the possibility to visually reveal the optical unit 100 and that takes privacy of the user in consideration. For example, the lid 110 may be formed in a non-transparent state by coloring. A non-transparent material (paint) may be applied to the surface of the lid 110. Note that the lid 110 is not limited to a non-transparent configuration, and may be transparent. The lid 110 is provided in front of the light receiving unit 130 and is openable/closable. The lid 110 can transition between an open state and a closed state by the actuator 111, so as to be located in front of the light emitting unit 120 and the light receiving unit 130, or expose the light emitting unit 120 and the light receiving unit 130. The lid 110 is set to the closed state at a timing when the light receiving unit 130 does not need to receive light, such as before seating of the user or after acquisition of sufficient data. With this configuration, the lid 110 can suppress a deterioration in detection accuracy of the light receiving unit 130 due to contamination.

In the open state, the lid 110 does not intersect the central axis of the light emitted by the light emitting unit 120. In the open state, the lid 110 is located outside the half-power angle region of the light emitted by the light emitting unit 120. The lid 110 opens upward when placed on the toilet bowl 7. The lid 110 is in the closed state at the time of operation of the cleansing nozzle 6. The lid 110 is in a closed state at the time of operation of the cleansing nozzle 6 provided on the toilet bowl 7.

The actuator 111 is a drive source (motor) that sets the lid 110 to the open state or the closed state. The actuator 111 executes control of setting the lid 110 to the open state or the closed state in response to an instruction from the control device 34. The actuator 111 sets the lid 110 to the closed state at a timing when the light receiving unit 130 does not need to receive light, such as before seating of the user or after acquisition of sufficient data.

In the open state of the lid 110, the actuator 111 fixes the lid 110 at a position not intersecting the central axis of the light emitted by the light emitting unit 120. In the open state of the lid 110, the actuator 111 fixes the position of the lid 110 outside the half-power angle region of the light emitted by the light emitting unit 120. The actuator 111 opens the lid 110 upward when placed on the toilet bowl 7. The actuator 111 sets the lid 110 to the closed state at the time of operation of the cleansing nozzle 6. The actuator 111 sets the lid 110 to the closed state at the time of operation of the cleansing nozzle 6 provided on the toilet bowl 7.

The light emitting unit 120 emits light. The light emitting unit 120 includes a light emitting element 121 (refer to FIG. 5) that emits light. The light emitting unit 120 emits light toward the excrement discharged by the user. The light emitting unit 120 emits light toward the feces discharged by the user. The light emitting unit 120 emits light toward the falling feces.

The light emitting unit 120 includes the light emitting element 121 that emits light. The light emitting unit 120 includes the light emitting element 121 that emits light in the front direction. The light emitting unit 120 includes the light emitting element 121 that emits light in the front direction toward the excrement discharged by the user.

The light emitting unit 120 emits light in the front direction. The light emitting unit 120 is arranged so that the central axis of the light emitting unit 120 is parallel to the central axis of the light receiving unit 130 or is inclined in a direction approaching the central axis of the light receiving unit 130 on the front side. Here, the central axis of the light receiving unit 130 is a line that passes through the center of a lens 131 and intersects the lens 131 perpendicularly. The light emitting unit 120 is arranged so that the direction of the central axis of the light emitting unit 120 is inclined diagonally with respect to the central axis of the light receiving unit 130. The central axis of the light receiving unit 130 may be a central axis extending in a thickness direction of the lens 131 of the light receiving unit 130 and passing through the center of the lens 131, for example. When the light receiving unit 130 does not have the lens 131, the central axis of the light receiving unit 130 may be a central axis extending in the thickness direction of the light receiving element 132 of the light receiving unit 130 and passing through the center of the light receiving element 132, for example. The light emitting unit 120 is arranged so that the direction of the central axis of each of the light emitting elements 121 is inclined diagonally with respect to the central axis of the light receiving element 132. The light emitting unit 120 emits light in the front direction toward the feces discharged by the user.

The light emitting unit 120 includes a plurality of light emitting elements 121. The light emitting unit 120 includes a plurality of light emitting elements 121 each of which emits light. The light emitting unit 120 includes a plurality of light emitting elements 121 each of which emits light having the same wavelength. The light emitting unit 120 emits light toward the falling feces discharged by the user. The light emitting unit 120 includes a plurality of light emitting elements 121 for emitting beams of light having different wavelengths. Each of the light emitting elements 121 is arranged so that the direction of the central axis is inclined diagonally with respect to the central axis of the light receiving element 132.

The light emitting element 121 is arranged in parallel with the light receiving unit 130 or in front of the light receiving unit 130 in the side view or the top view of the main body cover 30 which is a housing. The light emitting element 121 is arranged in parallel with the lens 131 or in front of the lens 131 in a side view or a top view of the main body cover 30 which is a housing.

There is provided, around the light emitting element 121, a reflecting means of giving forward unidirectionality to the light emitted by the light emitting element 121. The reflecting means may be an inclined surface formed by an inclined member, or a recessed surface (outer surface of a recess) formed around the light emitting element 121. The plurality of light emitting elements 121 can each emit light having different wavelengths. The plurality of light emitting elements 121 is arranged so that the half-power angle regions of light emitted by them overlap each other within the opening 50 of the toilet seat 5 in a plan view of the toilet seat 5. The plurality of light emitting elements 121 is arranged so that the half-power angle regions of the light emitted by the plurality of light emitting elements 121 overlap each other toward the virtual falling position of the feces discharged from the user.

The plurality of light emitting elements 121 is arranged around the light receiving unit 130. The light emitting element 121 used in the standby mode is arranged above the light emitting element 121 used only in the measurement mode when placed on the toilet bowl 7. The number of light emitting elements 121 used in the standby mode is smaller than the number of light emitting elements 121 used in the measurement mode. The plurality of light emitting elements 121 is arranged above the light receiving unit 130 when placed on the toilet bowl 7. Details of the configuration of the light emitting unit 120 and the light emitting element 121 will be described below.

The light receiving unit 130 receives light. The light receiving unit 130 includes the lens 131 (refer to FIG. 5) and the light receiving element 132 (refer to FIG. 13) that receives light. The light receiving unit 130 receives the reflected light from the excrement corresponding to the light emitted by the light emitting unit 120. The light receiving unit 130 receives the reflected light from the feces corresponding to the light emitted by the light emitting unit 120. The light receiving unit 130 receives the reflected light from the falling feces corresponding to the light emitted by the light emitting unit 120.

The light receiving unit 130 includes the light receiving element 132 that receives light. The light receiving unit 130 includes the lens 131 for condensing light in front of the light receiving element 132. There is provided, around the light receiving element 132, a case 133, which is a cover for suppressing the incident light from directions other than the front of the light receiving element 132. There is provided, around the light receiving element 132, the case 133 which is a cover for suppressing the incidence of light other than the light passing through the lens 131 arranged in front, onto the light receiving element 132. There is provided, around the light receiving element 132, the case 133, which is a cover for suppressing the incident light in side directions of the light receiving element 132.

The case 133 functions as a light incidence suppression cover that blocks or attenuates light from other than the front of the light receiving element 132. The case 133 is colored in a color that would not easily transmit light, such as black. The case 133 may be formed by using various materials such as resin as long as it can be formed into a desired shape. The light receiving unit 130 receives the reflected light from the feces corresponding to the light emitted by the light emitting unit 120. The light receiving unit 130 receives the reflected light from the falling feces corresponding to the light emitted by the light emitting unit 120. The light receiving unit 130 receives the reflected light from the feces corresponding to the light emitted by the light emitting unit 120. Details of the configuration of the light receiving unit 130 will be described below.

<4. Opening/Closing of the Lid>

Here, opening/closing of the lid 110 of the optical unit 100 will be described with reference to FIG. 5. FIG. 5 is a diagram illustrating an example of an opening/closing operation of the lid. Specifically, FIG. 5 is a diagram illustrating an example of an operation in which the lid 110 transitions between an open state and a closed state. The lid 110 transitions between the open state and the closed state by the drive of the actuator 111. While the lid 110 will be described as lids 110-1 to 110-4 in FIG. 5 depending on the position of the lid 110, the lid 110 will be simply referred to as the "lid 110" other than a case where distinction is needed in description. Furthermore, in order to demonstrate the opening/closing of the lid 110, FIG. 5 illustrates only a part of the main body cover 30, and omits illustrations of the nozzle lid 60 covering the opening 31b for the cleansing nozzle 6, or the like. As illustrated in FIG. 5, the main body cover 30 includes two openings, an opening 31 for the optical unit 100 and an opening 31b for the cleansing nozzle 6. The opening 31 for the optical unit 100 can be covered by the lid 110. Furthermore, the opening 31b for the cleansing nozzle 6 can be covered with the nozzle lid 60. For example, the opening 31b is provided in the central portion on the rear side of the toilet bowl 7, while the opening 31 is provided at a position adjacent to the opening 31b.

The lid 110-1 illustrated in FIG. 5 indicates the lid 110 in a closed state. The lid 110-1 in the closed state is located in front of the light emitting unit 120 and the light receiving unit 130. Substantially flush with the main body cover 30, the lid 110-1 covers the front of the light emitting unit 120 and the light receiving unit 130. In this manner, the main body cover 30, which is the housing, is located in front of the light emitting unit 120 and the light receiving unit 130.

The lid 110 is located at the position of the lid 110-1 which is in the closed state at timings such as before the user of the toilet room R is seated on the toilet seat 5, at the time of operation of the cleansing nozzle 6, or after completion of the detection of defecation. With this configuration, the lid 110 suppresses the exposure of the light emitting unit 120 and the light receiving unit 130. This makes it possible to suppress the situations in which the light emitting unit 120 and the light receiving unit 130 are visually revealed to the user when entering the toilet room R, or water splashes to the light emitting unit 120 and the light receiving unit 130.

Under the control of the control device 34 onto the actuator 111, the lid 110 shifts to be at the position of the lid 110-1, in the closed state. Thereafter, the lid 110 transitions from the closed state to the open state under the control of the control device 34 onto the actuator 111. The lid 110 performs positional transition in the order of the lids 110-1, 110-2, 110-3, and 110-4, transitioning from the closed state to the open state. For example, the lid 110 transitions from the lid 110-1 in the closed state to the lid 110-4 in the open state at timings such as after the user of the toilet room R is seated on the toilet seat 5, or after completion of the operation of the cleansing nozzle 6.

The lid 110 performs opening/closing operation on the main body cover 30 with one end side adjacent to the upper end of the opening 31 of the main body cover 30, as an axis. The lid 110 performs rotational operation with one end side as an axis to move the position of the other end portion facing the one end portion from the bottom to the top. In this manner, in the example of FIG. 5, the lid 110 performs rotational operation with respect to the main body cover 30 to transition from the lid 110-1 in the closed state to the lid 110-4 in the open state.

The lids 110-2 and 110-3 indicate intermediate states in the middle of the transition from the lid 110-1 in the closed state to the lid 110-4 in the open state. With gradual upward movement of the other end of the lid 110 from the lid 110-1 to the lids 110-2, 110-3, and 110-4 in this manner, the light emitting unit 120 and the light receiving unit 130 are exposed. Specifically, when the other end of the lid 110 moves upward, the light emitting element 121 of the light emitting unit 120, the lens 131 of the light receiving unit 130, or the like are exposed from the opening 31 of the main body cover 30.

As described above, when the lid 110-4 in the open state is located at an upper position in front of the light emitting unit 120 and the light receiving unit 130, it is possible to suppress the influence of external light (lighting in the toilet room R, or the like) to the light emitting unit 120 and the light receiving unit 130 and suppress water splash or the like onto the light emitting unit 120 or the light receiving unit 130 from above.

Furthermore, the lid 110 transitions from the open state to the closed state under the control of the control device 34 onto the actuator 111. The transition from the open state to the closed state is a reverse operation of the transition from the closed state to the open state described above, and thus detailed description thereof will be omitted. The lid 110 transitions positions in order of the lids 110-4, 110-3, 110-2, and 110-1 to allow transition from the open state to the closed state. The lid 110 performs rotational operation with one end side as an axis to move the other end portion from the top to the bottom. For example, the lid 110 transitions from the lid 110-4 in the open state to the lid 110-1 in the closed state at timings such as after the user of the toilet room R leaves the toilet seat 5, at the time of the operation of the cleansing nozzle 6, or after completion of detection related to defecation.

In the example of FIG. 5, the lid 110 performs opening/closing operation with respect to the main body cover 30 with the one end side adjacent to the upper end of the opening 31 of the main body cover 30 as an axis, which is opening/closing operation in the vertical direction. The configuration of the lid 110, however, is not limited to the example in FIG. 5, and may be in various forms. For example, the lid 110 may be housed in a storage portion provided on the upper end side of the opening 31 of the main body cover 30. For example, the lid 110 may be configured like a shutter (blind or louver door) in which a number of elongated members are connected. Furthermore, for example, the lid 110 may perform opening/closing operation with respect to the main body cover 30 with the one end side adjacent to the lateral end of the opening 31 of the main body cover 30 as an axis so as to make opening/closing operation in the lateral direction. Furthermore, for example, the lid 110 can be separated into a plurality of parts, and is not limited to the one-sided opening configuration, but may be a double-opening configuration.

<5. Window>

Figure 6:
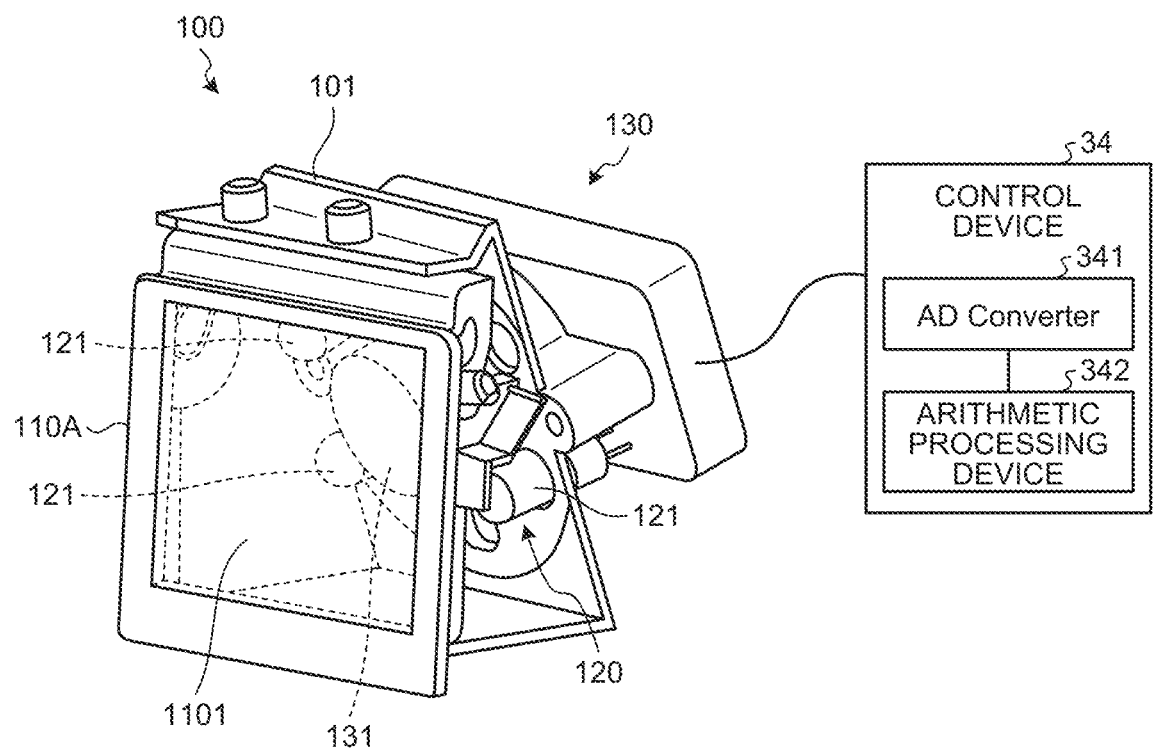
FIG. 6 is a diagram illustrating an example of an optical unit having a window.

Although the lid 110 is entirely formed of material having no (or low) transparency, a portion of the lid may be transparent. Details on this regard will be described below. FIG. 6 is a diagram illustrating an example of an optical unit having a window.

In the example of FIG. 6, the optical unit 100 includes a lid 110A having a window 1101 that has transparency to light, a light emitting unit 120 having a plurality of light emitting elements 121, and a light receiving unit 130. The lid 110A has the window 1101 inside a frame surrounding the periphery. The window 1101 may be formed of any material as long as it is transparent to the light emitted by the light emitting unit 120 and transparent to the light received by the light receiving unit 130. The light referred to here includes not only visible light but also invisible light such as infrared light.

In the example of FIG. 6, the light emitting unit 120 and the light receiving unit 130 of the optical unit 100 are disposed in a housing 101. In this manner, the light emitting unit 120 and the light receiving unit 130 are disposed inside the housing 101. Furthermore, the lid 110A is supported by the end of the housing 101 and is located in front of the light emitting unit 120 and the light receiving unit 130. In this manner, the end portion of the housing 101 is located in front of the light emitting unit 120 and the light receiving unit 130.

In the example of FIG. 6, the lid 110A is arranged so that the window 1101 is located in front of the light emitting unit 120 and the light receiving unit 130, enabling the optical unit 100 to detect defecation without performing the opening/closing operation of the lid 110A. The lid 110A may be fixed in position with respect to the housing 101, or may perform opening/closing operation with respect to the housing 101. Note that an AD Converter 341 of the control device 34 and an arithmetic processing device 342 will be described below.

<6. Other Device Configurations and Arrangement Examples>

The device configuration and arrangement of the optical units are not limited to the above, and may be various configurations and arrangements.

<6-1. Other Arrangement Examples of Optical Units>

Figure 7:
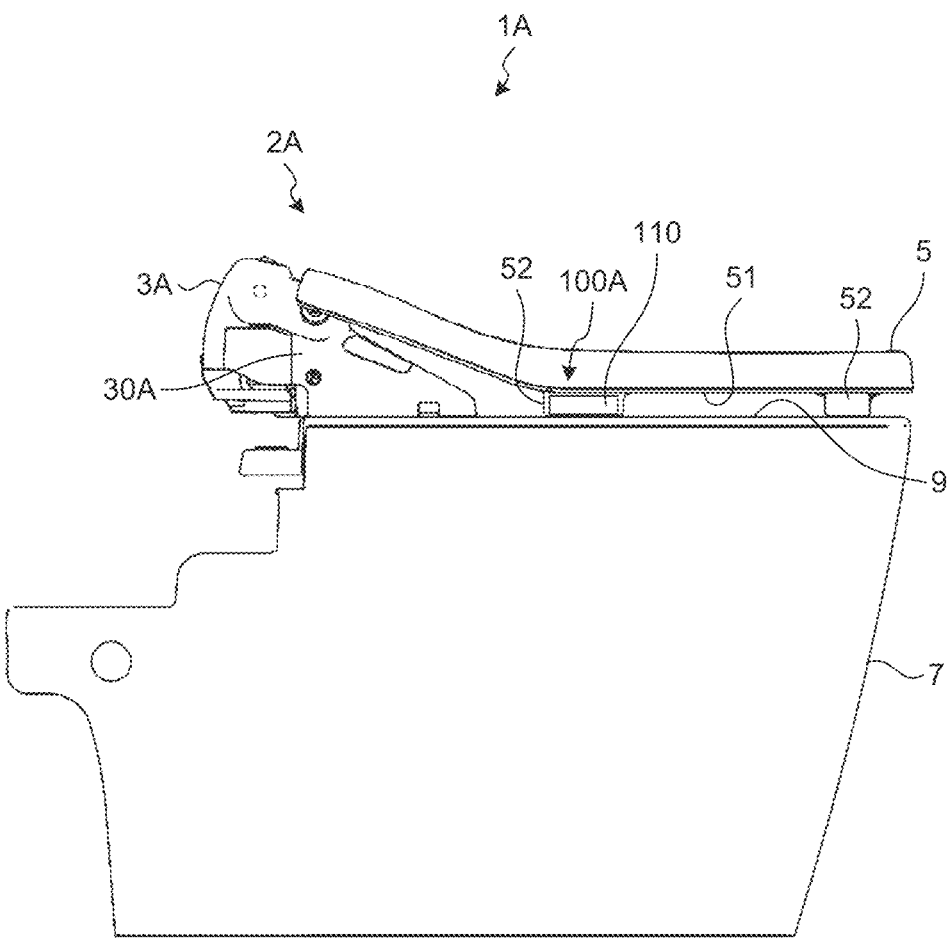
FIG. 7 is a side view illustrating an example of a configuration of a toilet system according to a second embodiment.
Figure 8:
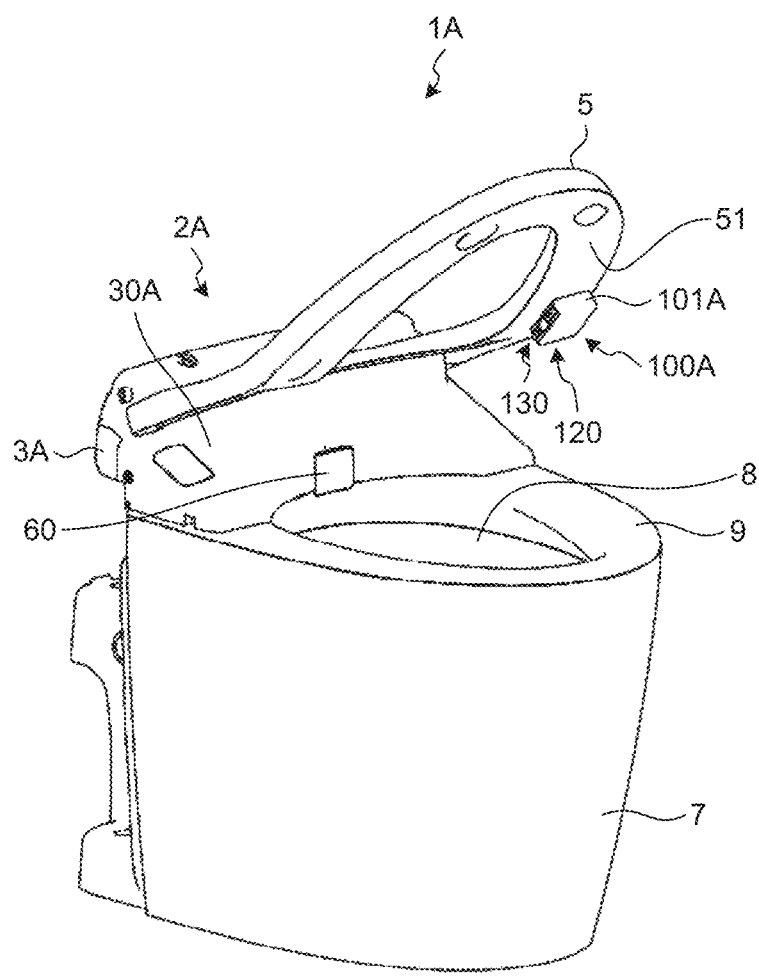
FIG. 8 is a perspective view illustrating an example of the configuration of the toilet system according to the second embodiment.

For example, the optical unit may be arranged not only in the main body cover 30 of the main body 3 but also at various positions. This point will be described with reference to FIGS. 7 and 8. FIG. 7 is a side view illustrating an example of a configuration of a toilet system according to a second embodiment. FIG. 8 is a perspective view illustrating an example of a configuration of the toilet system according to the second embodiment. Specifically, FIG. 7 is a view illustrating a case where the lid 110 of an optical unit 100A is in the closed state. Furthermore, FIG. 8 is a view illustrating a state in which the lid 110 of the optical unit 100A is removed. Description on the points similar to those of the toilet system 1 according to the first embodiment will be appropriately omitted by adding similar reference numerals.

A toilet system 1A includes a toilet seat apparatus 2A and an operation device 10 (not illustrated). In the toilet system 1A illustrated in FIGS. 7 and 8, only the configuration necessary for the explanation of the toilet seat apparatus 2A is illustrated, omitting the illustration of other configurations (operation device 10 or the like). The toilet seat apparatus 2A is provided in the toilet room R (refer to FIG. 1) similarly to the toilet seat apparatus 2. As illustrated in FIG. 8, the toilet seat apparatus 2A differs from the toilet seat apparatus 2 in that a main body cover 30A of a main body 3A does not have an opening 31 for the optical unit.

As illustrated in FIG. 7, in the toilet system 1A, the optical unit 100A is disposed between the rim 9 of the toilet bowl 7 of the toilet seat apparatus 2A and the toilet seat 5. Specifically, the optical unit 100A is disposed on a back surface 51 side, which is the opposite surface of the surface on which the user of the toilet seat 5 is seated. The optical unit 100A is arranged between the toilet seat 5 and the rim 9 in a direction in which the lid 110, the light emitting unit 120, and the light receiving unit 130 face the inside of the toilet bowl 7. In this manner, in the toilet seat apparatus 2A, by arranging the optical unit 100A on the back surface 51 side of the toilet seat 5, it is possible to reduce the possibility to visually reveal the optical unit 100A to the user of the toilet room R. The optical unit 100A may be disposed in a cushion portion 52 provided on the back surface 51 of the toilet seat 5.

The lid 110 is provided on one surface of a housing 101A (refer to FIG. 8) that accommodates configurations (light emitting unit 120, light receiving unit 130, etc. in FIG. 8) other than the lid 110 of the optical unit 100A. The lid 110 covers an opening surface of the housing 101A corresponding to the front side of the light emitting unit 120 and the light receiving unit 130. In the closed state of the lid 110, the light emitting unit 120, the light receiving unit 130, or the like are hidden behind the lid 110. In the closed state of the lid 110, the lid 110 is located in front of the light emitting unit 120 and the light receiving unit 130. That is, in the closed state of the lid 110, the lid 110 is located in a direction toward the inside of the toilet bowl 7 from the light emitting unit 120 and the light receiving unit 130. With this configuration, in the closed state of the lid 110, the light emitting unit 120 and the light receiving unit 130 are covered by the housing 101A and the lid 110. Although the example of FIG. 7 is a case where the lid 110 is formed of material having no or low transparency similarly to the housing 101A, the lid 110 may be formed of a material different from the housing 101A.

As illustrated in FIG. 8, when the lid 110 is removed, the light emitting unit 120 and the light receiving unit 130 of the optical unit 100A are exposed from the housing 101A. For example, when the lid 110 is in the open state, the lid 110 is not located in front of the light emitting unit 120 and the light receiving unit 130, as illustrated in FIG. 8. With this configuration, the light emitting unit 120 and the light receiving unit 130 are exposed when the lid 110 is in the open state. The opening/closing operation of the lid 110 with respect to the housing 101A is similar to the opening/closing operation of the lid 110 with respect to the main body cover 30, and the description thereof will be omitted. In the case of the toilet system 1A illustrated in FIGS. 7 and 8, the optical unit 100A is disposed outside the toilet seat apparatus 2A. Therefore, in the toilet system 1A, there is no need to modify the design in the toilet seat apparatus 2A in which various devices are arranged in a complicated and dense manner, and thus, the toilet system 1A is easy to fabricate compared to the configuration in which the optical unit is disposed within the toilet seat apparatus (for example, the toilet seat apparatus 2 of the toilet system 1).

<6-2. Other Device Configuration Examples>

Figure 9:
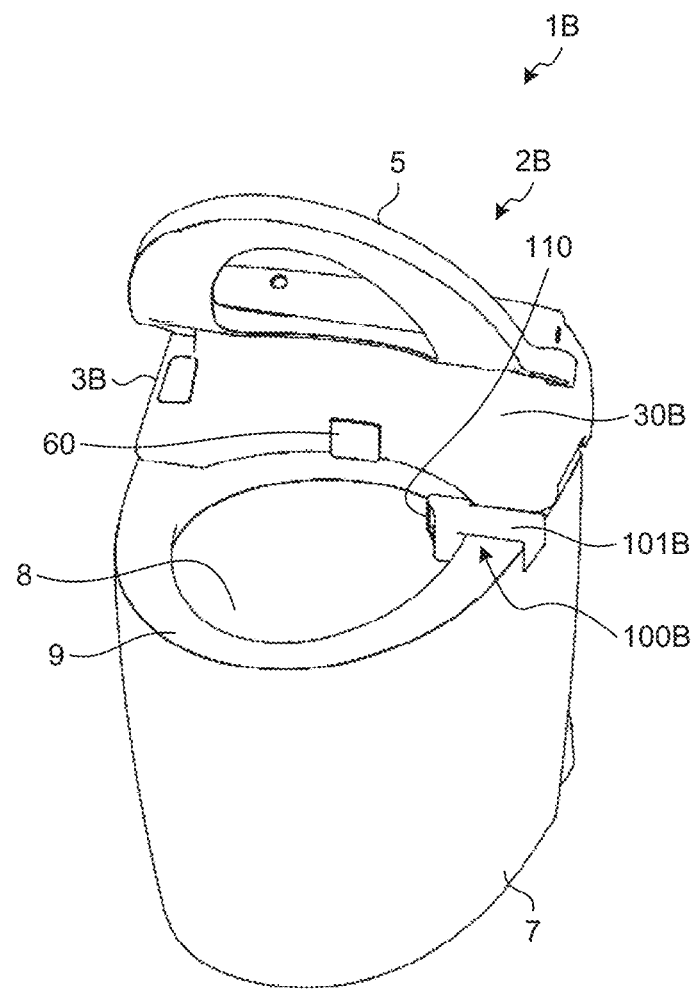
FIG. 9 is a perspective view illustrating an example of a configuration of a toilet system according to a third embodiment.
Figure 10:
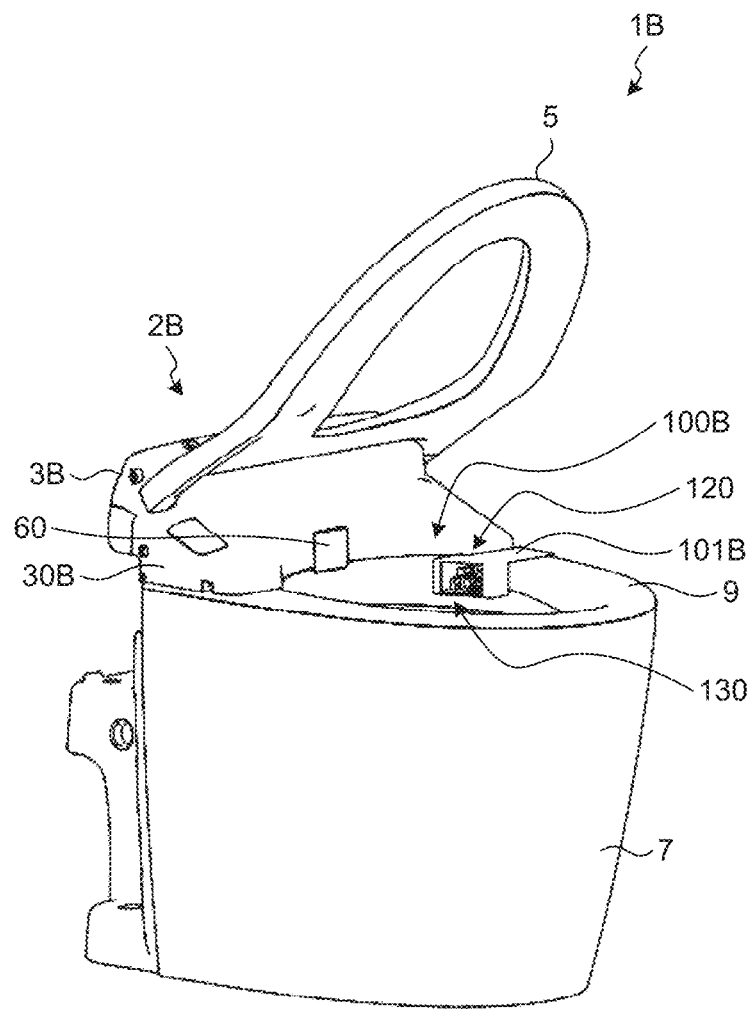
FIG. 10 is a perspective view illustrating an example of a configuration of the toilet system according to the third embodiment.

The toilet seat apparatus and the optical unit may be separate from each other. This point will be described with reference to FIGS. 9 to 11. First, a configuration of the toilet system will be described with reference to FIGS. 9 and 10. FIGS. 9 and 10 are perspective views illustrating an example of a configuration of the toilet system according to a third embodiment. Specifically, FIG. 9 is a view illustrating a case where the lid 110 of an optical unit 100B is in the closed state. Furthermore, FIG. 10 is a view illustrating a state in which the lid 110 of the optical unit 100B is removed. Description on the points similar to those of the toilet system 1 according to the first embodiment or the toilet seat apparatus 2A of the second embodiment will be appropriately omitted by adding similar reference numerals.

A toilet system 1B includes a toilet seat apparatus 2B, an optical unit 100B, and an operation device 10 (not illustrated). In the toilet system 1B illustrated in FIGS. 9 and 10, only the configuration necessary for the explanation of the toilet seat apparatus 2B and the optical unit 100B is illustrated, omitting the illustration of other configurations (operation device 10 or the like). The toilet seat apparatus 2B is provided in the toilet room R (refer to FIG. 1) similarly to the toilet seat apparatus 2. As illustrated in FIG. 9, the toilet seat apparatus 2B differs from the toilet seat apparatus 2 in that a main body cover 30B of a main body 3B does not have an opening 31 for the optical unit or that the optical unit 100B is provided separately. In this manner, in the toilet system 1B, the optical unit 100B functions as an excrement detection apparatus separate from the toilet seat apparatus 2B. As illustrated in FIG. 9, the optical unit 100B, which is an excrement detection apparatus, is disposed in a toilet bowl 7 in which a bowl unit 8 that receives excrement is formed.

As illustrated in FIG. 9, in the toilet system 1B, the optical unit 100B is disposed by being hooked between the rim 9 of the toilet seat apparatus 2B and the toilet seat 5. Specifically, the optical unit 100B is provided while being hooked on the rim 9 by a hook unit (hook structure) of a housing 101B that accommodates the optical unit 100B. The optical unit 100B is arranged along the inner peripheral wall of the rim 9 in a direction in which the lid 110, the light emitting unit 120, and the light receiving unit 130 face the inside of the toilet bowl 7. The housing 101B has a configuration in which its main body for accommodating the light emitting unit 120 and the light receiving unit 130 is disposed along the inner peripheral wall of the rim 9, and is hooked on the rim 9 by using its hook unit provided on the opposite side of the end portion on which the main body portion is provided.

The lid 110 is provided on one surface of a housing 101B that accommodates configurations (light emitting unit 120, light receiving unit 130, etc. in FIG. 8) other than the lid 110 of the optical unit 100B. The lid 110 covers an opening surface of the housing 101B corresponding to the front side of the light emitting unit 120 and the light receiving unit 130. In the closed state of the lid 110, the light emitting unit 120, the light receiving unit 130, or the like are hidden behind the lid 110. In the closed state of the lid 110, the lid 110 is located in front of the light emitting unit 120 and the light receiving unit 130. That is, in the closed state of the lid 110, the lid 110 is located in a direction toward the inside of the toilet bowl 7 from the light emitting unit 120 and the light receiving unit 130. With this configuration, in the closed state of the lid 110, the light emitting unit 120 and the light receiving unit 130 are covered by the housing 101B and the lid 110. Although the example of FIG. 7 is a case where the lid 110 is formed of material having no or low transparency similarly to the housing 101B, the lid 110 may be formed of a material different from the housing 101B.

As illustrated in FIG. 10, when the lid 110 is removed, the light emitting unit 120 and the light receiving unit 130 of the optical unit 100B are exposed from the housing 101B. For example, when the lid 110 is in the open state, the lid 110 is not located in front of the light emitting unit 120 and the light receiving unit 130, as illustrated in FIG. 10. With this configuration, the light emitting unit 120 and the light receiving unit 130 are exposed when the lid 110 is in the open state. The opening/closing operation of the lid 110 with respect to the housing 101B is similar to the opening/closing operation of the lid 110 with respect to the main body cover 30, and the description thereof will be omitted. The toilet system 1B illustrated in FIGS. 9 and 10 is completed in installation merely by attaching the optical unit 100B to the existing toilet bowl 7. Therefore, the toilet system 1B can eliminate the necessity to purchase a toilet seat apparatus (for example, toilet seat apparatus 2 of toilet system 1) or a toilet device (for example, a toilet device including the optical unit 100A and the toilet seat 5 of the toilet system 1A), leading to a lower purchase unit price.

<6-2-1. Functional Configuration of Toilet System>

Figure 11:
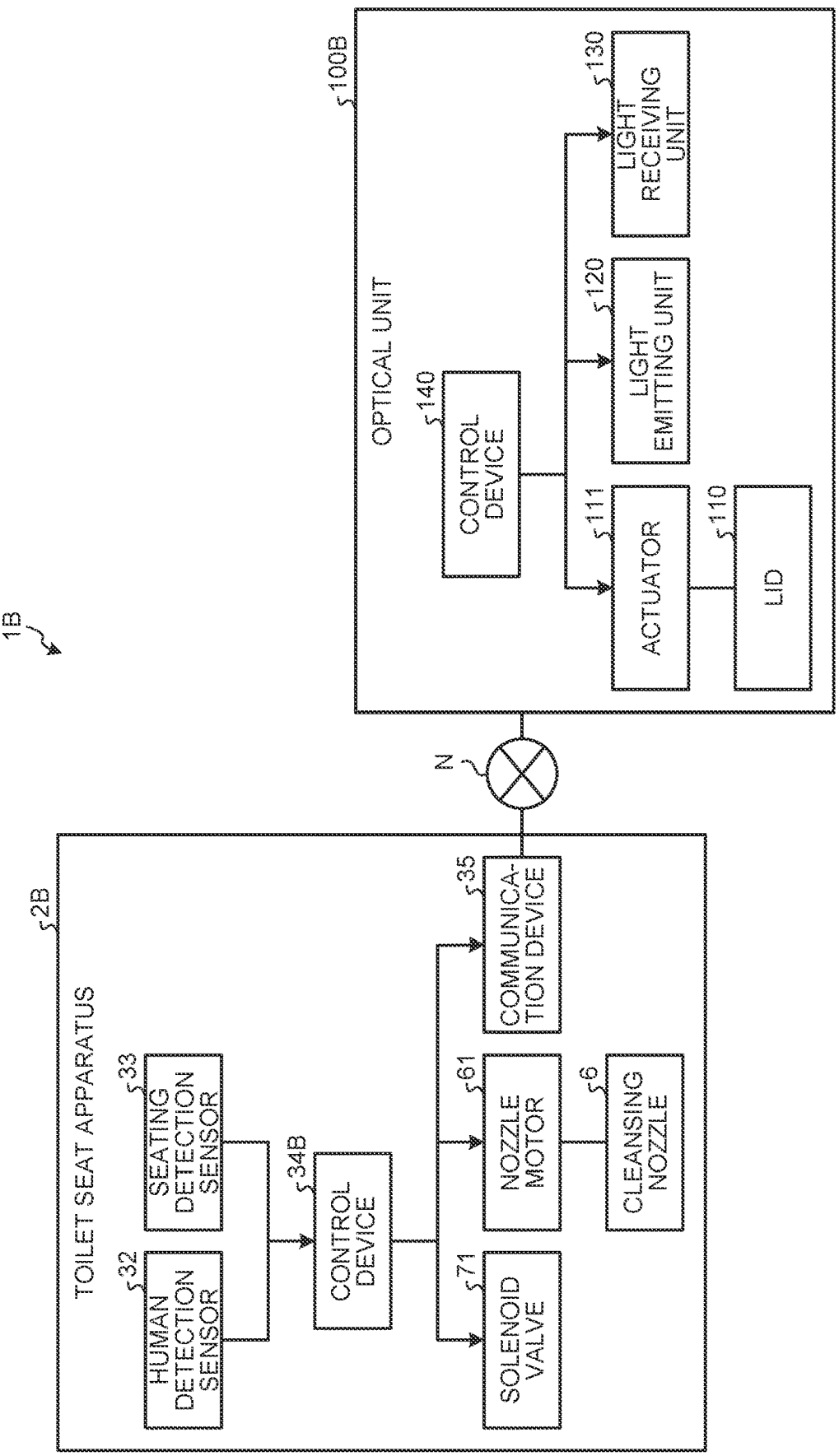
FIG. 11 is a block diagram illustrating an example of a functional configuration of the toilet system according to the third embodiment.

Next, the functional configuration of the toilet system 1B will be described with reference to FIG. 11. FIG. 11 is a block diagram illustrating an example of a functional configuration of the toilet system according to the third embodiment. As illustrated in FIG. 11, the toilet system 1B includes a toilet seat apparatus 2B and an optical unit 100B that communicates with the toilet seat apparatus 2B. While the toilet system 1B includes other devices such as the operation device 10 (not illustrated) as described above, points similar to the toilet systems 1 and 1A will be omitted.

As illustrated in FIG. 11, the toilet seat apparatus 2B includes a human detection sensor 32, a seating detection sensor 33, a control device 34B, a communication device 35, a solenoid valve 71, a nozzle motor 61, a cleansing nozzle 6, and an optical unit 100B. Note that FIG. 11 omits illustrations of a part (main body 3, toilet seat 5, toilet bowl 7, etc.) of the configuration of the toilet seat apparatus 2, similarly to FIG. 4.

The communication device 35 is actualized by a communication circuit or the like and communicates with the optical unit 100B. The communication device 35 is connected to the network N by wired or wireless connection, and transmits/receives information to/from an information processing device such as the optical unit 100B. The communication device 35 communicates with the optical unit 100B under the control of the control device 34B. Furthermore, the communication device 35 may transmit/receive information to/from an information processing device such as the operation device 10 via the network N or another network.

The control device 34B functions as a control unit that controls various configurations and processes. Similarly to the control device 34, the control device 34B controls the nozzle motor 61 and the solenoid valve 71. Furthermore, the control device 34B controls the optical unit 100B via the communication device 35. The control device 34B controls the optical unit 100B via the communication device 35 in order to open and close the lid 110. The control device 34B transmits control information for setting the lid 110 to the open state to the optical unit 100B via the communication device 35. The control device 34B transmits control information for setting the lid 110 to the closed state to the optical unit 100B via the communication device 35. Similarly to the control device 34, the control device 34B may include a processor such as a CPU, MPU, or ASIC, an arithmetic processing device 342 (refer to FIG. 18) actualized by various means such as an integrated circuit such as an FPGA, and various types of storage units, or the like.

The optical unit 100B includes a lid 110, an actuator 111, a light emitting unit 120, a light receiving unit 130, a control device 140, and a communication device (not illustrated). The optical unit 100B functions as an excrement detection apparatus (excrement measurement device) similarly to the optical unit 100.

The communication device of the optical unit 100B is actualized by a communication circuit or the like, and communicates with the toilet seat apparatus 2B. The communication device of the optical unit 100B is connected to the network N by wired or wireless connection, and transmits/receives information to/from an information processing device such as toilet seat apparatus 2B. The communication device of the optical unit 100B communicates with the toilet seat apparatus 2B under the control of the control device 140. Furthermore, the communication device of the optical unit 100B may transmit/receive information to/from an information processing device such as the operation device 10 via the network N or another network.

The control device 140 functions as a control unit that controls various configurations and processes. The control device 140 controls various configurations of the optical unit 100. The control device 140 controls the lid 110, the actuator 111, the light emitting unit 120, and the light receiving unit 130 in cooperation with the control device 34. The control device 140 controls the lid 110, the actuator 111, the light emitting unit 120, and the light receiving unit 130 based on the signal (control information, or the like) received from the control device 34.

The control device 140 controls the opening/closing of the lid 110. By controlling the actuator 111, the control device 140 controls the opening/closing of the lid 110. The control device 140 receives control information for setting the lid 110 to the open state from the control device 34, and causes the actuator 111 to open the lid 110. The control device 140 receives control information for setting the lid 110 to the closed state from the control device 34, and causes the actuator 111 to close the lid 110.

The control device 140 controls turning on/off of the light emitting unit 120. The control device 140 receives control information for controlling the turning on/off of the light emitting unit 120 from the control device 34, and controls the turning on/off of the light emitting unit 120. The control device 140 receives control information for controlling the function of the electronic shutter of the light receiving unit 130 from the control device 34, and controls the function of the electronic shutter of the light receiving unit 130. The control device 140 controls the function of the electronic shutter of the light receiving unit 130.

The control device 140 transmits control information to the lid 110, the actuator 111, the light emitting unit 120, and the light receiving unit 130 by wired communication. The control device 140 may transmit control information to the lid 110, the actuator 111, the light emitting unit 120, and the light receiving unit 130 by wireless communication.

Similarly to the control device 34 and the control device 34B, the control device 140 may include a processor such as a CPU, MPU, or ASIC, an arithmetic processing device actualized by various means such as an integrated circuit such as an FPGA, and various types of storage units, or the like.

<7. Various Configurations and Processes>

From here, various configurations and processes will be described by taking the toilet system 1, the toilet seat apparatus 2, and the optical unit 100 according to the first embodiment as an example. In the following description, various configurations of the toilet system 1 may be read interchangeably as corresponding configurations in the toilet system 1A and the toilet system 1B. For example, the toilet seat apparatus 2 may be read interchangeably as the toilet seat apparatus 2A or the toilet seat apparatus 2B, and the optical unit 100 may be read as the optical unit 100A or the optical unit 100B.

<8. Configuration Example of Light Emitting Unit and Light Receiving Unit>

Figure 12:
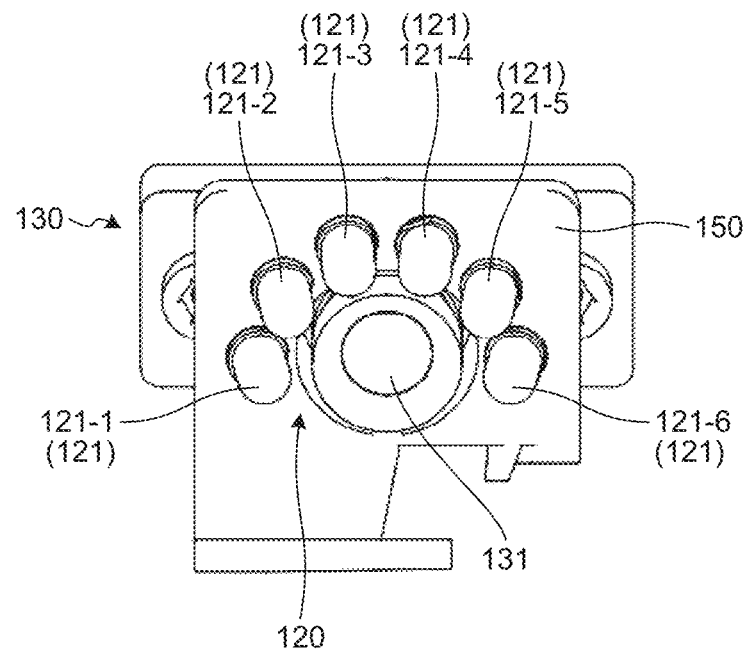
FIG. 12 is a view illustrating an example of a configuration of a light emitting unit and a light receiving unit.
Figure 13:
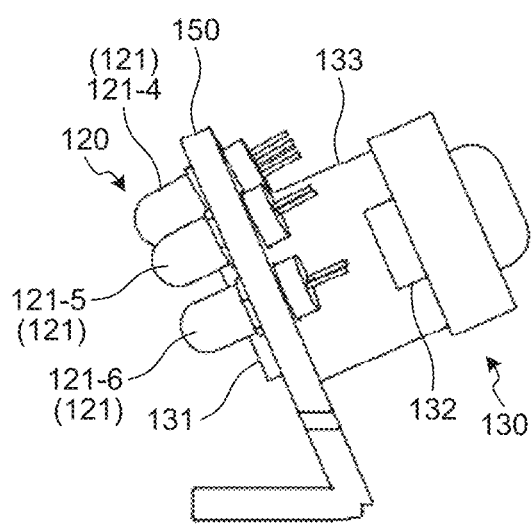
FIG. 13 is a side view illustrating an example of a configuration of a light emitting unit and a light receiving unit.
Figure 14:
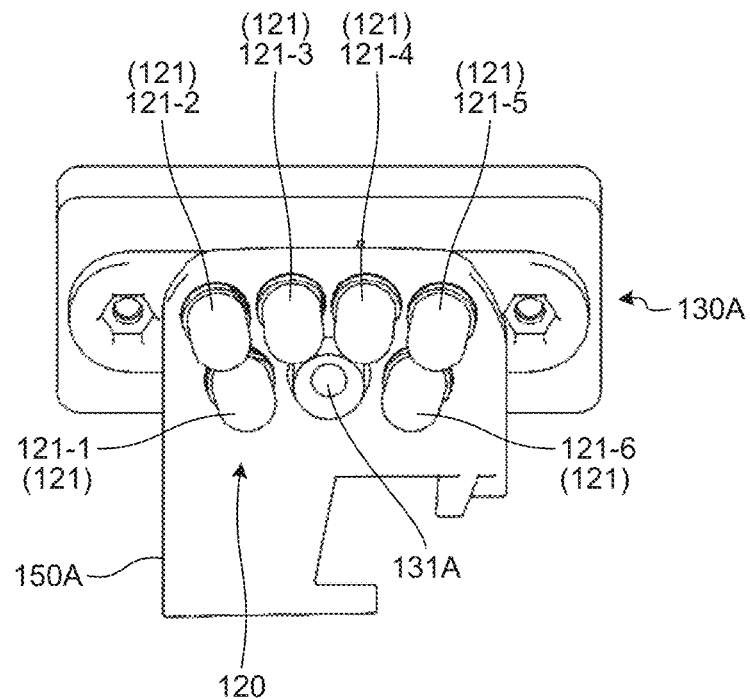
FIG. 14 is a view illustrating another example of a configuration of the light emitting unit and the light receiving unit.
Figure 15:
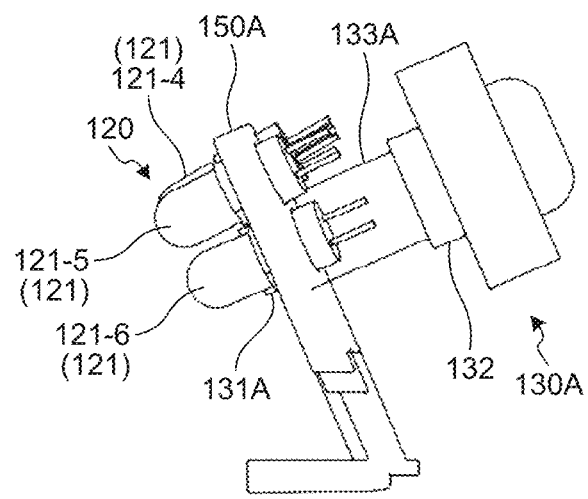
FIG. 15 is a side view illustrating another example of the configuration of the light emitting unit and the light receiving unit.
Figure 16:
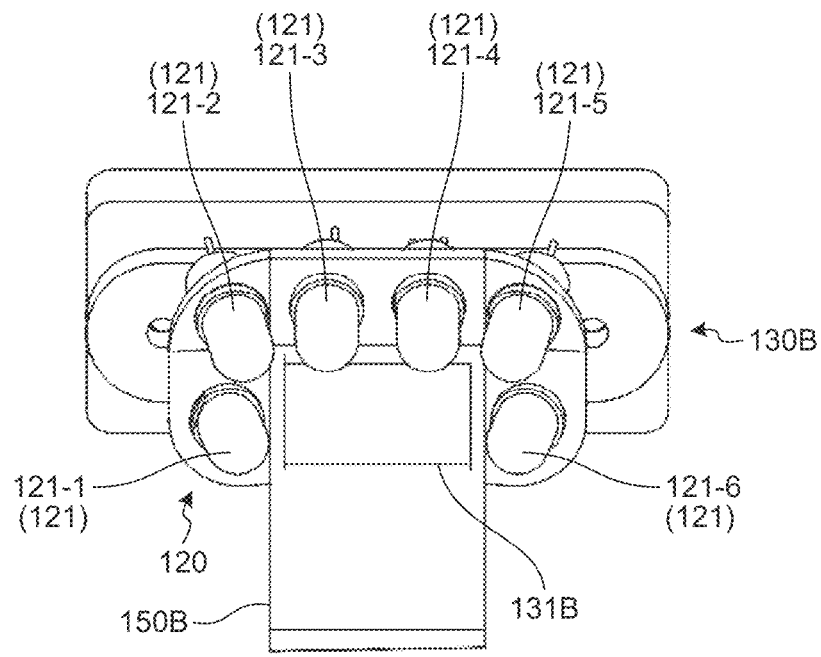
FIG. 16 is a view illustrating an example of a configuration of a light emitting unit, and a light receiving unit using a cylindrical lens.
Figure 17:
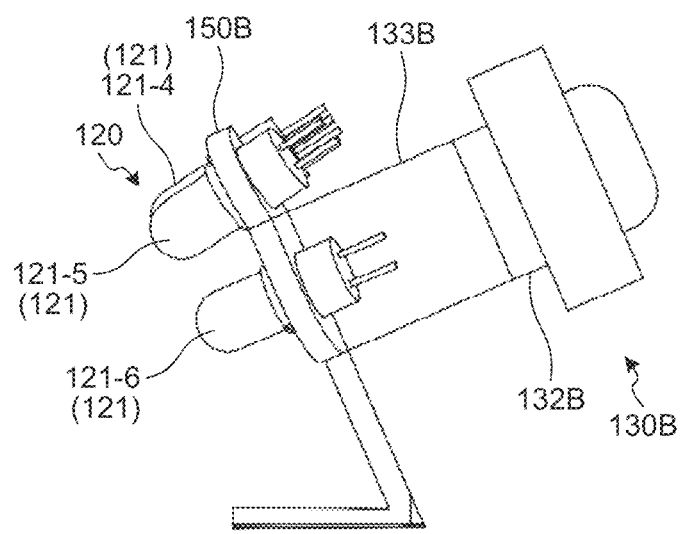
FIG. 17 is a side view illustrating an example of the configuration of a light emitting unit and a light receiving unit using a cylindrical lens.

First, various configurations of the light emitting unit and the light receiving unit will be described with reference to FIGS. 12 to 17. The configurations of the light emitting unit 120 and light receiving units 130, 130A, and 130B illustrated in FIGS. 12 to 17 may be adopted in any of the optical units 100, 100A, and 100B when the configurations are adoptable. In the following, the configurations of the light emitting unit 120 and the light receiving unit 130 illustrated in FIGS. 12 and 13 are described as a "first configuration", the configurations of the light emitting unit 120 and the light receiving unit 130A illustrated in FIGS. 14 and 15 are described as a "second configuration" and the configurations of the light emitting unit 120 and the light receiving unit 130B illustrated in FIGS. 16 and 17 are described as a "third configuration", in some cases. For example, the light emitting unit 120 and the light receiving unit 130 of the optical unit 100 may take any of the first to third configurations described below.

<8-1. First Configuration of Light Emitting Unit and Light Receiving Unit>

First, the first configuration illustrated in FIGS. 12 and 13 will be described. FIG. 12 is a view illustrating an example of a configuration of a light emitting unit and a light receiving unit. FIG. 13 is a side view illustrating an example of a configuration of a light emitting unit and a light receiving unit.

As illustrated in FIGS. 12 and 13, the light emitting unit 120 of the first configuration has six light emitting elements 121-1, 121-2, 121-3, 121-4, 121-5, and 121-6. In the following, the light emitting elements 121-1, 121-2, 121-3, 121-4, 121-5, and 121-6, etc. will be described as a "light emitting element 121" other than a case where distinction is needed in description. For example, the light emitting element 121 is a Light Emitting Diode (LED). For the light emitting element 121, various elements may be used, not limited to the LED.

In the following, the light emitting element 121 that emits light having a wavelength in the invisible light region or a wavelength close to the invisible light region will be described as a "first light emitting element", and the light emitting element 121 that emits light having a wavelength in the visible light region will be described as "second light emitting element", "third light emitting element", "fourth light emitting element", or the like, in some cases. For example, the first light emitting element may be used in both the standby mode and the measurement mode described below, and the second light emitting element may be used only in the measurement mode, the details of which will be described below.

As illustrated in FIGS. 12 and 13, the light receiving unit 130 of the first configuration includes a lens 131, a light receiving element 132, and a case 133 for supporting the lens 131. For example, the light receiving element 132 is a line sensor. For example, the light receiving element 132 is a line sensor in which Charge Coupled Device (CCD) sensors or Complementary Metal Oxide Semiconductor (CMOS) sensors are arranged in a row. For the light receiving element 132, various sensors such as an area sensor (two-dimensional image sensor) may be used, not limited to a line sensor (one-dimensional image sensor). In a case where the optical unit 100 is an excrement detection apparatus, the control device 140 may be provided in a rectangular member located on the back surface side of the light receiving element 132.

A support unit 150 supports the light emitting unit 120 and the light receiving unit 130. The support unit 150 may be formed of various materials that can support the light emitting unit 120 and the light receiving unit 130. The support unit 150 supports the light emitting unit 120 and the light receiving unit 130 so that the light emitting unit 120 and the light receiving unit 130 are exposed on one surface (hereinafter, also referred to as "front surface") side of the support unit 150. For example, the support unit 150 supports the light emitting unit 120 and the light receiving unit 130 so that the lenses 131 of each of the light emitting elements 121 and the light receiving unit 130 are exposed. Each of the light emitting elements 121 emits light in a direction in which the front surface of the support unit 150 faces, and the light receiving unit 130 receives light in a direction in which the front surface of the support unit 150 faces. For example, each of the light emitting elements 121 and the light receiving unit 130 are connected to a power supply device (not illustrated) on an opposite surface (rear surface) of the front surface of the support unit 150, from which electric power is supplied to the units.

As illustrated in FIG. 12, each of the light emitting elements 121 of the light emitting unit 120 is arranged around the light receiving unit 130. Furthermore, in the first configuration, the lens 131 of the light receiving unit 130 is larger in size than the light emitting element 121 of the light emitting unit 120.

<8-1-1. Emission Wavelength and Arrangement Example of Light Emitting Elements>

Here, an example of the wavelength of light (emission wavelength) emitted by each light emitting element is illustrated. In the example of FIG. 12, two light emitting elements 121, namely, the light emitting elements 121-3 and 121-4, are the first light emitting elements 121 that emit light having a wavelength in the invisible light region or a wavelength close to the invisible light region; four light emitting elements 121, namely, the elements 121-1, 121-2, 121-5, and 121-6, are the second light emitting elements 121 that emit visible light. Each of the first light emitting elements 121 may emit light of the same wavelength, or may emit light of a mutually different wavelength. Each of the second light emitting elements 121 may emit light of the same wavelength, or may emit light of a mutually different wavelength. For example, the second light emitting elements 121-1 and 121-2 may emit light having the same wavelength. Furthermore, the light emitting elements 121-5 and 121-6 may be the third light emitting elements 121-5 and 121-6 that emit light having the same wavelength being the light having a wavelength different from the wavelength of the light emitted by the second light emitting elements 121-1 and 121-2. For example, in order to distinguish the color of excrement, it is desirable that the light emitting unit 120 can emit light in three or more wavelength regions.

For example, the wavelength region of light emitted by the first light emitting element 121 (also referred to as "first wavelength region") is a wavelength region of 700 nm or more. In this manner, the first wavelength region is a wavelength region in the invisible light region or a wavelength region close to the invisible light region. For example, the first wavelength region is a wavelength region corresponding to infrared rays, red light, or the like. Furthermore, for example, the wavelength region of the light emitted by the second light emitting element 121 (also referred to as "second wavelength region") is a wavelength region of 600 nm or more and less than 700 nm. In this manner, the second wavelength region is a wavelength region of the visible light region. For example, the second wavelength region is a wavelength region corresponding to orange to red or the like. Furthermore, for example, the wavelength region of the light emitted by the third light emitting element 121 (also referred to as "third wavelength region") is a wavelength region of 450 nm or more and less than 600 nm. In this manner, the third wavelength region is a shorter wavelength region compared to the second wavelength region, and is a wavelength region of the visible light region. For example, the third wavelength region is a wavelength region corresponding to blue to yellow or the like. The specific numerical values of the first wavelength region, the second wavelength region, and the third wavelength region described above are examples, and the wavelength regions are not limited thereto. The first wavelength region may be a wavelength region corresponding to infrared (red), the second wavelength region may be a wavelength region corresponding to green, and the third wavelength region may be a wavelength region corresponding to blue close to green.

Further, it is preferable that the light emitting elements 121 that emit the same wavelength are arranged so as to be adjacent to each other. As described above, two adjacent light emitting elements 121-3 and 121-4 are defined as the first light emitting elements 121, two adjacent light emitting elements 121-1 and 121-2 are defined as the second light emitting elements 121, and two adjacent light emitting elements 121-5 and 121-6 are defined as the third light emitting elements 121. Furthermore, it is desirable that the first light emitting elements 121-3 and 121-4 are arranged at upper positions compared to the other light emitting elements 121-1, 121-2, 121-5, and 121-6. The above-described arrangement of the first light emitting element 121 to the third light emitting element 121 is an example, and is not limited to this.

In this manner, the toilet system 1 performs detection related to the user's excrement by the light emitting unit 120 having the light emitting elements 121 (LEDs) individually corresponding to three wavelength regions, and by the light receiving unit 130 having one line sensor or the like. Not limited to the three wavelength regions, the toilet system 1 may perform detection related to the user's excrement by using, for example, the light emitting unit 120 having the light emitting elements 121 (LEDs) individually corresponding to five wavelength regions. For example, it is allowable, in FIGS. 12 and 13, to have a configuration in which two light emitting elements 121, namely, the first light emitting elements 121-3 and 121-4, emit light in the first wavelength region while the remaining four light emitting elements 121-1 and 121-2, 121-5, and 121-6 emit light in mutually different wavelength regions (second wavelength region to fifth wavelength region). In this case, the first wavelength region may be the longest wavelength region, and wave length regions may be shorter in the order of the second wavelength region, the third wavelength region, the fourth wavelength region, and the fifth wavelength region. The configuration for the detection related to the user's excrement is not limited to the above. For example, the detection may be performed by using a configuration including: a light emitting unit having a light emitting element (LED) that emits white light and; a light receiving unit having a spectral function such as a spectral filter.

<8-2. Second Configuration of Light Emitting Unit and Light Receiving Unit>

Next, the second configuration illustrated in FIGS. 14 and 15 will be described. FIG. 14 is a view illustrating another example of a configuration of the light emitting unit and the light receiving unit. FIG. 15 is a side view illustrating another example of the configuration of the light emitting unit and the light receiving unit. The description of the points similar to the first configuration will be omitted as appropriate.

As illustrated in FIGS. 14 and 15, the light emitting unit 120 having the second configuration includes six light emitting elements 121. The light receiving unit 130A of the second configuration includes a lens 131A, a light receiving element 132, and a case 133A for supporting the lens 131A. A support unit 150A supports the light emitting unit 120 and the light receiving unit 130A similarly to the support unit 150.

As illustrated in FIG. 14, each of the light emitting elements 121 of the light emitting unit 120 is arranged around the light receiving unit 130A. Furthermore, in the second configuration, the lens 131A of the light receiving unit 130A is about the same size as the light emitting element 121 of the light emitting unit 120. Therefore, by taking an appropriate arrangement of the light emitting unit 120 (each of the light emitting elements 121), the overall size can be reduced as compared with the first configuration.

<8-3. Third Configuration of Light Emitting Unit and Light Receiving Unit>

Next, the third configuration illustrated in FIGS. 16 and 17 will be described. FIG. 16 is a view illustrating an example of a configuration of a light emitting unit, and a light receiving unit using a cylindrical lens. FIG. 17 is a side view illustrating an example of the configuration of a light emitting unit and a light receiving unit using a cylindrical lens. The description of the points similar to the first configuration and the second configuration will be omitted as appropriate.

As illustrated in FIGS. 16 and 17, the light emitting unit 120 having the third configuration includes six light emitting elements 121. The light receiving unit 130B of the third configuration includes a lens 131B which is a cylindrical lens, a light receiving element 132B, and a case 133B for supporting the lens 131B. The light receiving element 132B is a line sensor. In this manner, the light receiving unit 130B of the third configuration is formed with the lens 131B which is a cylindrical lens and the light receiving element 132B which is a line sensor. A support unit 150B supports the light emitting unit 120 and the light receiving unit 130B similarly to the support unit 150.

As illustrated in FIG. 16, each of the light emitting elements 121 of the light emitting unit 120 is arranged around the light receiving unit 130B. Furthermore, in the third configuration, the light receiving element 132B is a line sensor and the lens 131B is a cylindrical lens. The light receiving element 132B, which is a line sensor, is a sensor that is long in one direction (laterally long). Therefore, using a circular lens would provide the lens also in the region where there is no line sensor (light receiving element 132B). In contrast, as illustrated in the third configuration, by adopting a columnar lens (cylindrical lens) that is long in one direction (laterally long), the lens can be provided only in a region where the sensor is present, making it possible to downsize the entire configuration (in height direction in particular) as compared to the first configuration and the second configuration.

Incidentally, in any of the first to third configurations described above, the optical axis (central axis) of the light emitting element 121 is inclined with respect to the central axis of the light receiving unit 130 (lens 131). Details of this point will be described below. Note that the optical axis of the light emitting element 121 is an axis that passes through a point having the highest illuminance at a position equidistant from the light emitting element 121. In addition, the position of half the illuminance of the optical axis of the light emitting element 121 is defined as the half-power angle.

<9. Process of Collecting Excretion Information>

Next, a process of collecting excretion information in the toilet system 1 will be described.

<9-1. Configuration of Excretion Information Collection>

Figure 18:
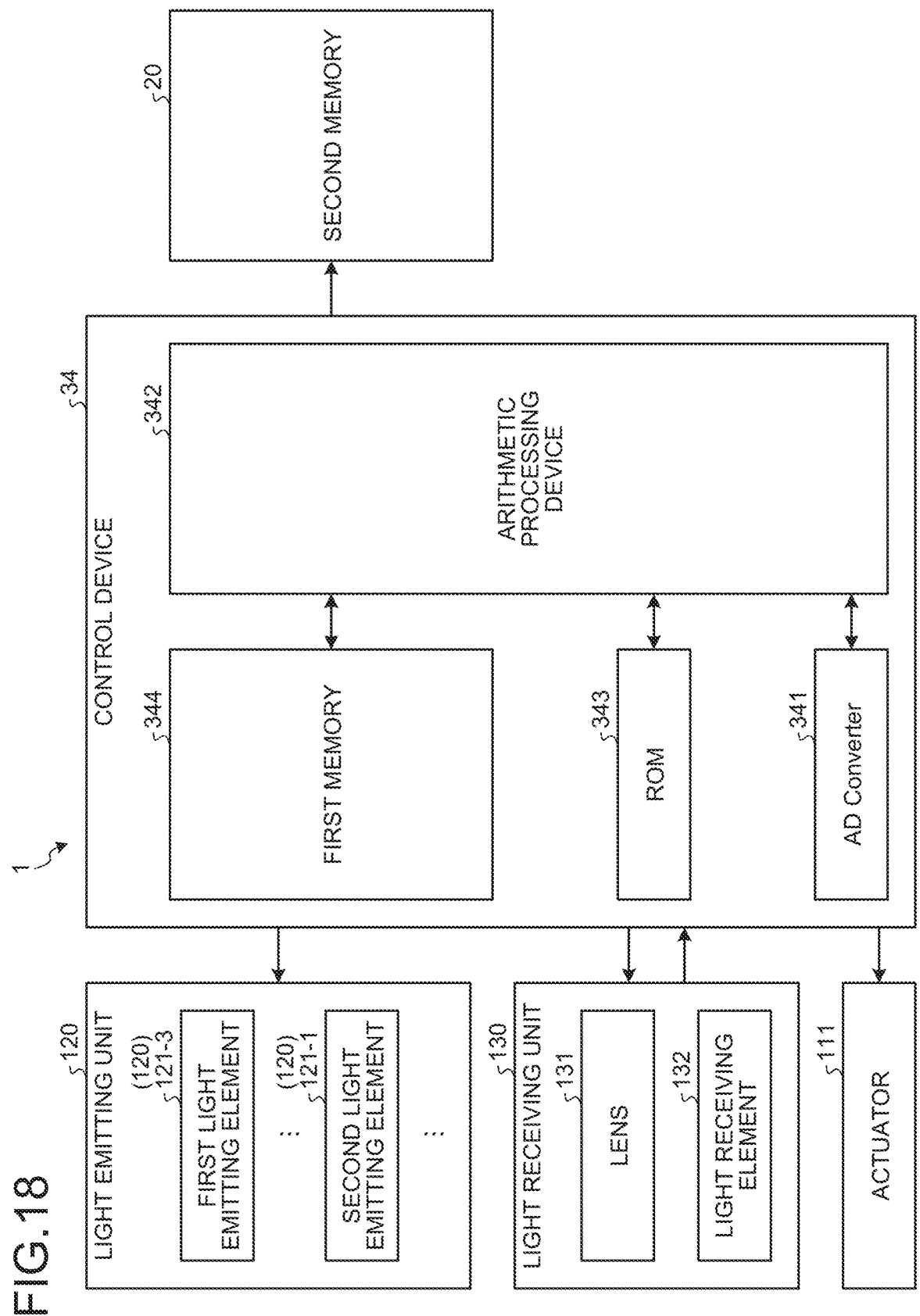
FIG. 18 is a block diagram illustrating an example of a functional configuration of a toilet system related to a process of excretion information collection.

First, a specific configuration for collecting excretion information in the toilet system 1 will be described with reference to FIG. 18. FIG. 18 is a block diagram illustrating an example of a functional configuration of a toilet system related to a process of excretion information collection. The description of points similar to those of the toilet systems 1, 1A, and 1B described above will be appropriately omitted by adding the similar reference numerals.

As illustrated in FIG. 18, the toilet system 1 includes a configuration such as an actuator 111, a light emitting unit 120, a light receiving unit 130, a control device 34, and second memory 20. For the toilet system 1 in FIG. 18, the configuration needed for explaining the collection of excretion information is selectively illustrated, while omitting the illustration of other configurations (operation device 10 or the like). Furthermore, when the system functions as an excrement detection apparatus in which the optical unit 100B is separated from the toilet seat apparatus 2B as in the toilet system 1B, the following configuration and processes of the control device 34 may be read interchangeably as the configuration and processes of the control device 140.

The actuator 111 is a drive source that sets the lid 110 to the open state or the closed state. The light emitting unit 120 has a plurality of light emitting elements 121 such as the first light emitting element 121-3 and the second light emitting element 121-1. Alternatively, the light emitting unit 120 may have only one light emitting element, and the light emitting element may emit beams of light having a plurality of wavelengths. That is, the light emitting unit 120 may have only one light emitting element that emit invisible light and visible light. In this manner, the light emitting unit 120 may have only one light emitting element having the functions of both the first light emitting element and the second light emitting element. The light receiving unit 130 includes a lens 131 and a light receiving element 132.

The control device 34 of the toilet seat apparatus 2 has an AD Converter 341, an arithmetic processing device 342, ROM 343, and first memory 344.

The AD Converter 341 is an A/D converter, having a function of converting an analog signal into a digital signal. The AD Converter 341 may be an analog-to-digital conversion circuit. For example, the AD Converter 341 converts analog data received (detected) by the light receiving unit 130 into digital data. The AD Converter 341 converts analog data obtained by deleting a predetermined range of data from analog data, into digital data. For example, the AD Converter 341 keeps only the data corresponding to the pixels in the preset range (for example, a predetermined range in the center), and deletes the data corresponding to the pixels in the remaining range. When a dedicated sensor such as a line sensor in which the number of pixels is set for excrement detection is used as the light receiving element 132, the AD Converter 341 converts the entire analog data into digital data without deleting the data in a predetermined range.

The arithmetic processing device 342 is realized by various means such as a CPU and a microcomputer, and executes various processes. For example, the arithmetic processing device 342 executes various processes using the digital data converted by the AD Converter 341. The arithmetic processing device 342 executes various processes by a program (for example, an excretion determination program) stored in the ROM 343. For example, the arithmetic processing device 342 is actualized by executing a program stored in the ROM 343 using a temporarily used storage region or the like in the arithmetic processing device 342 as a work region.

The arithmetic processing device 342 analyzes the data. The arithmetic processing device 342 analyzes the data temporarily stored in the first memory 344. The arithmetic processing device 342 transfers the data received by the light receiving unit 130 to the first memory 344, and analyzes and deletes the data stored in the first memory 344. The arithmetic processing device 342 transfers the data received by the light receiving unit 130 to the first memory 344. At the same time, when it is analyzed that the data temporarily stored in the first memory 344 is not data based on the reflected light from the falling feces, the arithmetic processing device 342 sets the data ready for deletion.

Before transferring the data received by the light receiving unit 130 to the first memory 344, the arithmetic processing device 342 deletes a part of the data received by the light receiving unit 130. When having analyzed that the data temporarily stored in the first memory 344 is the data based on the reflected light from the falling feces, the arithmetic processing device 342 keeps storing the data in the first memory 344. In addition, when the period of analysis that the data temporarily stored in the first memory 344 in succession is not data based on the reflected light from the falling feces has passed, at a later time, for a predetermined period or more, the arithmetic processing device 342 transfers the data based on the reflected light from the falling feces stored in the first memory 344 to the second memory 20. When the amount of data based on the reflected light from the falling feces temporarily stored in the first memory 344 exceeds a predetermined threshold, the arithmetic processing device 342 transfers the data based on the reflected light from the falling feces stored in the first memory 344, to the second memory 20.

The ROM 343 is Read Only Memory (ROM), and stores various programs such as an excretion determination program.

The first memory 344 is a storage device (memory) that temporarily stores various data. The first memory 344 stores the data received by the light receiving unit 130. The first memory 344 stores the digital data converted by the AD Converter 341. For example, the first memory 344 is Static Random Access Memory (SRAM). The memory used as the first memory 344 is not limited to SRAM, but may be other memory such as Random Access Memory (RAM) including Dynamic Random Access Memory (DRAM) or ROM capable of high-speed processing such as Programmable Read Only Memory (PROM).

The first memory 344 stores data under the control by the arithmetic processing device 342. For example, the first memory 344 can use a storage device having a storage capacity of 96 kilobytes, 512 kilobytes, or the like. The data received by the light receiving unit 130 temporarily stored in the first memory 344 includes raw data (analog data) detected by the light receiving unit 130 and data (digital data) processed by A/D conversion.

The second memory 20 is a storage device (memory) that stores various data. The second memory 20 stores digital data acquired from the control device 34. For example, Electrically Erasable Programmable Read-Only Memory (EEPROM) or the like is used as the second memory 20. The second memory 20 may be various storage devices (memory) such as Secure Digital (SD) card memory and Universal Serial Bus (USB) flash drive memory.

The second memory 20 can transfer the data stored in the first memory 344. The second memory 20 has a larger storage region compared to the first memory 344. For example, the second memory 20 uses a storage device having a larger storage capacity, for example, 4 gigabytes, than that of the first memory 344. The data stored in the second memory 20 may be transmitted to an external device. The toilet system 1 may transmit the data stored in the second memory 20 to an external device such as a terminal device used by the user by wireless communication using the communication device or the like of the toilet seat apparatus 2.

The second memory 20 may be provided at any position, that is, inside the toilet seat apparatus 2, outside the toilet seat apparatus 2, or the like. For example, the second memory 20 may be a Micro SD inside the toilet seat apparatus 2, or may be external memory provided outside the toilet seat apparatus 2 to communicate with the toilet seat apparatus 2 via Wireless Fidelity (Wi-Fi: registered trademark) or the like. In this case, the arithmetic processing device 342 transfers the data temporarily stored in first memory 344 to the second memory, which is external memory having a storage region larger than that of the first memory 344, via communication with the second memory. The communication between the second memory 20 and the toilet seat apparatus 2 is not limited to Wi-Fi (registered trademark), but may be communication using various communication standards such as ZigBee (registered trademark) and Bluetooth (registered trademark).

<9-2. Control Flow of Excretion Information Collection Process>

Figure 19:
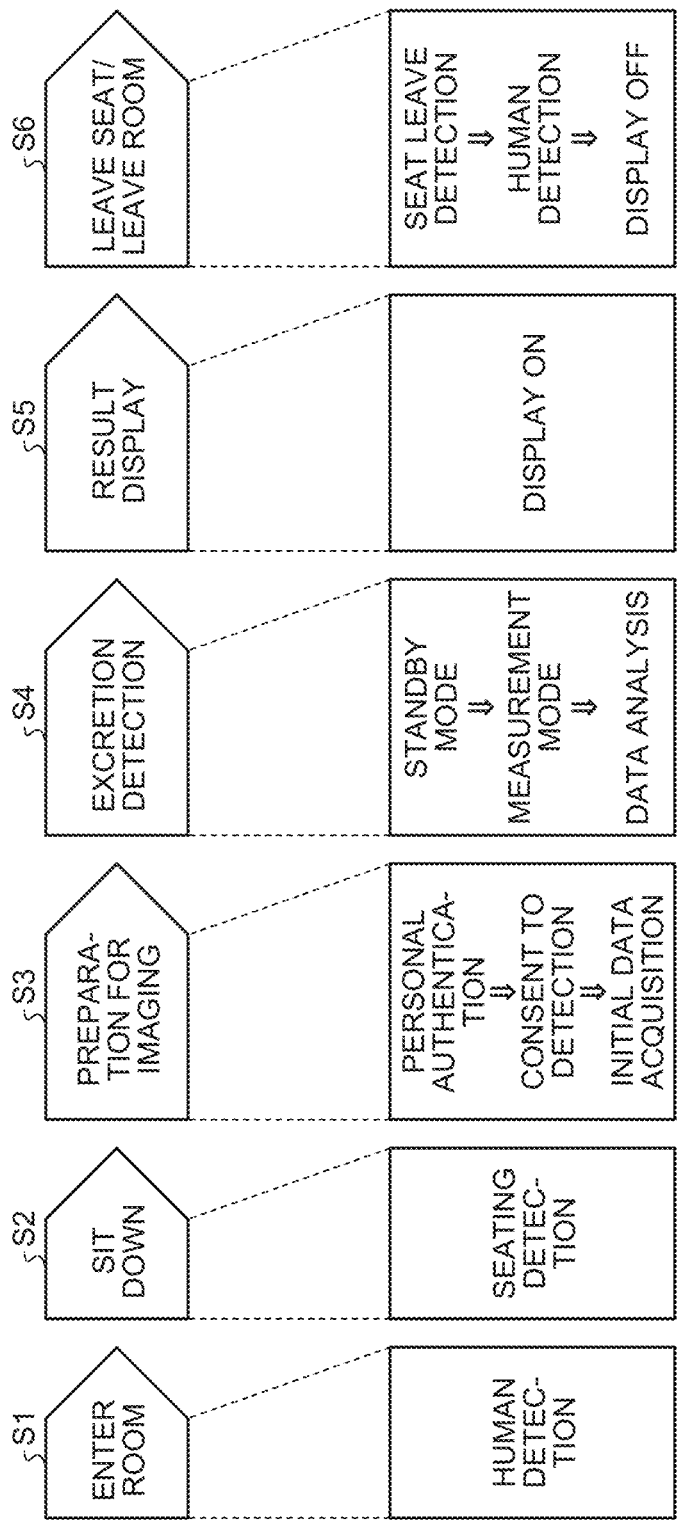
FIG. 19 is a conceptual diagram illustrating a control flow of the process of excretion information collection.

Next, a control flow of excretion information collection process performed by the toilet system 1 will be described with reference to FIG. 19. FIG. 19 is a conceptual diagram illustrating a control flow of the process of excretion information collection.

First, the toilet system 1 detects the user's entry into the toilet room R (Step S1). The toilet system 1 detects the user's entry into the toilet room R based on the human detection performed by the human detection sensor 32.

Then, the toilet system 1 detects the user's seating on the toilet seat 5 in the toilet room R (Step S2). The toilet system 1 detects the user's seating on the toilet seat 5 in the toilet room R based on the seating detection by the seating detection sensor 33.

Subsequently, the toilet system 1 prepares for imaging (Step S3). Toilet system 1 performs personal authentication on the user who entered the toilet room R. For example, the toilet system 1 performs personal authentication on the user based on user's operation on the operation device 10 or communication with a mobile terminal owned by the user. The toilet system 1 may perform personal authentication of the user by any method as long as the method enables the personal authentication of the user who has entered the toilet room R. Toilet system 1 obtains the user's consent to detection related to defecation. For example, the toilet system 1 acquires user's consent on the detection based on user's operation on the operation device 10 or communication with a mobile terminal owned by the user. The toilet system 1 may acquires user's consent on detection by any method as long as the method enables the personal authentication of the user who has entered the toilet room R. For example, when the consent of the user has been acquired, the toilet system 1 sets the lid 110 of the optical unit 100 in the open state and transitions to a state in which defecation by the user is detectable. Subsequently, the toilet system 1 acquires initial data. As initial data, the toilet system 1 acquires data imaged in a state without user's defecation after the user sits on the toilet seat 5. The toilet system 1 uses the initial data not including the reflected light from the excrement first stored in the first memory 344 after sitting, for the subsequent excretion determination. The number of pieces of stored initial data varies depending on the number of wavelengths of the light emitting element 121.

Subsequently, the toilet system 1 detects excretion (Step S4). The toilet system 1 detects excretion in a mode of waiting for user's excretion (also referred to as "standby mode") and a mode of measuring user's excretion (also referred to as "measurement mode"). For example, in the standby mode, the toilet system 1 emits light only to a part of the light emitting elements 121 (that is, the first light emitting element 121) and detects the fall of excrement from the user. In this manner, in the standby mode, for example, among the light emitting elements 121 of individual wavelengths, only the first light emitting element 121 that emits light in the wavelength of the invisible light region or the wavelength region or close to the invisible light region (first wavelength region) turns on. For example, in the standby mode, for example, among the light emitting elements 121 of individual wavelengths, only the first light emitting element 121 that emits light in the wavelength region of 700 nm or more (first wavelength region) turns on. That is, in the standby mode, of the above-described first wavelength region, second wavelength region, and third wavelength region, only the light emitting element 121 that emits the light in the first wavelength region turns on. When the fall of excrement has been detected in the standby mode, the toilet system 1 switches the mode to the measurement mode. For example, in the measurement mode, the toilet system 1 sequentially turns on the individual light emitting elements 121 of individual wavelengths and measures (detects) the falling excrement. In this manner, in the measurement mode, for example, the light emitting elements 121 of individual wavelengths including the first light emitting element 121 that emits light in the wavelength of the invisible light region or the wavelength region or close to the invisible light region (first wavelength region) sequentially turn on. For example, in the measurement mode, the light emitting elements 121 of individual wavelengths including the first light emitting element 121 that emits light in the wavelength region 700 nm or more (first wavelength region) sequentially turn on. That is, in the measurement mode, the light emitting elements 121 that emit light having different wavelengths, such as the above-described first wavelength region, second wavelength region, and third wavelength region, sequentially turn on. Subsequently, the toilet system 1 performs data analysis. For example, the toilet system 1 analyzes the properties of excrement, such as the color and shape of the user's excrement, using the data measured in the measurement mode.

The toilet system 1 then displays a result (Step S5). The toilet system 1 turns on the display when the data analysis is completed. For example, the toilet system 1 displays the analysis result regarding excrement, such as the properties of excrement of the user, on a display device (for example, the display screen 11 of the operation device 10). With this configuration, the user can confirm the properties of his/her excrement. The personal authentication described above may be performed after the result is displayed in Step S5. In a case where there is no authentication, the data will be deleted without being stored in the second memory 20. In a case where the personal authentication from the user of the toilet room R has not been obtained, for example, the control device 34 deletes the data without transferring (transmitting) the data collected during the use of the user to the second memory 20.

The toilet system 1 detects the user's leave from the toilet seat 5 or leave from the toilet room R (Step S6). The toilet system 1 detects the user's leave from the toilet seat 5 of the toilet room R based on the seat leave detection by the seating detection sensor 33. The toilet system 1 detects the user's leave from the toilet room R based on the human detection performed by the human detection sensor 32. The toilet system 1 turns off the display after detecting the user's leave from the toilet room R. For example, the toilet system 1 turns off the result displayed on the display device (for example, the display screen 11 of the operation device 10) after the user leaves the toilet room R. With this configuration, the toilet system 1 can appropriately protect the user's privacy.

<9-3. Standby Mode>

Figure 20:
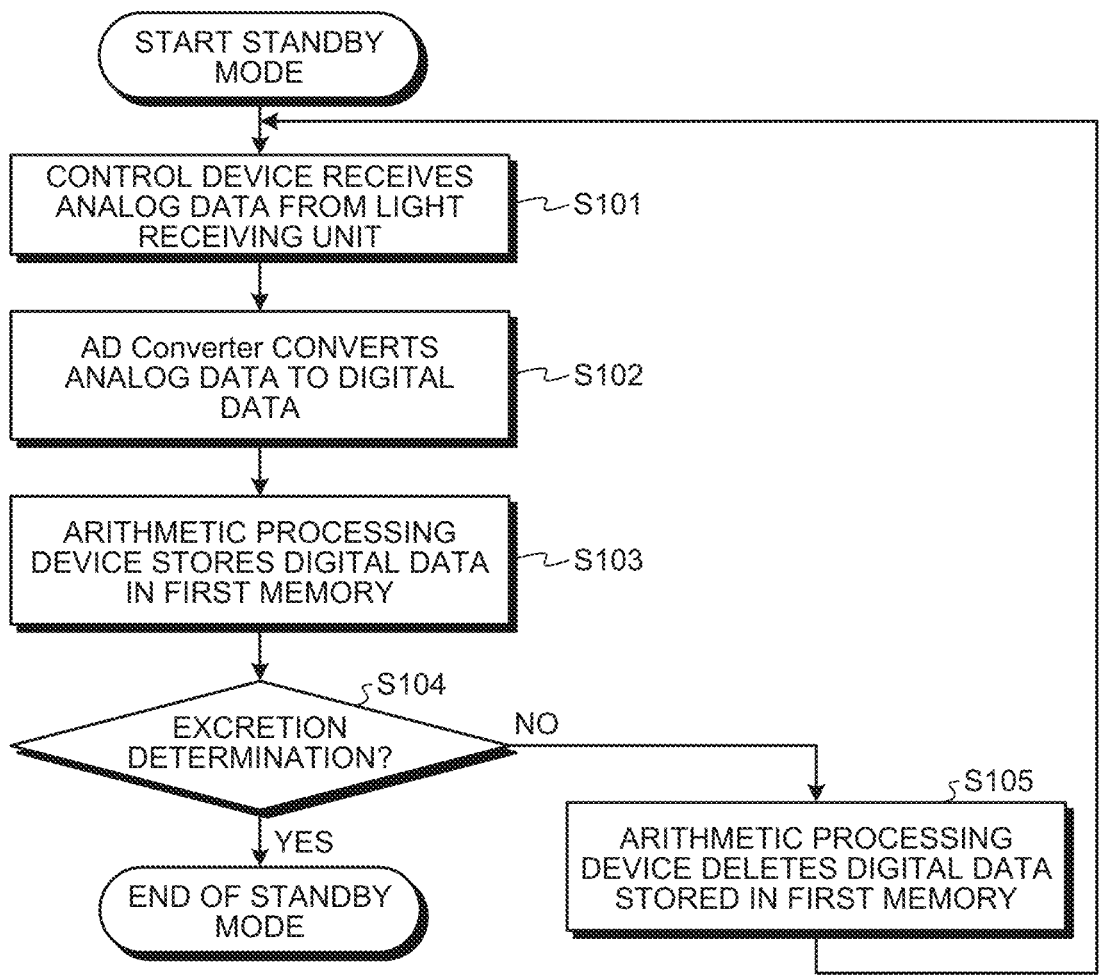
FIG. 20 is a flowchart illustrating an example of a processing procedure in the standby mode.
Figure 21:
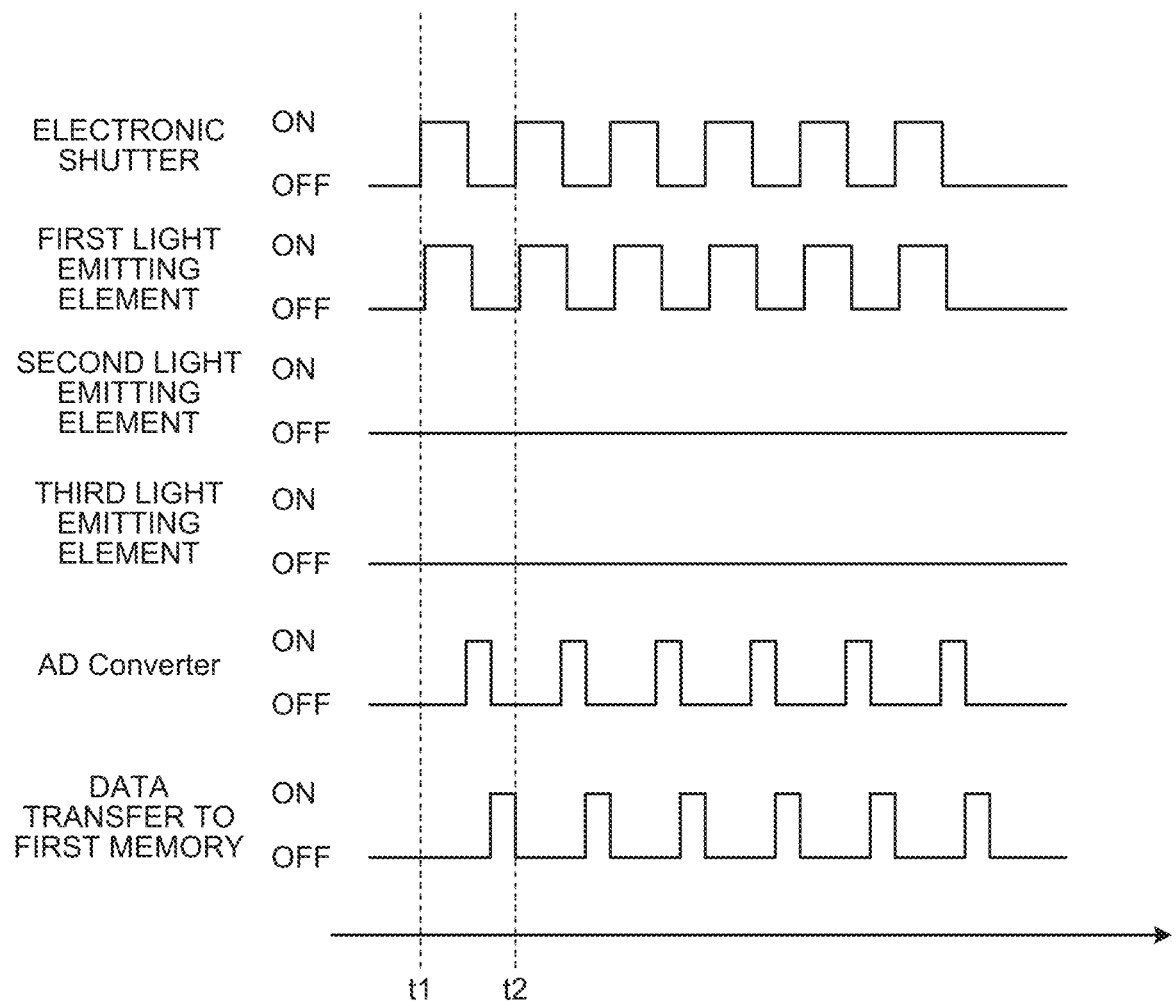
FIG. 21 is a diagram illustrating an example of a time chart in a standby mode.

Next, the specific operation of the standby mode will be described with reference to FIGS. 20 and 21. FIG. 20 is a flowchart illustrating an example of a processing procedure in the standby mode. FIG. 21 is a diagram illustrating an example of a time chart in a standby mode.

First, a flow of processes in the standby mode will be described with reference to FIG. 20. As illustrated in FIG. 20, in the toilet system 1, the control device 34 receives analog data from the light receiving unit 130 (Step S101).

Next, in the toilet system 1, the AD Converter 341 converts analog data into digital data (Step S102). For example, the AD Converter 341 converts analog data obtained by deleting data in a predetermined range from analog data into digital data. For example, the AD Converter 341 converts analog data obtained by deleting data in a predetermined range at both ends from analog data into digital data. Subsequently, in the toilet system 1, the arithmetic processing device 342 stores the digital data in the first memory 344 (Step S103). The arithmetic processing device 342 stores the digital data converted by the AD Converter 341 in the first memory 344. The arithmetic processing device 342 may delete a part of the converted digital data and store the remaining digital data in the first memory 344.

Subsequently, the toilet system 1 makes an excretion determination (Step S104). For example, in the toilet system 1, the control device 34 makes an excretion determination. For example, the control device 34 makes the excretion determination using an excretion determination program stored in the ROM 343 and digital data stored in the first memory 344. For example, the control device 34 makes the excretion determination by determining whether the output value of the light receiving element 132 has varied by a predetermined value or more with respect to the initial data acquired after the user is seated. For example, the control device 34 determines that excretion has occurred when the output value of the light receiving element 132 has varied by a predetermined value or more with respect to the initial data acquired after the user is seated. Furthermore, for example, the control device 34 determines that excretion has not occurred when the output value of the light receiving element 132 has varied less than a predetermined value with respect to the initial data acquired after the user is seated.

When determined that excretion has occurred (Step S104: Yes), the toilet system 1 ends the standby mode and shifts to the measurement mode. That is, when it is determined that the light received by the light receiving element 132 in the toilet system 1 is the light reflected from the excrement, the toilet system 1 ends the standby mode and shifts to the measurement mode.

In contrast, when the toilet system 1 has determined that excretion has not occurred (Step S104: No), the arithmetic processing device 342 deletes the digital data stored in the first memory 344 (Step S105). That is, when it is determined in the toilet system 1 that the light received by the light receiving element 132 is not the light reflected from the excrement, the digital data stored in the first memory 344 in Step S103 will be deleted. The arithmetic processing device 342 may set the digital data stored in the first memory 344 in Step S103 to a state ready for deletion, such as a state ready for being overwritten. The toilet system 1 returns to Step S101 and repeats the process.

Next, a time chart of the standby mode will be described with reference to FIG. 21. As illustrated in FIG. 21, in the standby mode, the processes of various configurations of the toilet system 1 is controlled. For example, processes of the configuration of the electronic shutter of the light receiving unit 130, the first light emitting element 121, the second light emitting element 121, the third light emitting element 121, the AD Converter 341, or the like, and the data transfer to the first memory 344, are controlled.

The first light emitting element 121 emits light having a wavelength in the invisible light region or a wavelength close to the invisible light region. Furthermore, the second light emitting element 121 and the third light emitting element 121 emit light having a wavelength in the visible light region. The second light emitting element 121 and the third light emitting element 121 emit light having different wavelengths. The control illustrated in the time chart of FIG. 21 may be performed by the control device 34.

The electronic shutter is switched between ON and OFF at predetermined intervals. In the example of FIG. 21, the interval from ON to the next ON of the electronic shutter is controlled to a period (first period) between time t1 and time t2. For example, in a state where the electronic shutter is ON (open state), detection (imaging) is performed by the light receiving element 132 of the light receiving unit 130.

First, in the example of FIG. 21, the electronic shutter turns on at time t1. After the electronic shutter has turned on, the first light emitting element 121 turns on to start light emission. The first light emitting element 121 turns on to start light emission at a point later than time t1. That is, the first light emitting element 121 is controlled so that the first light emitting element 121 starts light emission after the electronic shutter has turned on. With this configuration, the light from the first light emitting element 121 is emitted to the excrement or the like, and then, the light receiving unit 130 receives the reflected light from the excrement or the like. In this manner, the toilet system 1 collects analog data of excrement corresponding to the light emitted by the first light emitting element 121.

After the electronic shutter has turned off, the AD Converter 341 turns on to perform conversion of the analog data detected by the light receiving unit 130 into digital data. That is, the AD Converter 341 is controlled so that the AD Converter 341 converts the analog data detected by the light receiving unit 130 into digital data in a state where the electronic shutter is OFF (closed).

After the AD Converter 341 is turned off, the data is transferred to the first memory 344. That is, the arithmetic processing device 342 is controlled so as to start data transfer to the first memory 344 after completion of the conversion of the analog data to the digital data by the AD Converter 341. With this configuration, digital data of excrement corresponding to the light emitted by the first light emitting element 121 is stored in the first memory 344. In this manner, the toilet system 1 collects digital data of excrement corresponding to the light emitted by the first light emitting element 121.

After completion of the data transfer to the first memory 344, the electronic shutter turns on again. In the example of FIG. 21, the electronic shutter turns on at time t2. After the electronic shutter has turned on, the first light emitting element 121 turns on again to start light emission. The first light emitting element 121 turns on again to start light emission at a point later than time t2. That is, the first light emitting element 121 is controlled so that the first light emitting element 121 starts light emission after the electronic shutter has turned on. In the standby mode, the similar process will be repeated as illustrated in FIG. 21.

<9-4. Measurement Mode>

Figure 22:
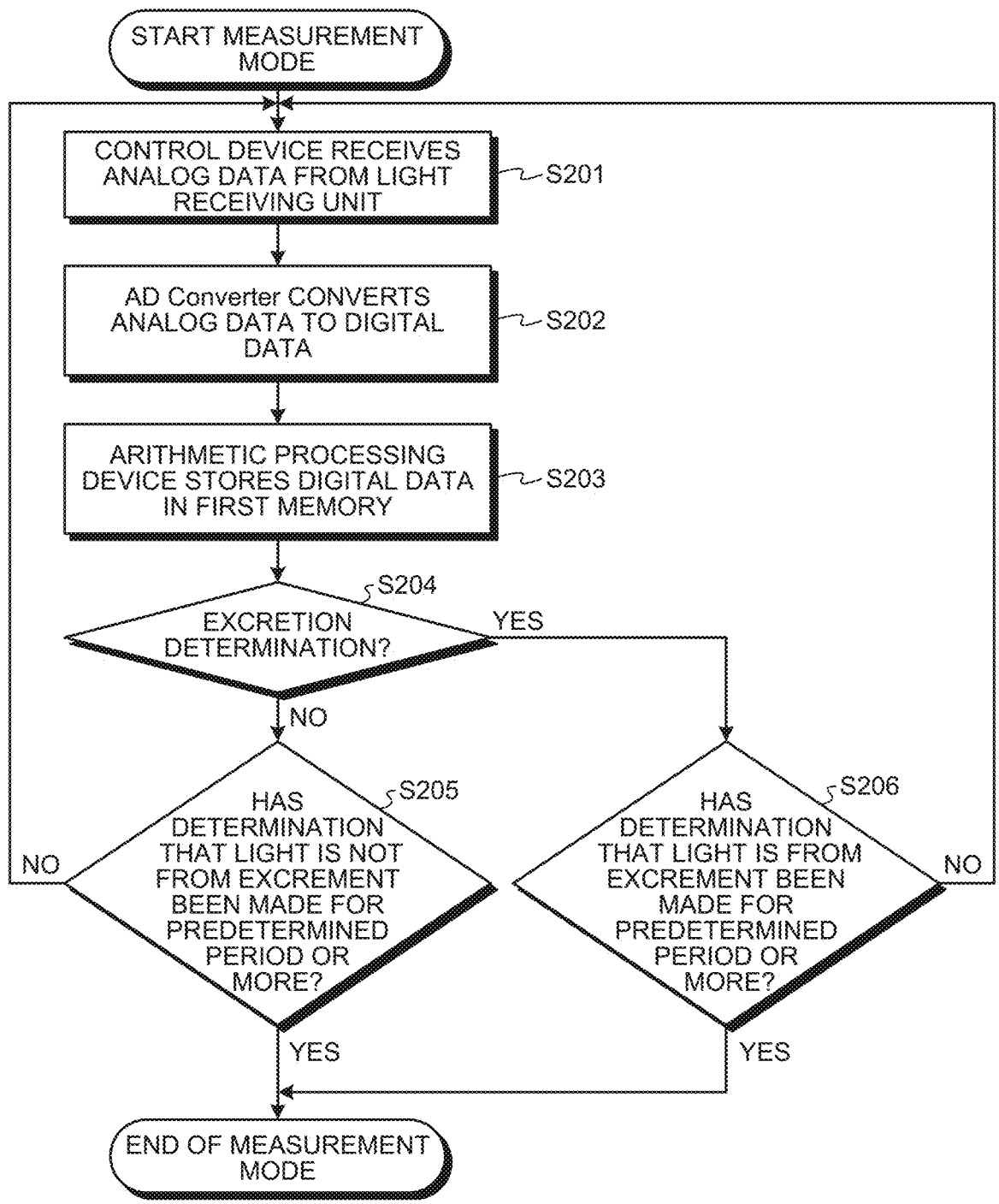
FIG. 22 is a flowchart illustrating an example of a processing procedure in a measurement mode.
Figure 23:
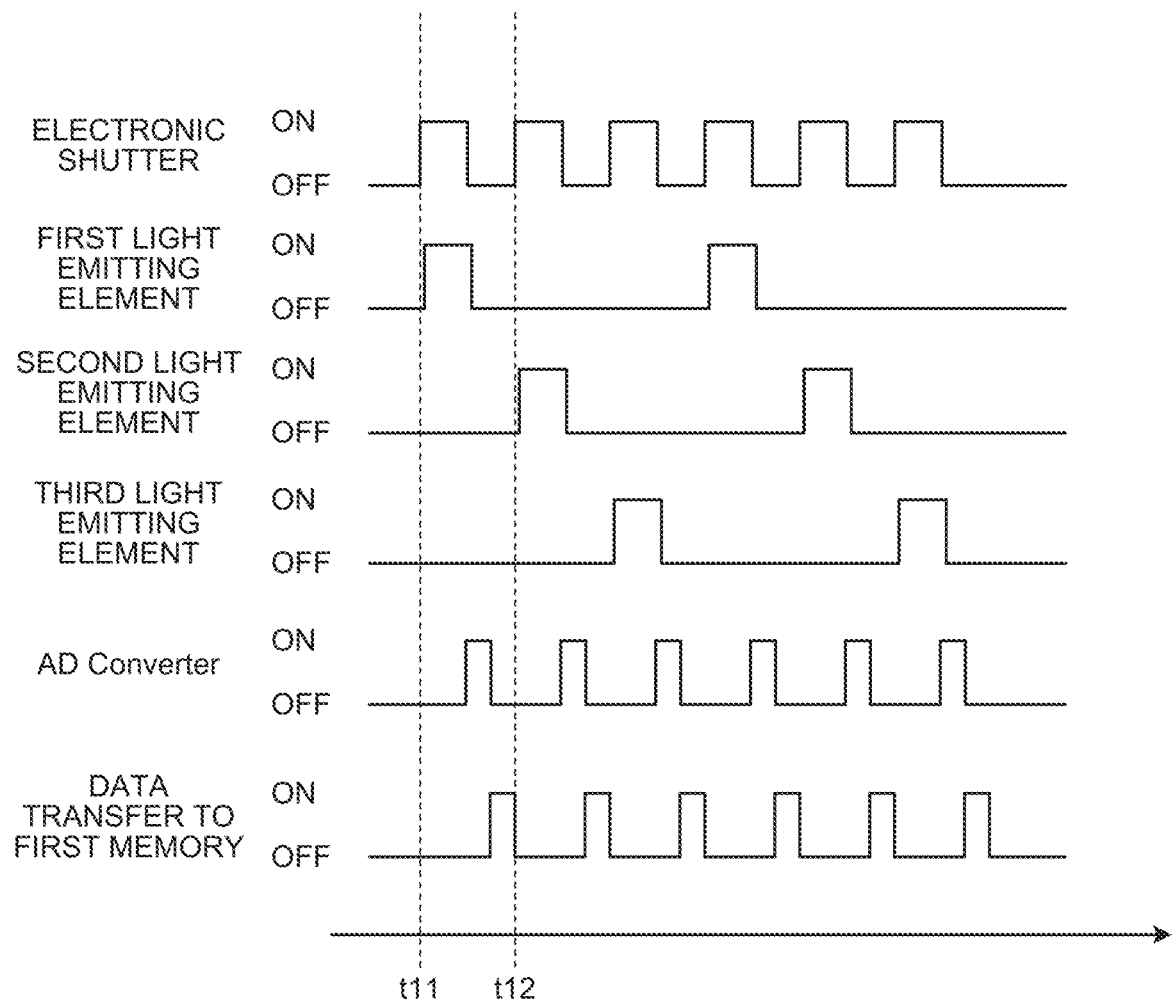
FIG. 23 is a diagram illustrating an example of a time chart in a measurement mode.

Next, the specific operation of the measurement mode will be described with reference to FIGS. 22 and 23. FIG. 22 is a flowchart illustrating the example of a processing procedure in the measurement mode. FIG. 23 is a diagram illustrating the example of a time chart in the measurement mode.

First, the flow of processes in the measurement mode will be described with reference to FIG. 22. As illustrated in FIG. 22, in the toilet system 1, the control device 34 receives analog data from the light receiving unit 130 (Step S201).

Next, in the toilet system 1, the AD Converter 341 converts analog data into digital data (Step S202). For example, the AD Converter 341 converts analog data obtained by deleting data in a predetermined range from analog data into digital data. For example, the AD Converter 341 converts analog data obtained by deleting data in a predetermined range at both ends from analog data into digital data. Subsequently, in the toilet system 1, the arithmetic processing device 342 stores the digital data in the first memory 344 (Step S203). The arithmetic processing device 342 stores the digital data converted by the AD Converter 341 in the first memory 344. The arithmetic processing device 342 may delete a part of the converted digital data and store the remaining digital data in the first memory 344.

Subsequently, the toilet system 1 makes an excretion determination (Step S204). For example, in the toilet system 1, the control device 34 makes an excretion determination. For example, the control device 34 makes the excretion determination using an excretion determination program stored in the ROM 343 and digital data stored in the first memory 344. For example, the control device 34 makes the excretion determination by determining whether the output value of the light receiving element 132 has varied by a predetermined value or more with respect to the initial data acquired after the user is seated. The excretion determination in Step S204 may be similar to the excretion determination in Step S104 in the standby mode in FIG. 21.

When the toilet system 1 has determined that excretion has not occurred (Step S204: No), the arithmetic processing device 342 determines whether the determination that the light is not from the excrement has been made for a predetermined period or more (Step S205). For example, in the toilet system 1, the control device 34 determines whether the determination that the light is not from the excrement has been made for a predetermined period or more.

When the toilet system 1 has determined that the determination that the light is not from the excrement has been made for a predetermined period or more (Step S205: Yes), the toilet system 1 ends the measurement mode. When the toilet system 1 has determined that the period of determination that the light is not from the excrement is a predetermined period or more, the toilet system 1 ends the measurement mode assuming that the user's excretion is temporarily stopped or finished. Subsequently, in the toilet system 1, the arithmetic processing device 342 transfers data to the second memory 20, and then shifts to the standby mode again. For example, the arithmetic processing device 342 transmits the digital data stored in the first memory 344 to the second memory 20, and then shifts to the standby mode again.

Furthermore, when the toilet system 1 has determined that the determination that the light is not from the excrement has not been made for a predetermined period or more (Step S205: No), the toilet system 1 returns to Step S201 and repeats the process. When the toilet system 1 has determined that the determination that the light is not from the excrement has been made for less than a predetermined period, the toilet system 1 maintains the measurement mode assuming that the user's excretion will possibly resume soon.

In contrast, when having determined that excretion has occurred (Step S204: Yes), the toilet system 1 determines whether the determination that the light is from the excrement has been made for a predetermined period or more (Step S206). For example, in the toilet system 1, the control device 34 determines whether the determination that the light is from the excrement has been made for a predetermined period or more.

When the toilet system 1 has determined that the determination that the light is from the excrement has been made for a predetermined period or more (Step S206: Yes), the toilet system 1 ends the measurement mode. When the toilet system 1 determines that the determination that the light is from the excrement has been made for a predetermined period or more, the toilet system 1 ends the measurement mode assuming that sufficient information regarding the user's excrement has been collected. Subsequently, in the toilet system 1, the arithmetic processing device 342 transfers data to the second memory 20, and then shifts to the standby mode again. For example, the arithmetic processing device 342 transmits the digital data stored in the first memory 344 to the second memory 20, and then shifts to the standby mode again.

Furthermore, when the toilet system 1 has determined that the determination that the light is from the excrement has not been made for a predetermined period or more (Step S206: No), the toilet system 1 returns to Step S201 and repeats the process. When the toilet system 1 has determined that the determination that the light is from the excrement has been made for less than a predetermined period, the toilet system 1 maintains the measurement mode assuming that sufficient information regarding the excrement of the user has not been collected.

Next, a time chart of the measurement mode will be described with reference to FIG. 23. As illustrated in FIG. 23, in the measurement mode, various configurations and processes of the toilet system 1 are controlled. For example, processes of the configuration of the electronic shutter of the light receiving unit 130, the first light emitting element 121, the second light emitting element 121, the third light emitting element 121, the AD Converter 341, or the like, and the data transfer to the first memory 344, are controlled. The description of the points similar to FIG. 21 will be omitted as appropriate.

The first light emitting element 121 emits light having a wavelength in the invisible light region or a wavelength close to the invisible light region. Furthermore, the second light emitting element 121 and the third light emitting element 121 emit light having a wavelength in the visible light region. The second light emitting element 121 and the third light emitting element 121 emit light having different wavelengths. The control illustrated in the time chart of FIG. 23 may be performed by the control device 34.

The electronic shutter is switched between ON and OFF at predetermined intervals. In the example of FIG. 23, the interval from ON to the next ON of the electronic shutter is controlled to a period (second period) between time t11 and time t12. The second period illustrated in FIG. 23 may be the same as the first period illustrated in FIG. 21.

First, in the example of FIG. 23, the electronic shutter turns on at time t11. After the electronic shutter has turned on, the first light emitting element 121 turns on to start light emission. The first light emitting element 121 turns on to start light emission at a point later than time t11. With this configuration, the light from the first light emitting element 121 is emitted to the excrement or the like, and then, the light receiving unit 130 receives the reflected light from the excrement or the like. In this manner, the toilet system 1 collects analog data of excrement corresponding to the light emitted by the first light emitting element 121.

After the electronic shutter has turned off, the AD Converter 341 turns on to perform conversion of the analog data detected by the light receiving unit 130 into digital data. After the AD Converter 341 is turned off, the data is transferred to the first memory 344. With this configuration, digital data of excrement corresponding to the light emitted by the first light emitting element 121 is stored in the first memory 344. In this manner, the toilet system 1 collects digital data of excrement corresponding to the light emitted by the first light emitting element 121.

After completion of the data transfer to the first memory 344, the electronic shutter turns on again. In the example of FIG. 23, the electronic shutter turns on at time t12. After the electronic shutter has turned on, the second light emitting element 121 turns on to start light emission. The second light emitting element 121 turns on to start light emission at a point later than time t12. That is, the second light emitting element 121 is controlled so that the second light emitting element 121 starts light emission after the electronic shutter has turned on. With this configuration, the light from the second light emitting element 121 is emitted to the excrement or the like, and then, the light receiving unit 130 receives the reflected light from the excrement or the like. In this manner, the toilet system 1 collects analog data of excrement corresponding to the light emitted by the second light emitting element 121.

After the electronic shutter has turned off, the AD Converter 341 turns on to perform conversion of the analog data detected by the light receiving unit 130 into digital data. After the AD Converter 341 is turned off, the data is transferred to the first memory 344. With this configuration, digital data of excrement corresponding to the light emitted by the second light emitting element 121 is stored in the first memory 344. In this manner, the toilet system 1 collects digital data of excrement corresponding to the light emitted by the second light emitting element 121.

In the measurement mode, the similar process will be repeated as illustrated in FIG. 23. For example, in the subsequent repetition, the toilet system 1 causes the third light emitting element 121 to emit light and collects digital data regarding excrement corresponding to the light emitted by the third light emitting element 121.

<9-5. Data>

Figure 24:
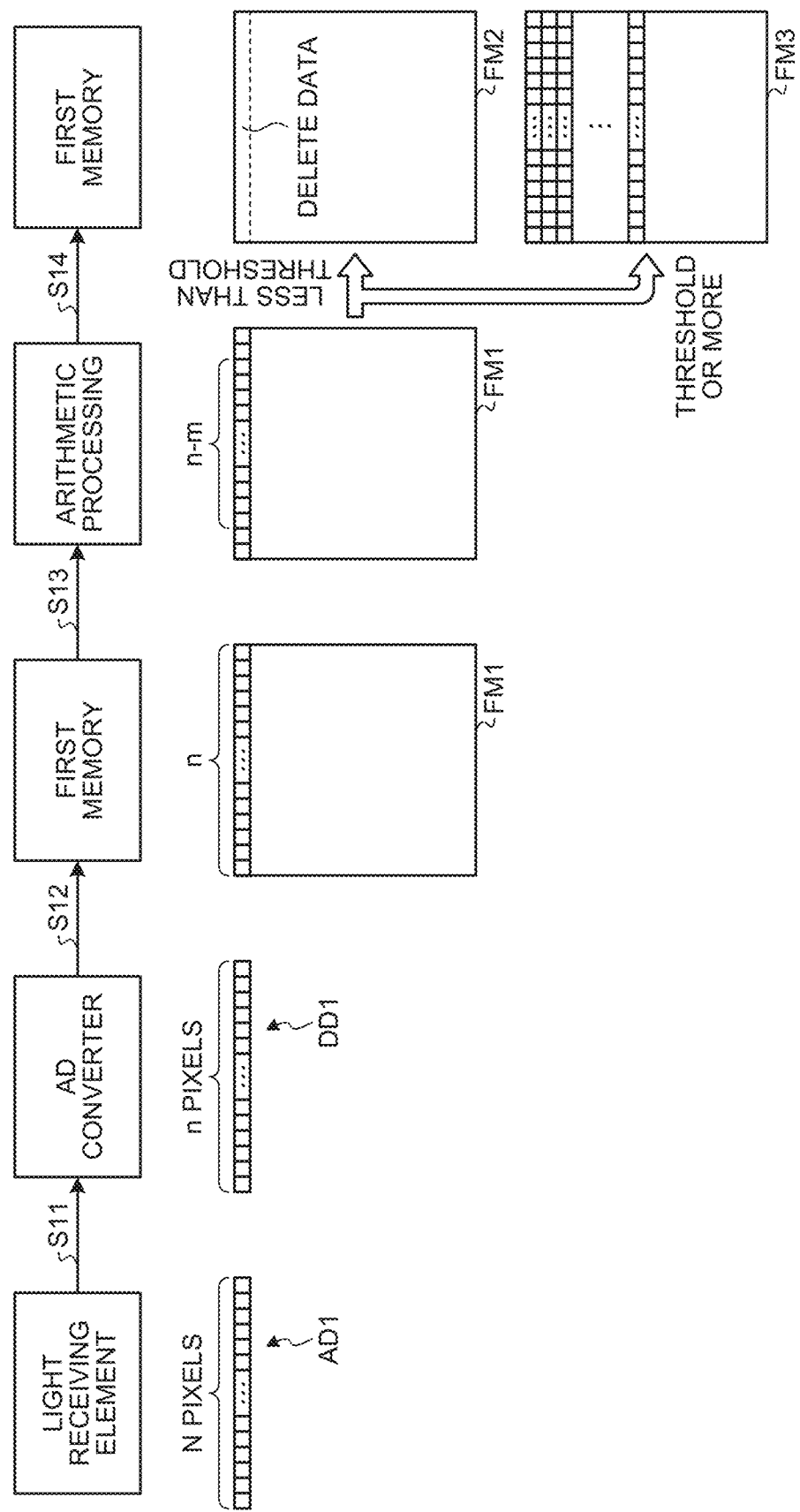
FIG. 24 is a diagram illustrating an example of data in the process of excretion information collection.

Here, the data in the process of collecting excretion information will be described with reference to FIG. 24. FIG. 24 is a diagram illustrating an example of data in the process of collecting excretion information. The following will describe only the configuration and processes necessary for a flow of data, and thus, will omit descriptions of the light emission of the light emitting unit 120 or the like. Furthermore, although the processes in the measurement mode will be described below as an example, the processes in the standby mode may be performed in a similar manner.

First, the light receiving element 132 of the light receiving unit 130 performs detection. The light receiving unit 130 detects analog data AD1 of N pixels (N is an arbitrary number). The light receiving unit 130 transmits the detected analog data AD1 to the AD Converter 341 (Step S11).

The AD Converter 341 converts analog data AD1 formed with analog values into digital data formed with digital values. For example, the arithmetic processing device 342 judges which of the pixels is to undergo AD conversion by the AD Converter 341, and determines the pixel to be converted by the AD Converter 341 among the N pixels of analog data AD1. The arithmetic processing device 342 determines a value "n" which is N or less, and determines the number of pixels "n" to be converted by the AD Converter 341. For example, the arithmetic processing device 342 can reduce the amount of data to be stored in the first memory 344 by determining a value of N or less as the "n".

The AD Converter 341 AD-converts the analog data of a predetermined number of pixels (n pixels) out of the analog data AD1 of N pixels under the control of the arithmetic processing device 342. The AD Converter 341 performs AD conversion of analog data of n pixels out of the analog data AD1 of N pixels to generate digital data DD1.

The AD Converter 341 stores the digital data DD1 obtained by AD conversion in the first memory 344 (Step S12). The AD Converter 341 stores the digital data DD1 in the first memory 344 under the control of the arithmetic processing device 342. As illustrated in a storage region FM1, the first memory 344 stores digital data of n pixels.

The arithmetic processing device 342 performs arithmetic processing on the digital data of n pixels stored in the first memory 344 (Step S13). For example, the arithmetic processing device 342 the excretion determination on the digital data of n pixels (for example, digital data DD1) stored in the first memory 344. For example, the arithmetic processing device 342 performs a threshold determination on n-m predetermined pixels among the digital data of n pixels. Note that the arithmetic processing device 342 may perform threshold determination on the digital data of n pixels.

The arithmetic processing device 342 executes processes on the first memory 344 based on the result of the threshold determination (Step S14). When the number of pixels in which the output value of the light receiving element 132 has varied by a predetermined value or more is less than the threshold with respect to the initial data, the arithmetic processing device 342 deletes the data as illustrated in a storage region FM2. That is, when it is determined that the light received by the light receiving element 132 is not the light reflected from the excrement, the arithmetic processing device 342 deletes the digital data (for example, digital data DD1) stored in the first memory 344. In this manner, the arithmetic processing device 342 deletes data temporarily stored in the first memory 344 when the data is not the data representing the light reception data regarding the light reflected from the excrement.

Furthermore, when the number of pixels in which the output value of the light receiving element 132 has varied by a predetermined value or more is the threshold or more with respect to the initial data, the arithmetic processing device 342 accumulates the data as illustrated in a storage region FM3. That is, when it is determined that the light received by the light receiving element 132 is the light reflected from the excrement, the arithmetic processing device 342 would not delete the digital data (for example, digital data DD1) stored in the first memory 344. With this configuration, the arithmetic processing device 342 accumulates data in the first memory 344 until a predetermined time or a predetermined amount is reached, as illustrated in the storage region FM3.

<10. Data Analysis>

Now, data analysis on properties such as the shape and color of excrement (feces) will be described with reference to FIGS. 25 and 26. The following will describe an exemplary case where the control device 34 of the toilet system 1 executes a data analysis process related to properties such as the shape and color of excrement (feces).

<10-1. Shape of Excrement>

First, data analysis on the shape of excrement will be described with reference to FIG. 25. FIG. 25 is a diagram illustrating an example of data analysis on the shape of excrement.

Figure 25:
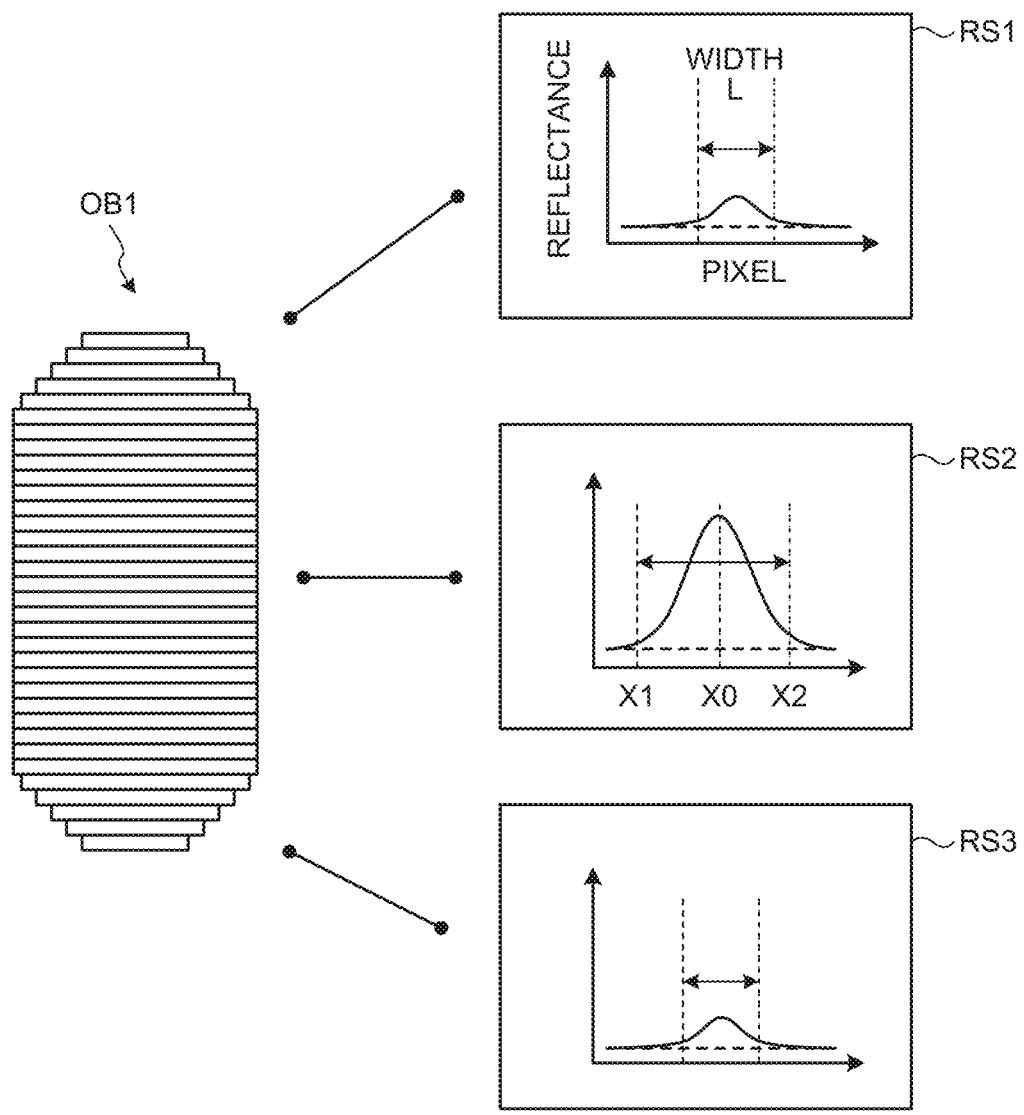
FIG. 25 is a diagram illustrating an example of data analysis regarding excrement shapes.

FIG. 25 includes an object OB1 schematically illustrating the feces (excrement) to be detected (measured), and illustrates outline of how the shape of the excrement is measured (observed) using the object OB1 as an example. The following description defines the longitudinal direction of the object OB1 as a vertical direction, and defines the direction (short direction) orthogonal to the longitudinal direction, as a lateral direction. The object OB1 like this falls in the vertical direction.

Each of measurement results RS1 to RS3 is a graph illustrating a relationship between individual pixels and their reflectance. Each of the measurement results RS1 to RS3 illustrates measurement results corresponding to individual positions in the vertical direction of the object OB1. The measurement result RS1 indicates a measurement result corresponding to an upper end of the object OB1. A measurement result RS2 illustrates a measurement result corresponding to a central part of the object OB1 in the vertical direction. Measurement result RS3 illustrates a measurement result corresponding to a lower end of the object OB1.

The control device 34 detects the presence or absence of the reflectance of each of pixels of the light received by the light receiving element 132. The control device 34 obtains a peak value from the pixels having reflection. In each of the measurement results RS1 to RS3, the central part has the peak value. For example, the control device 34 specifies, in the measurement result RS2, that a pixel X0 is an image having a peak value.

The control device 34 compares the difference in reflectance between the pixel having the peak value and the adjacent pixel. When the reflectance that is a predetermined value or more or a predetermined value or less has been confirmed, the control device 34 estimates that the light is the reflected light from the excrement. The control device 34 performs a similar process regarding the color.

In a case where the light is confirmed to be the reflected light from the excrement, the control device 34 further performs the similar process on the pixels adjacent to the pixel. With this process, the control device 34 identifies the edge of the excrement and estimates the width of the excrement. For example, the control device 34 estimates that the range from a pixel X1 to an image X2 is excrement in the measurement result RS2. In the measurement result RS1, the control device 34 estimates that the width L narrower than the range from the pixel X1 to the image X2 in the measurement result RS2 is the width of the excrement. The control device 34 analyzes the shape of excrement by stacking the measurement results RS1 to RS3 or the like. In the example of FIG. 25, the control device 34 analyzes that the shape has the greatest width in a portion corresponding to the measurement result RS2 (center), with the width decreasing toward the portion corresponding to the measurement result RS1 (upper end) and the portion corresponding to the measurement result RS3 (lower end).

By the above-described process, the object OB1 falling from the user toward the bowl unit 8 of the toilet bowl 7 is detected. For example, the object OB1, which is a falling excrement, is detected in the order from the bottom to the top by passing in the order of the lower end, the center, and the upper end in front of the light emitting unit 120 and the light receiving unit 130. Specifically, the object OB1, which is a falling excrement, is detected in the order of measurement result RS3, measurement result RS2, and measurement result RS1. With this process, the toilet system 1 can detect excrement (feces) falling from the user. The toilet system 1 may detect the excrement after reaching the water in the bowl unit 8 after the fall, not limited to the excrement that is falling.

<10-2. Color of Excrement>

First, data analysis on the color of excrement will be described with reference to FIG. 26. FIG. 26 is a diagram illustrating an example of data analysis regarding excrement colors. FIG. 26 is a diagram illustrating an example of data analysis regarding detection of blood contained in excrement. Note that description on points similar to FIG. 25 will be appropriately omitted by adding same reference numerals.

Figure 26:
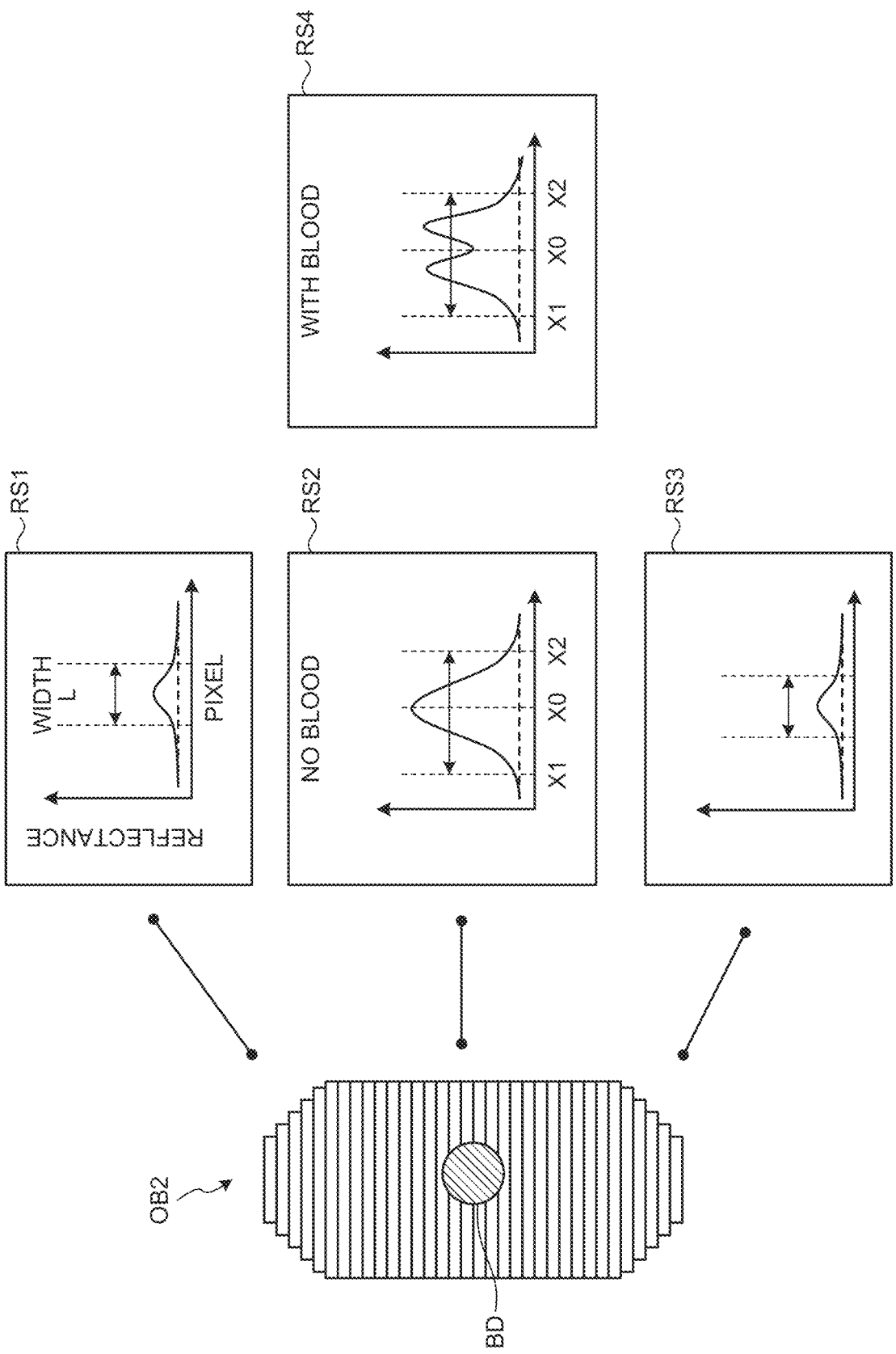
FIG. 26 is a diagram illustrating an example of data analysis regarding excrement colors.

An object OB2 in FIG. 26 illustrates virtual feces (excrement). The object OB2 differs from the object OB1 in FIG. 25 in that a blood region BD is contained in the center. The measurement results RS1 to RS3 illustrated in FIG. 26 respectively correspond to the measurement results RS1 to RS3 of the object OB1 in FIG. 25 without the blood region BD.

The control device 34 specifies a pixel having a peak value for light of a wavelength having reflectance specific to blood among beams of light of a plurality of wavelengths emitted to the object OB2 which is excrement. For example, the control device 34 specifies a pixel having a peak value for 670 nm light having reflectance specific to blood among beams of light of a plurality of wavelengths emitted to the object OB2 which is excrement.

Thereafter, the control device 34 calculates the reflectance corresponding to the light of another wavelength detected by the pixel having the peak value. The control device 34 estimates the color from the ratio of the reflectance to other wavelengths including 670 nm detected by the pixel. The measurement result RS4 in FIG. 26 illustrates the measurement result for a portion including the blood region BD such as the object OB2. For example, the measurement result RS4 in FIG. 26 illustrates the measurement result when light in a region not including 670 nm (for example, the first wavelength region) is emitted to the portion of the object OB2 containing the blood region BD.

The wavelength having a reflectance specific to blood is not limited to 670 nm, and may be in the range of 600 nm to 800 nm. This is because, when blood is attached to the feces, the reflectance for the blood color is detected, in this wavelength band, more significantly than the feces color.

Figure 27:
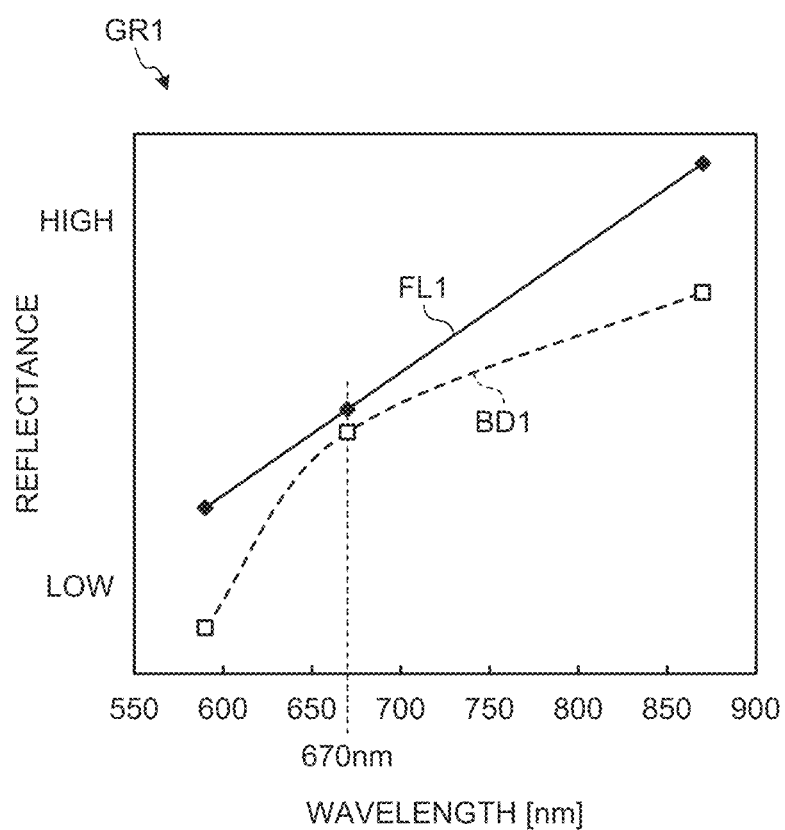
FIG. 27 is a diagram illustrating an example of a relationship between excrement and blood.

Here, a relationship between excrement and blood will be described with reference to FIG. 27. FIG. 27 is a diagram illustrating an example of a relationship between excrement and blood. Graph GR1 illustrated in FIG. 27 is a diagram illustrating a relationship between the reflection of feces and the reflection of blood attached to feces, for various wavelengths.

A line FL1 in Graph GR1 of FIG. 27 illustrates the reflectance of various wavelengths (approximately 600 nm to approximately 870 nm) for the excrement (feces). As illustrated by the line FL1 in FIG. 27, in the case of excrement (feces), the longer the wavelength, the higher the reflectance. As illustrated by the line FL1 in FIG. 27, in the case of excrement (feces), the reflectance around 600 nm is the lowest, and the reflectance around 870 nm is the highest. In addition, a line BD1 in Graph GR1 of FIG. 27 illustrates the reflectance of various wavelengths (approximately 600 nm to approximately 870 nm) for the blood attached to the feces. As illustrated in the line BD1 in FIG. 27, in the case of blood (blood) attached to the feces, the reflectance near 670 nm has the smallest difference from the line FL1, and the difference from the line FL1 increases as the distance from 670 nm increases.

In the graph GR1 in FIG. 27, the ratio of the reflectance of blood attached to the feces to the reflectance of the feces is highest near 670 nm and decreases as separating from 670 nm. In this manner, in the graph GR1 illustrated in FIG. 27, the ratio of the reflectance of blood attached to feces to the reflectance of feces is large at the wavelength of 670 nm, while the ratio of the reflectance of blood to the reflectance of feces is small at the wavelength of 870 nm.

Figure 28:
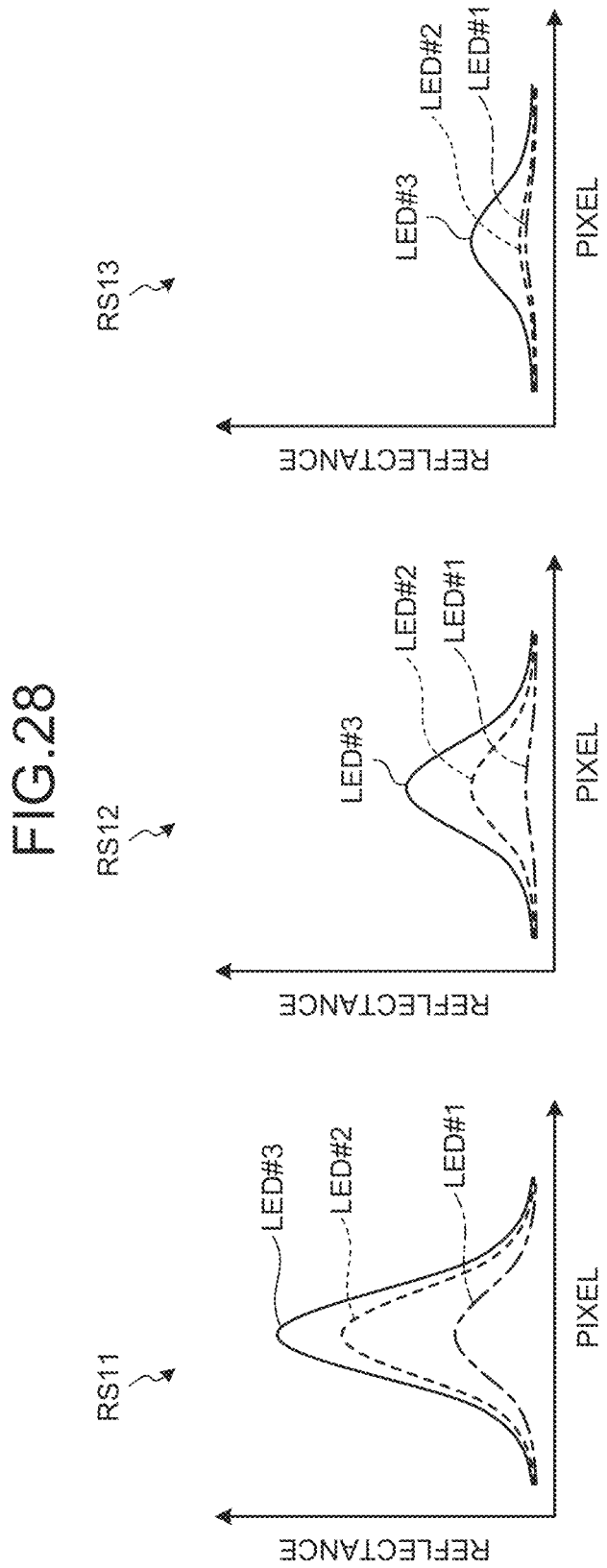
FIG. 28 is a diagram illustrating an example of data analysis regarding excrement colors.
Figure 29:
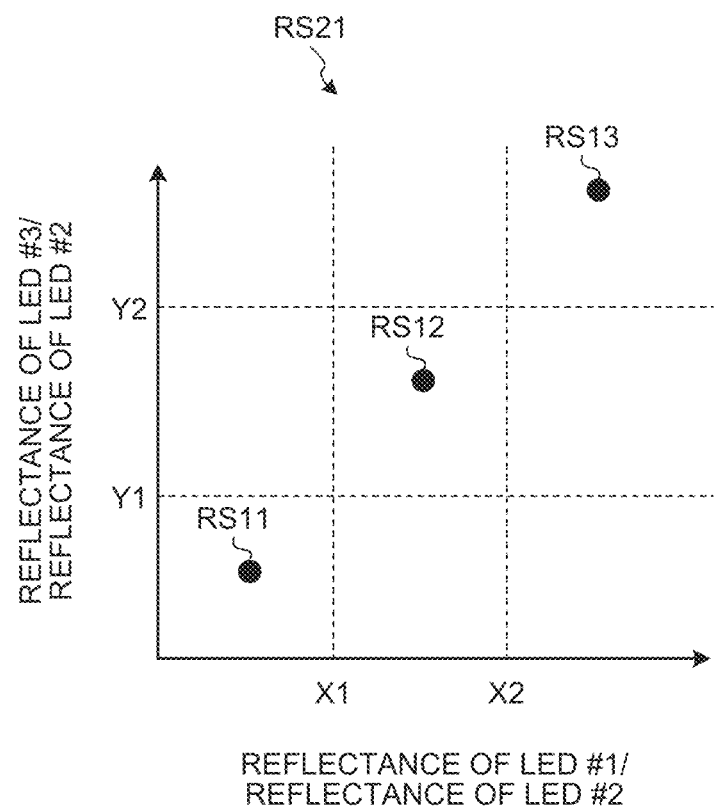
FIG. 29 is a diagram illustrating an example of data analysis regarding excrement colors.

Accordingly, the toilet system 1 can detect blood contained in excrement based on the ratio of the reflectance at various wavelengths as described above. In addition, the toilet system 1 can analyze the color of excrement based on the ratio of the reflectance at various wavelengths as described above. This point will be described with reference to FIGS. 28 and 29. FIGS. 28 and 29 are diagrams illustrating an example of data analysis regarding excrement colors.

The measurement results RS11 to RS13 in FIG. 28 illustrate the measurement results when excrement (feces) of different colors is to be measured. For example, the color of the excrement (feces) to be measured may be darker in the order of measurement results RS11, RS12, and RS13. For example, measurement results may be such that: the measurement result RS11 is the measurement result of yellowish brown excrement (feces); the measurement result RS12 is the measurement result of brown excrement (feces); and the measurement result RS13 is the measurement result of dark brown excrement (feces).

In addition, each of LED #1, LED #2, and LED #3 illustrated in the measurement results RS11 to RS13 in FIG. 28 is the light emitting element 121 that emits light. Each of curves of LED #1, LED #2, and LED #3 illustrates a relationship between the pixel and the reflectance. Each of LED #1, LED #2, and LED #3 may correspond to any of the first light emitting element, the second light emitting element, or the third light emitting element. For example, LED #1 may be the third light emitting element, LED #2 may be the second light emitting element, and LED #3 may be the first light emitting element. The above is an example, and each of LED #1, LED #2, and LED #3 may be a light emitting element that emits light in any wavelength region.

For example, the darker the color of feces, the lower the reflectance at various wavelengths. In the example of FIG. 28, among the measurement results RS11 to RS13, the reflectance at various wavelengths in the measurement result RS13 in which the color of excrement (feces) is the darkest becomes small, with a large ratio between individual levels of reflectance.

On the other hand, for example, the lighter the color of feces, the greater the reflectance at various wavelengths. In the example of FIG. 28, among the measurement results RS11 to RS13, the reflectance at various wavelengths in the measurement result RS11 in which the color of excrement (feces) is the lightest becomes small, with a small ratio between individual levels of reflectance. For example, the closer to a lighter color, the higher the reflection of the light at various wavelengths, leading to the small difference between individual levels of reflectance at various wavelengths.

In view of this, the toilet system 1 can classify the color of excrement (feces) by analysis based on the relationship between the wavelength and the reflectance as described above. For example, the toilet system 1 classifies the measurement results RS11 to RS13 based on the reflectance ratio for each of LED #1, LED #2, and LED #3, as illustrated in a classification result RS21 illustrated in FIG. 29, thereby classifying the color of excrement (feces) in each of measurements.

For example, the toilet system 1 classifies the color of excrement (feces) in each of the measurement results RS11 to RS13 by using the ratio between the reflectance of LED #1 to the reflectance of LED #2, or the ratio between the reflectance of LED #3 and the reflectance of LED #2. For example, the toilet system 1 classifies the color of excrement (feces) in each of measurements based on the positions of measurement results RS11 to RS13, with "reflectance of LED #1/reflectance of LED #2" defined as an X-axis and "reflectance of LED #3/reflectance of LED #2" defined as a Y-axis. For example, when the result is less than X1 in the X-axis direction and less than Y1 in the Y-axis direction, the toilet system 1 classifies the color of excrement (feces) in the measurement as "yellowish brown". For example, when the result is X1 or more and less than X2 in the X-axis direction and Y1 or more and less than Y2 in the Y-axis direction, the toilet system 1 classifies the color of excrement (feces) in the measurement as "brown". For example, when the result is X2 or more in the X-axis direction and Y2 or more in the Y-axis direction, the toilet system 1 classifies the color of excrement (feces) in the measurement as "dark brown". The above is an example, and the toilet system 1 may classify the color of excrement (feces) in each of measurements by any method.

<11. Falling Position of Excrement>

Figure 30:
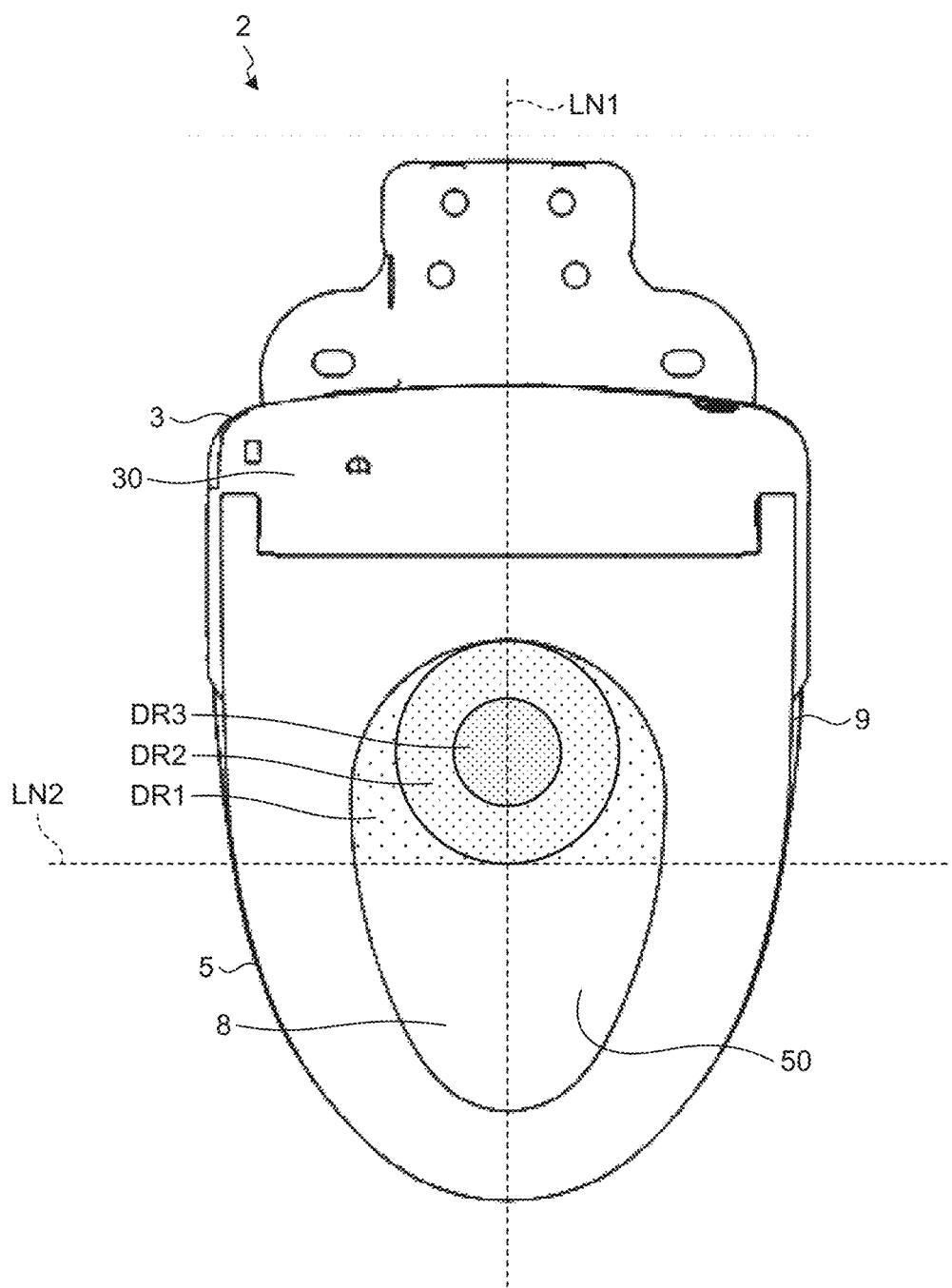
FIG. 30 is a diagram illustrating an example of a virtual falling position of feces.

From here, a position (virtual falling position) at which the excrement (feces) is expected to fall will be described with reference to FIG. 30. FIG. 30 is a diagram illustrating an example of a virtual falling position of feces. As described above, the side of the toilet seat 5 on which the main body 3 is located is set as a rear side, while the side of the toilet seat 5 away from the main body 3 is set as a front side.

The toilet system 1 may set various positions (ranges) as virtual falling positions of feces. For example, the toilet system 1 may set the range of the opening 50 of the toilet seat 5 in the plan view of the toilet seat 5 as the virtual falling position of the feces. As illustrated below, the toilet system 1 may set a predetermined range within the range of the opening 50 as a virtual falling position of feces.

For example, the toilet system 1 may set a range DR1 in FIG. 30 as the virtual falling position of feces. Specifically, the toilet system 1 may set the range DR1 located on the rear side when the opening 50 of the toilet seat 5 is divided into the front side and the rear side, as the virtual falling position of feces. The toilet system 1 may set the range DR1 located on the rear side when the opening 50 is divided into front and rear portions with a center line LN2 passing through the center of the opening 50 of the toilet seat 5 in the front-rear direction, as the virtual falling position of feces.

For example, it is preferable that the toilet system 1 sets a range DR2 in FIG. 30 as the virtual falling position of feces. Specifically, the toilet system 1 may set the range DR2 surrounded by a perfect circle having a diameter connecting the center of the center line LN2 that divides the opening 50 of the toilet seat 5 into the front side and the rear side, and a rear end at the center of the horizontal direction of the opening 50 of the toilet seat 5, as the virtual falling position of feces. Among the center line LN1 passing through a rear end (first point) at the center in the horizontal direction of the opening 50 of the toilet seat 5 and passing through the center (second point) of a center line LN2, the range DR2 surrounded by a circle centered on a midpoint between the first point and the second point may be set as the virtual falling position of feces, by the toilet system 1.

For example, it is more preferable that the toilet system 1 sets a range DR3 in FIG. 30 as the virtual falling position of feces. Specifically, the toilet system 1 may set the range DR3 surrounded by a perfect circle with a radius of 30 mm centered on a position 70 mm forward from the rear end in the center of the horizontal direction of the opening 50 of the toilet seat 5, as the virtual falling position of feces. Among the center line LN1 passing through a rear end (first point) at the center in the horizontal direction of the opening 50 of the toilet seat 5 and passing through the center (second point) of a center line LN2, the range DR3 surrounded by a perfect circle having a radius of 30 mm centered on a position 70 mm forward from the first point may be set as the virtual falling position of feces, by the toilet system 1. The above is an example, and the toilet system 1 may set any range as the virtual falling position of feces.

<12. Relationship Between Amount of Light and Sampling Rate>

Figure 31:
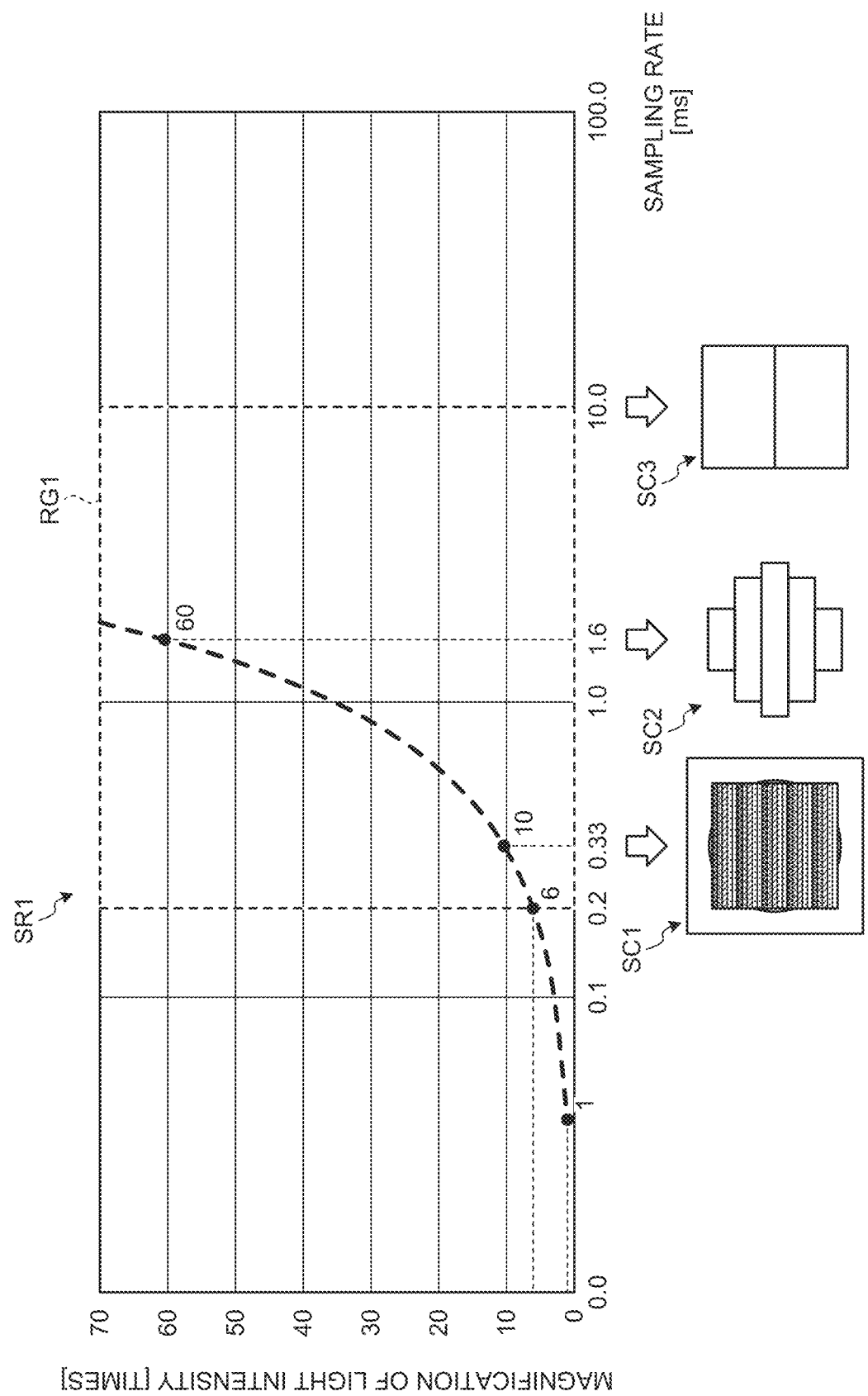
FIG. 31 is a diagram illustrating a relationship between the amount of light and the sampling rate.

From here, a relationship between the light emitted by the light emitting unit 120 and other configurations will be described with reference to FIG. 31. FIG. 31 is a diagram illustrating a relationship between the amount of light and the sampling rate. Although description using FIG. 31 is an exemplary case where the toilet system 1 is used as a target, it is also allowable to use the toilet systems 1A and 1B may be used as a target, not limited to the toilet system 1. The description of points similar to various configurations and processes described above will be appropriately omitted by adding the similar reference numerals.

Graph SR1 illustrated in FIG. 31 is a diagram illustrating measurement results illustrating the amount of light at each of sampling rates. The measurement condition of Graph SR1 illustrated in FIG. 31 is, for example, an excrement falling speed of 1.23 m/s at a position 40 mm below the anus of the user seated on the toilet seat 5 of the toilet system 1.

In the example of FIG. 31, the sampling rate indicates the time in milliseconds (ms). For example, the sampling rate indicates the interval (time) from the start of execution of the light reception control to the execution of the subsequent light reception control. For example, in the time chart illustrated in FIGS. 21 and 23, the sampling rate indicates the interval (time) from the point where the electronic shutter turns on first to the point where the electronic shutter turns on next. In the example of FIG. 21, the interval (time) from time t1 to time t2 corresponds to the sampling rate. Furthermore, in the example of FIG. 23, the interval (time) from time t11 to time t12 corresponds to the sampling rate. The amount of light illustrated in FIG. 31 indicates the amount of light when one light emission is performed at the corresponding sampling rate (time), for example.

Graph SR1 illustrated in FIG. 31 illustrates the amount of light at each of sampling rates when the amount of light at a predetermined time (for example, 0.038 milliseconds) with a sampling rate lower than 0.2 milliseconds is set to "1".

In the example illustrated in FIG. 31, when the sampling rate is 0.2 milliseconds, the amount of light is "6". That is, when the sampling rate is 0.2 milliseconds, the amount of light is six times that of the predetermined time. In this case, the control device 34 controls the interval (time) from the point where the electronic shutter turns on to the point where the electronic shutter turns on next, to 0.2 milliseconds. That is, the control device 34 controls the execution at a speed (sampling rate) of 5000 times/sec or less.

Furthermore, in the example illustrated in FIG. 31, when the sampling rate is 0.33 milliseconds, the amount of light is "10". That is, when the sampling rate is 0.33 milliseconds, the amount of light is 10 times that of the predetermined time. In this case, the control device 34 controls the interval (time) from the point where the electronic shutter turns on to the point where the electronic shutter turns on next, to 0.33 milliseconds. When the sampling rate is 0.33 milliseconds, as illustrated in a scanned image SC1, five types of beams of light are scanned (emitted) five times in a 10 mm diameter (φ) region.

Furthermore, in the example illustrated in FIG. 31, when the sampling rate is 1.6 milliseconds, the amount of light is "60". That is, when the sampling rate is 1.6 milliseconds, the amount of light is 60 times that of the predetermined time. In this case, the control device 34 controls the interval (time) from the point where the electronic shutter turns on to the point where the electronic shutter turns on next, to 1.6 milliseconds. When the sampling rate is 1.6 milliseconds, as illustrated in a scanned image SC2, one type of beam of light is scanned (emitted) five times in a 10 mm diameter (φ) region.

Furthermore, when the sampling rate is 10 milliseconds, as illustrated in a scanned image SC3, one type of beam of light is scanned (emitted) twice in a 10 mm diameter (φ) region.

For example, in the toilet system 1, the sampling rate is set to a value within a range RG1 that is 0.2 milliseconds or more and 10 milliseconds or less. That is, in the toilet system 1, the sampling rate is set to 0.2 milliseconds or more and 10 milliseconds or less. The control device 34 controls the interval (sampling rate) from the point where the electronic shutter turns on to the point where the electronic shutter turns on next, to 0.2 milliseconds or more and 10 milliseconds or less. That is, the control device 34 controls the sampling rate within the range of 0.2 milliseconds or more and 10 milliseconds or less. In other words, the control device 34 controls the execution at a rate (sampling rate) of 100 times/second or more and 5000 times/second or less. The control device 34 controls the execution at a rate (sampling rate) within the range of 100 times/second or more to 5000 times/second or less.

Furthermore, the control device 34 may control the interval (sampling rate) from the point where the electronic shutter turns on to the point where the electronic shutter turns on next, to 0.33 milliseconds or more and 1.6 milliseconds or less. That is, the control device 34 may control the sampling rate within the range of 0.33 milliseconds or more and 1.6 milliseconds or less. In other words, the control device 34 controls the execution at a rate (sampling rate) of 625 times/second or more and 3000 times/second or less. The control device 34 controls the execution at a rate (sampling rate) within the range of 625 times/second or more to 3000 times/second or less.

For example, it is known that when a colorectal polyp having a diameter of 5 mm is observed, an effective device can be provided for 99% of people who develop colorectal cancer. Therefore, when the color in the 5 mm diameter (φ) region can be determined, colorectal polyps leading to the development of colorectal cancer can be appropriately detected.

<13. Light Reception Control Interval Longer than 10 Milliseconds>

Although the above-described example is a case where the light reception control interval (also referred to as "sampling rate" in the above) is 10 milliseconds or less, the light reception control interval may be longer than 10 milliseconds. For example, not limited to 10 milliseconds or less, the light reception control interval may be controlled to any of 50 milliseconds or less, 100 milliseconds or less, 300 milliseconds or less, or 600 milliseconds or less. Hereinafter, each of the light reception control intervals of 10 milliseconds, 50 milliseconds, 100 milliseconds, 300 milliseconds, and 600 milliseconds will be described.

First, a case where the light reception control interval is 10 milliseconds will be described. Here, a case where spherical feces having a diameter (φ) of 10 mm is a detection target will be described as an example. In this manner, in the case of a spherical feces with a diameter (φ) of 10 mm, unlike the case of a piece of feces of about 100 mm, which will be described below, the feces is no longer connected to the anus at the position 40 mm below the anus, and the entire feces passes through the position 40 mm below the anus at a rate of 1.23 m/s. Based on this premise, the interval of light reception control from 10 milliseconds to 600 milliseconds will be described below.

In a case where the light reception control interval is set to 10 milliseconds, one type of beam of light is scanned (emitted) twice each in the region of φ10 mm as described above. This makes it possible to detect the pattern on the feces to which the light is emitted due to the difference in the information (image) acquired by the scan performed twice. Here, the pattern is a concept that includes various changes that occur on the feces surface, such as irregularities and changes in color on the feces surface. Accordingly, when the light reception control interval is set to 10 milliseconds and one type of beam of light is emitted to the feces of φ10 mm, the presence or absence of the feces pattern can be detected.

Moreover, in a case where the light reception control interval is set to 10 milliseconds, two types of beams of light are scanned (emitted) once each in the region of φ10 mm. This makes it possible to estimate the representative color of the feces to which the light has been emitted due to the difference in the information (image) acquired by the scan performed twice. By emitting two types of beams of light having different wavelengths to the feces in this manner, the representative color of the feces can be estimated based on the difference in the reflection intensity. For example, the representative color of feces can be estimated based on the difference and slope of the reflection intensity of two types of beams of light having different wavelengths, from the feces.

Here, the amount of ordinary feces is estimated to be 100 g to 250 g in weight and about 100 mm in length. In this case, at a position 40 mm below the anus, the feces is being discharged with the feces connected to the anus. Therefore, the feces connected to the anus has not fallen up to 60 mm from the lower end, at a rate same as the rate at which the feces is discharged from the anus, with the discharge rate 0.05 m/s. For example, assuming the length of the feces is 100 mm, the feces in a range 60 mm from the leading end passes at a position 40 mm below the anus at 0.05 m/s and the remaining 40 mm to the trailing end passes at a position 40 mm below the anus at 0.89 m/s. Based on this premise, each light reception control interval of 50 milliseconds or less, 100 milliseconds or less, 300 milliseconds or less, or 600 milliseconds or less will be described.

In a case where the light reception control interval is 50 milliseconds, one type of beam of light is scanned (emitted) 25 times to a region having a length of 100 mm, making it possible to detect the pattern of cracks appearing on the surface of the feces due to the reduced amount of moisture contained in the feces, leading to estimation of the properties of the feces corresponding to the amount of moisture in the feces. In a case where the light reception control interval is 50 milliseconds, two types of light are scanned (emitted) 12 times to a region of having a length of 100 mm, making it possible to detect the color distribution of the feces.

In addition, in a case where the light reception control interval is 100 milliseconds, one type of beam of light is scanned (emitted) 12 times to a region of having a length of 100 mm, making it possible to detect the contour of the feces. In addition, the contour of the feces can be detected, making it possible to detect whether the feces is disfigured with a large amount of moisture, or keeps its shape with a small amount of moisture. As described above, in the case of a piece of feces with a length of 100 mm, the range of the feces 60 mm from the leading end passes at 0.05 m/s at a position 40 mm below the anus. Accordingly, when the interval of light reception control is 100 milliseconds, it is possible to perform scan 12 times (=60 (mm)/50 (mm/s)/0.1 (s/time)).

In a case where the light reception control interval is 300 milliseconds, one type of beam of light is scanned (emitted) four times to a region of having a length of 100 mm, making it possible to detect the presence or absence of feces. In addition, in a case where the light reception control interval is 300 milliseconds, two types of light are scanned (emitted) twice to a region of having a length of 100 mm, making it possible to estimate the representative color of the feces.

In addition, in a case where the light reception control interval is 600 milliseconds, one type of beam of light is scanned (emitted) twice to a region of having a length of 100 mm, making it possible to detect the presence or absence of the feces.

The longer the light reception control interval (sampling period), the easier the control, making it possible to suppress an increase in the amount of data. In other words, the lower the sampling frequency (lower the sampling rate), the easier the control, making it possible to suppress the increase in the amount of data. In addition, the longer the light reception control interval, the longer the light receiving time can be obtained with a light source (light emitting element 121, or the like) with the same output intensity. Moreover, the longer the light receiving time, the more the light (reflected light from the feces) can be captured by a sensor (light receiving element 132, or the like).

Figure 32:
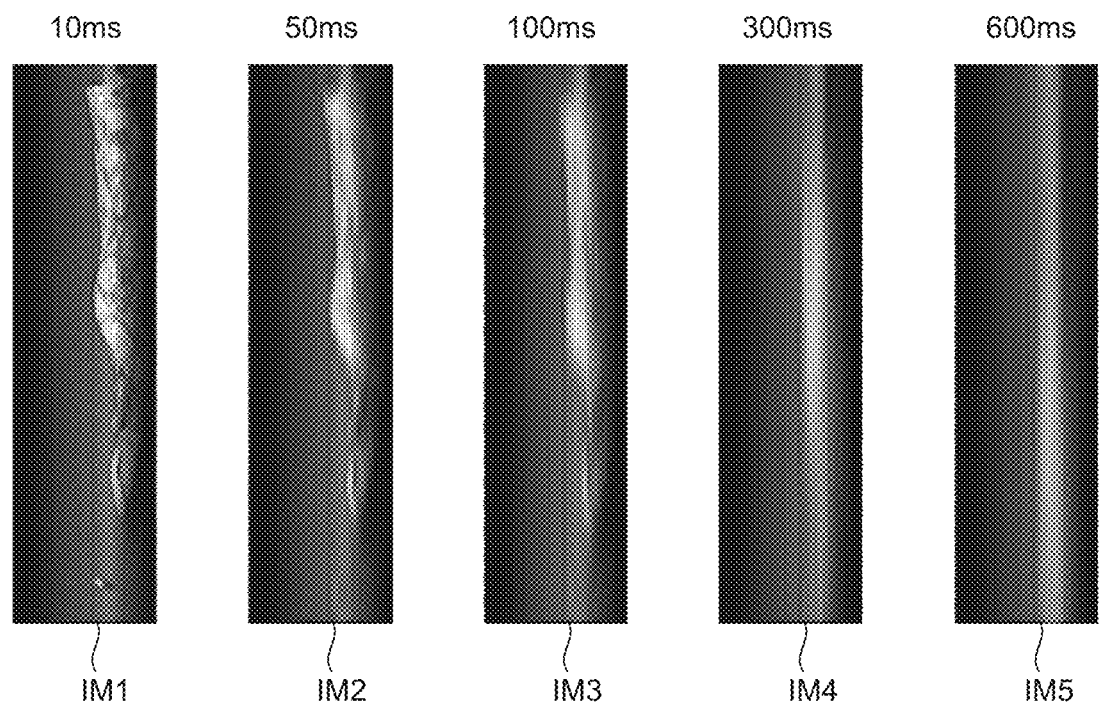
FIG. 32 is a diagram illustrating images of feces at each of intervals of light reception control.

Next, an image of the feces at various intervals of light reception control will be described with reference to FIG. 32. FIG. 32 is a diagram illustrating images of feces at various intervals of light reception control. FIG. 32 illustrates data obtained by continuously sampling the discharged feces before landing on the sealed water in the toilet bowl by using a toilet seat apparatus (corresponding to the toilet seat apparatus 2) equipped with a line sensor (corresponding to the light receiving element 132) in which photodetectors (light receiving elements) are arranged in one dimension. In the example of FIG. 32, hard-to-pass feces (hard feces) is illustrated as an example. Specifically, the feces illustrated in FIG. 32 is feces having low moisture and a lot of irregularities on the surface.

Of the outer surface portions of feces, brightly colored portions such as yellow and light yellowish brown have high reflectance. That is, the portions allow a large amount of light to be received by the light receiving element. By contrast, darker portions such as dark brown portions or shadows generated when the outer surface of the feces has irregularities due to low moisture, have low reflectance, leading to a small amount of light to be received by the light receiving element. By using a line sensor with light receiving elements arranged in one dimension to image (capture) the feces in the horizontal direction, it is possible to obtain highly characteristic data due to the colors and shadows. Each image of FIG. 32 illustrates a case where pieces of one-dimensional data obtained by imaging feces in the horizontal direction are continuously arranged in the vertical direction to form a two-dimensional image. In order to distinguish whether the pattern of the feces in the image of FIG. 32 is a difference in color or a shadow, beams of light having two or more different wavelengths are continuously emitted to the feces. By comparing the reflectance of light in each of wavelengths relative to each other, it is possible to distinguish whether the pattern of the feces in the image of FIG. 32 is a difference in color or a shadow.

When the light reception control interval is 10 milliseconds, the detailed pattern of the feces can be detected as illustrated in the image IM1 in FIG. 32. Specifically, when the light reception control interval is 10 milliseconds, it is possible to obtain the detailed pattern of the feces in which a fine linear black region is mixed into a white region as illustrated in the image IM1 in FIG. 32. In this manner, when the light reception control interval is 10 milliseconds, the detailed pattern of the feces can be obtained, leading to estimation of the amount of moisture contained in the feces like the Bristol scale.

Furthermore, when the light reception control interval is 50 milliseconds, the pattern of the feces can be obtained as illustrated in an image IM2 in FIG. 32. Specifically, when the light reception control interval is 50 milliseconds, a black region is mixed into a portion above a white region extending in vertical direction in the image IM2 in FIG. 32, indicating the pattern of the feces. In this manner, when the light reception control interval is 50 milliseconds, the pattern of the feces can be obtained, leading to estimation of an approximate amount of moisture, such as hard (small amount of moisture), normal, or soft (large amount of moisture).

When the light reception control interval is 100 milliseconds, the shape of the feces can be obtained as illustrated in an image IM3 in FIG. 32. Specifically, when the light reception control interval is 100 milliseconds, there is a white region extending in the vertical direction at portions ranging from the central portion to the right side in the horizontal direction in the image IM3 in FIG. 32, and this white region indicates the shape of the feces. In this manner, the light reception control interval 100 milliseconds allows acquisition of the shape of the feces, making it possible to estimate the contour of the feces, such that the shape of the feces is deformed (large amount of moisture), or the shape is maintained (less or normal moisture).

In addition, when the light reception control interval is 300 milliseconds, the approximate shape of the feces can be obtained as illustrated in the image IM4 in FIG. 32. Specifically, when the light reception control interval is 300 milliseconds, there is a white linear region extending in the vertical direction in an image IM4 in FIG. 32, and this white region indicates the approximate shape of the feces. In this manner, the light reception control interval 300 milliseconds allows acquisition of the approximate shape of the feces, making it possible to detect the presence or absence of the feces and size of the feces.

In addition, even when the light reception control interval is 600 milliseconds, the passage of the feces can be detected as illustrated in an image IM5 in FIG. 32. Specifically, when the light reception control interval is 600 milliseconds, there is a white linear region extending in the vertical direction in the image IM5 in FIG. 32, and this white region indicates the passage of the feces. In this manner, the light reception control interval 600 milliseconds allows detection of the passage of the feces, making it possible to detect the presence or absence of the feces. As illustrated in FIG. 32, the shorter the light reception control interval, the more detailed information about the feces can be obtained.

Noted that the above-described embodiments and modifications can be appropriately combined as long as the processes would not contradict each other.

Further effects and variations can be easily derived by those skilled in the art. For this reason, the broader aspects of the present invention are not limited to the particular details and representative embodiments expressed and described as above. Accordingly, various alterations and modifications can be made without departing from the spirit or scope of the general concept of the invention as defined by the appended claims and their equivalents.

REFERENCE SIGNS LIST

R TOILET ROOM
1 TOILET SYSTEM
2 TOILET SEAT APPARATUS
20 SECOND MEMORY
3 MAIN BODY
30 MAIN BODY COVER
31 OPENING
31b OPENING
32 HUMAN DETECTION SENSOR
33 SEATING DETECTION SENSOR
34 CONTROL DEVICE (CONTROL UNIT)
341 AD CONVERTER
342 ARITHMETIC PROCESSING DEVICE
343 ROM
344 FIRST MEMORY
4 TOILET LID
5 TOILET SEAT
6 CLEANSING NOZZLE
60 NOZZLE LID
7 WESTERN STYLE TOILET (TOILET BOWL)
71 SOLENOID VALVE
8 BOWL UNIT
9 RIM
10 OPERATION DEVICE
11 DISPLAY SCREEN
100 OPTICAL UNIT
110 LID
111 ACTUATOR
120 LIGHT EMITTING UNIT
121 LIGHT EMITTING ELEMENT
130 LIGHT RECEIVING UNIT
131 LENS
132 LIGHT RECEIVING ELEMENT
133 CASE

The invention claimed is:

1. A toilet seat apparatus to be placed on an upper part of a toilet bowl having a bowl unit that receives excrement, the toilet seat apparatus comprising:
   a toilet seat on which a user sits;
   a light emitting unit including a light emitting element that emits light;
   a light receiving unit including a light receiving element that receives light; and
   a control unit that controls energization of the light emitting element and application of voltage to the light receiving element, wherein
   the light emitting unit emits light toward falling feces discharged by the user,
   the light receiving unit receives the reflected light from the feces corresponding to the light emitted by the light emitting unit, and
   the control unit
   performs light reception control including transmitting a control instruction to open an electronic shutter to the light receiving element and energizing the light emitting element so as to permit reception of the reflected light from feces, and
   performs control of setting an interval from a start of execution of one light reception control to execution of light reception control subsequent to the one light reception control, to 0.2 milliseconds or more and 600 milliseconds or less.

2. The toilet seat apparatus according to claim 1, wherein the control unit performs control of setting an interval from a start of execution of the one light reception control to execution of the subsequent light reception control, to 300 milliseconds or less.

3. The toilet seat apparatus according to claim 1, wherein the control unit performs control of setting an interval from a start of execution of the one light reception control to execution of the subsequent light reception control, to 100 milliseconds or less.

4. The toilet seat apparatus according to claim 1, wherein the control unit performs control of setting an interval from a start of execution of the one light reception control to execution of the subsequent light reception control, to 50 milliseconds or less.

5. The toilet seat apparatus according to claim 1, wherein the control unit performs control of setting an interval from a start of execution of the one light reception control to execution of the subsequent light reception control, to 10 milliseconds or less.

6. The toilet seat apparatus according to claim 1 wherein the light emitting unit includes a plurality of light emitting elements each of which emits light,
   the plurality of light emitting elements is capable of emitting beams of light of different wavelengths,
   the control unit
   energizes only one light emitting element among the plurality of light emitting elements in the one light reception control, changes the light emitting element to be energized in the subsequent light reception control every time the one light reception control is completed, and
   performs control of setting the interval from the start of execution of one light reception control to the execution of the subsequent light reception control to 1.6 milliseconds or less.

7. The toilet seat apparatus according to claim 1, wherein the control unit sets energization time of the light emitting element to be different for each of wavelengths emitted by the light emitting element in the light reception control.

8. The toilet seat apparatus according to claim 1, further comprising a seating sensor that detects seating of the user on the toilet seat, wherein
   based on the detection by the seating sensor, the control unit performs the light reception control only while the user is seated.

9. An excrement detection apparatus to be disposed on a toilet bowl having a bowl unit that receives excrement, the excrement detection apparatus comprising:
   a light emitting unit including a light emitting element that emits light;
   a light receiving unit including a light receiving element that receives light; and
   a control unit that controls energization of the light emitting element and application of voltage to the light receiving element, wherein
   the light emitting unit emits light toward falling feces discharged by the user,
   the light receiving unit receives the reflected light from the feces corresponding to the light emitted by the light emitting unit, and
   the control unit
   performs light reception control including transmitting a control instruction to open an electronic shutter to the light receiving element and energizing the light emitting element so as to permit reception of the reflected light from feces, and performs control of setting an interval from a start of execution of one light reception control to execution of light reception control subsequent to the one light reception control, to 0.2 milliseconds or more and 600 milliseconds or less.

* * * * *